US006403587B1

(12) United States Patent
Kath et al.

(10) Patent No.: US 6,403,587 B1
(45) Date of Patent: Jun. 11, 2002

(54) HETEROARYL-HEXANOIC ACID AMIDE DERIVATIVES, THEIR PREPARATION AND THEIR USE AS SELECTIVE INHIBITORS OF MIP-1-α BINDING TO ITS CCR 1 RECEPTOR

(75) Inventors: John Charles Kath, Waterford; Matthew Frank Brown, Pawcatuck; Christopher Stanley Poss, North Stonington, all of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/380,269

(22) PCT Filed: Feb. 5, 1998

(86) PCT No.: PCT/US98/01568
§ 371 (c)(1),
(2), (4) Date: May 18, 2000

(87) PCT Pub. No.: WO98/38167
PCT Pub. Date: Sep. 3, 1998

Related U.S. Application Data
(60) Provisional application No. 60/039,169, filed on Feb. 26, 1997.

(51) Int. Cl.$^7$ .................... A61K 31/50; A01N 43/60; C07D 241/36; C07D 215/00
(52) U.S. Cl. .................... 514/249; 514/311; 514/312; 544/355; 546/152
(58) Field of Search ................. 514/249, 311, 514/312; 544/355; 546/152

(56) References Cited

U.S. PATENT DOCUMENTS 4,923,864 A    5/1990   Rosat ................ 514/234.8

FOREIGN PATENT DOCUMENTS

| EP | 0184550 | 11/1985 |
| EP | 0321192 | 12/1988 |
| EP | 0374098 | 12/1989 |
| EP | 0708085 | 4/1996 |
| WO | 8901488 | 2/1989 |
| WO | 9217490 | 10/1992 |
| WO | 9302057 | 2/1993 |
| WO | 9317003 | 9/1993 |
| WO | 9507269 | 3/1995 |

OTHER PUBLICATIONS

Andrew G. Myers, et al.; A Practical Method for the Synthesis of D–or L –Amino Acids by the Alkylation of (+)–or (–) Pseudoephedrine Glycinamide; J. Am. Chem. Soc. (1995) 117; pp. 8488–8489.

Andrew G. Meyers, et al.; A One–Step Synthesis of Pseudoephedrine Glycinamide, a Versatile Precursor for the Synthesis of –Amino Acids; Tetrahedron Letters; (1955); vol. 36, No. 26; pp. 4555–4558.

Kenso Soai, et al.; The Preparation of N–Protected Amino Alcohols and N–Protected Peptide Alcohol by Reduction of the Corresponding Esters with Sodium Borohydride, An Improved Procedure Involving a slow addition of a Small Amount of Methanol; Bull. Chem. Soc., vol. 57, No. 8; pp. 2327–2328.

C. Freeman Stanfield, et al.; Synthesis of Protected Amino Alcohols; A Comparative Study; Am. Chem. Soc.; (1981) pp. 1946–1947.

Ann. E. Decamp; Stereocontrolled Addition of Propionate Homoenolate Equivalents to Chiral –Amino Aldehydes; Tetrahedron Letters; (1991); vol. 32, No. 16; pp. 1867–1870.

Andrew H. Fray, et al.; A Short Stereoselective Synthesis of the Lactone precursor to 2R, 4S, 5S, Hydroxyethylene Dipeptide Isosteres; J. Org. Chem; (1986) vol. 51, 4828–2833.

T. K. Sawyer, et al.; Peptidomimetic Inhibitors of Human Immunodeficiency Virus Protease (HIV–PR): Design, Enzyme Binding and Selectivity, Antiviral Efficacy and Cell Permeability Properties; Bioorganic & Med. Chem. Letters; (1993); vol. 3, No. 5; pp. 819–824.

S. Natarajan, et al.; Ketomethylureas A. New Class of Angiotensin Converting Enzyme Inhibitors; J. Enzyme Inhibition; (1988), vol. 2; pp. 91–97.

Damian Grobelny, et. al; Aldehyde and Ketone Substrate Analogues Inhibit the Collagenase of Clostridium; Biochem. (1985); vol. 24; pp. 6145–6152.

Primary Examiner—Mukund J. Shah
Assistant Examiner—Tamthom N. Truong
(74) Attorney, Agent, or Firm—Peter C. Richardson; Gregg C. Benson; B. Timothy Creagan

(57) ABSTRACT

Compounds of the formula

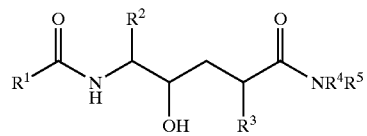

wherein $R^1$, $R^2$, $R^3$, $R^4$, $R^5$ and $R^6$ are as described in the specification are useful to treat inflammation and other immune disorders.

19 Claims, No Drawings

HETEROARYL-HEXANOIC ACID AMIDE DERIVATIVES, THEIR PREPARATION AND THEIR USE AS SELECTIVE INHIBITORS OF MIP-1-α BINDING TO ITS CCR 1 RECEPTOR

This application claims the benefit of provisional application No. 60/039,169 filed Feb. 26, 1997.

BACKGROUND OF THE INVENTION

The present invention relates to novel hexanoic acid derivatives, methods of use and pharmaceutical compositions containing them.

The compounds of the invention are potent and selective inhibitors of MIP-1α binding to its receptor CCR1 found on inflammatory and immunomodulatory cells (preferably leukocytes and lymphocytes). The CCR1 receptor is also sometimes referred to as the CC-CKR1 receptor. These compounds also inhibit MIP-1α (and the related chemokine shown to interact with CCR1 (e.g., RANTES and MCP-3)) induced chemotaxis of THP-1 cells and human leukocytes and are potentially useful for the treatment or prevention of autoimmune diseases (such as rheumatoid arthritis, type I diabetes (recent onset), inflammatory bowel disease, optic neuritis, psoriasis, multiple sclerosis, polymyalgia rheumatica, uveitis, and vasculitis), acute and chronic inflammatory conditions (such as osteoarthritis, adult Respiratory Distress Syndrome, Respiratory Distress Syndrome of infancy, ischemia reperfusion injury, and glomerulonephritis), allergic conditions (such as asthma and atopic dermatitis), infection associated with inflammation (such as viral inflammation (including influenza and hepatitis) and Guillian-Barre), transplantation tissue rejection (chronic and acute), organ rejection (chronic and acute), atherosclerosis, restenosis, HIV infectivity (co-receptor usage), and granulomatous diseases (including sarcoidosis, leprosy and tuberculosis).

MIP-1α and RANTES are soluble chemotactic peptides (chemokines) which are produced by inflammatory cells, in particular CD8+ lymphocytes, polymorphonuclear leukocytes (PMNs) and macrophages, *J.Biol. Chem.*, 270 (30) 29671–29675 (1995). These chemokines act by inducing the migration and activation of key inflammatory and immunomodulatory cells. Elevated levels of chemokines have been found in the synovial fluid of rheumatoid arthritis patients, chronic and rejecting tissue transplant patients and in the nasal secretions of allergic rhinitis patients following allergen exposure (Teran , et al.,*J. Immunol.*, 1806–1812 (1996), and Kuna et al., *J. Allergy Clin. Immunol.* 321 (1994)). Antibodies which interfere with the chemokine/receptor interaction by neutralizing MIP1α or gene disruption have provided direct evidence for the role of MIP-1α and RANTES in disease by limiting the recruitment of monocytes and CD8+ lymphocytes (Smith et al.,*J. Immunol*, 153, 4704 (1994) and Cook et al., *Science*, 269, 1583 (1995)). Together this data demonstrates that CCR1 antagonists would be an effective at treatment of several immune based diseases. The compounds described within are potent and selective antagonists of CCR1. No other small molecule antagonists of the MIP-1α/RANTES interaction with CCR1 are currently known.

U.S. Pat. No. 4,923,864, issued May 8, 1990, refers to certain heterocyclic hexanamides that are useful for treating hypertension.

PCT publication WO 89/01488, published Feb. 23, 1989, refers to renin inhibiting peptides which possess nonpeptide linkages.

PCT publication WO 93/ 025057, published Feb. 4, 1993, refers to dipeptide analogs which are claimed to inhibit retroviral proteases.

PCT publication WO 93/17003, published Sep. 2, 1993, refers to other dipeptide analogs which are claimed to inhibit retroviral proteases.

PCT publication WO 92/17490, published Oct. 15, 1992, refers to peptides containing at least one O-phosphate monoester or diester. The compounds are claimed to possess activity for inhibiting retroviruses.

European Patent Publication 708,085, published Apr. 24, 1996, refers to antiviral ethers of aspartate protease inhibitors.

SUMMARY OF THE INVENTION

The present invention relates to compounds of the formula

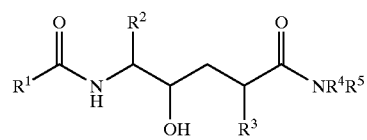

wherein $R^1$ is ($C_2$–$C_9$)heteroaryl optionally substituted with one or more substituents (preferably one to three substituents) independently selected from the group consisting of hydrogen, halo, CN, ($C_1$–$C_6$)alkyl optionally substituted with one or more fluorine atoms (preferably one to three fluorine atoms), hydroxy, hydroxy-($C_1$–$C_6$)alkyl, ($C_1$–$C_6$)alkoxy optionally substituted with one or more fluorine atoms (preferably one to three fluorine atoms), ($C_1$–$C_6$)alkoxy($C_1$–$C_6$)alkyl, HO—(C=O)—, ($C_1$–$C_6$)alkyl-O—(C=O)—, HO—(C=O)—($C_1$–$C_6$)alkyl, ($C_1$–$C_6$)alkyl-O—(C=O)—($C_1$–$C_6$)alkyl, ($C_1$–$C_6$)alkyl-(C=O)—O—, ($C_1$–$C_6$)alkyl-(C=O)—O—($C_1$–$C_6$)alkyl, H(O=C)—, H(O=C)—($C_1$–$C_6$)alkyl, ($C_1$–$C_6$)alkyl(O=C)—, ($C_1$–$C_6$)alkyl(O=C)—($C_1$–$C_6$)alkyl, $NO_2$, amino, ($C_1$–$C_6$)alkylamino, [($C_1$–$C_6$)]$_2$amino, amino($C_1$–$C_6$)alkyl, ($C_1$–$C_6$)alkylamino($C_1$–$C_6$)alkyl, [($C_1$–$C_6$)alkyl]$_2$amino($C_1$–$C_6$)alkyl, $H_2$N—(C=O)—, ($C_1$–$C_6$)alkyl-NH—(C=O)—, [($C_1$–$C_6$)alkyl]$_2$N—(C=O)—, $H_2$N(C=O)—($C_1$–$C_6$)alkyl, ($C_1$–$C_6$)alkyl-HN(C=O)—($C_1$–$C_6$)alkyl, [($C_1$–$C_6$)alkyl]$_2$N—(C=O)—($C_1$–$C_6$)alkyl, H(O=C)—NH—, ($C_1$–$C_6$)alkyl(C=O)—NH, ($C_1$–$C_6$)alkyl(C=O)— [NH]($C_1$–$C_6$)alkyl, ($C_1$–$C_6$)alkyl(C=O)—[N($C_1$–$C_6$)alkyl]($C_1$–$C_6$)alkyl, ($C_1$–$C_6$)alkyl-S—, ($C_1$–$C_6$)alkyl-(S=O)—, ($C_1$–$C_6$)alkyl-$SO_2$—, ($C_1$–$C_6$)alkyl-$SO_2$—NH—, $H_2$N—$SO_2$—, $H_2$N—$SO_2$—($C_1$–$C_6$)alkyl, ($C_1$–$C_6$)alkylHN—$SO_2$—($C_1$–$C_6$)alkyl, [($C_1$–$C_6$)alkyl]$_2$N—$SO_2$—($C_1$–$C_6$)alkyl, $CF_3SO_3$—, $C_1$–$C_6$)alkyl-$SO_3$—, phenyl, ($C_3$–$C_{10}$)cycloalkyl, ($C_2$–$C_9$)heterocycloalkyl, and ($C_2$–$C_9$)heteroaryl;

$R^2$ is phenyl-$(CH_2)_m$—, naphthyl-$(CH_2)_m$—, ($C_3$–$C_{10}$)cycloalkyl-$(CH_2)_m$—, ($C_1$–$C_6$)alkyl or ($C_2$–$C_9$)heteroaryl-$(CH_2)_m$—, wherein m is an interger from zero to four, wherein each of said phenyl, naphthyl, ($C_3$–$C_{10}$)cycloalkyl or ($C_2$–$C_9$)heteroaryl moieties of said phenyl-$(CH_2)_m$—, naphthyl-$(CH_2)_m$—, ($C_3$–$C_{10}$)cycloalkyl-$(CH_2)_m$— or ($C_2$–$C_9$)heteroaryl-$(CH_2)_m$— groups may optionally be substituted with one or more substituents (preferably one to three substituents) independently selected from hydrogen, halo, CN, $(C_1-C_6)$ alkyl optionally substituted with one or more fluorine atoms (preferably one to three fluorine atoms), hydroxy, hydroxy-$(C_1-C_6)$alkyl, $(C_1-C_6)$alkoxy optionally substituted with one or more fluorine atoms (preferably one to three fluorine atoms), $(C_1-C_6)$alkoxy $(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$ amino, amino$(C_1-C_6)$alkylamino$(C_1-C_6)$alkyl, $[(C_1-C_6)$alkyl$]_2$amino$(C_1-C_6)$alkyl, $H_2N$—(C=O)—$(C_1-C_6)$alkyl-NH—(C=O)—, $[(C_1-C_6)$alkyl$]_2N$—(C=O)—, $H_2N$(C=O)—$(C_1-C_6)$alkyl, $(C_1-C_6)$alkyl-HN(C=O)—$(C_1-C_6)$alkyl, $[(C_1-C_6)$alkyl$]_2N$—(C=O)—$(C_1-C_6)$alkyl, H(O=C)—NH—, $(C_1-C_6)$alkyl(C=O)—NH, $(C_1-C_6)$alkyl(C=O)—[NH $(C_1-C_6)$alkyl, $(C_1-C_6$alkyl(C=O)—[N$(C_1-C_6)$alkyl] $(C_1-C_6)$alkyl, $(C_1-C_6)$alkyl-S—, $(C_1-C_6)$alkyl-(S=O)—, $(C_1-C_6)$alkyl-$SO_2$—, $(C_1C_6)$alkyl-$SO_2$—NH—, $H_2N$—$SO_2$—, $H_2N$—$SO_2$—$(C_1-C_6)$alkyl, $(C_1-C_6)$alkylHN—$SO_2$—$(C_1-C_6)$alkyl, $[(C_1-C_6)$alkyl$]_2N$—$SO_2$—$(C_1-C_6)$alkyl, $CF_3SO_3$—, $(C_1-C_6)$alkyl-$SO_3$—, phenyl, phenoxy, benzyloxy, $(C_3-C_{10})$cycloalkyl, $(C_2-C_9)$heterocycloalkyl, and $(C_2-C_9)$heteroaryl;

$R^3$ is hydrogen, $(C_1-C_{10})$alkyl, $(C_3-C_{10})$cycloalkyl-$(CH_2)_n$—, $(C_2-C_9)$heterocycloalkyl-$(CH_2)_n$—, $(C_2-C_9)$heteroaryl-$(CH_2)_n$— or aryl-$(CH_2)_n$—; wherein n is an interger from zero to six;

wherein said $R^3$ $(C_1-C_{10})$alkyl group may optionally be substituted with one or more substituents, (preferably from one to three substituents) independently selected from hydrogen, halo, CN, $(C_1-C_6)$alkyl optionally substituted with one or more fluorine atoms (preferably one to three fluorine atoms), hydroxy, hydroxy-$(C_1-C_6)$alkyl, $(C_1-C_6)$alkoxy optionally substituted with one or more fluorine atoms (preferably one to three fluorine atoms), $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_6-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino $(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N$(C=O)—$(C_1-C_6)$alkyl, $(C_1C_6)$alkyl-HN(C=O)—$(C_1-C_6)$alkyl, $[(C_1-C_6)$alkyl$]_2N$—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl, (S=O)—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkylHN—$SO_2$—$(C_1-C_6)$alkyl, $[(C_1-C_6)$alkyl$]_2N$—$SO_2$—$(C_1-C_6)$alkyl, $CF_3SO_3$—, $(C_1-C_6)$alkyl-$SO_3$—, phenyl, $(C_3-C_{10})$cycloalkyl, $(C_2-C_9)$heterocycloalkyl, and $(C_2-C_9)$heteroaryl; and wherein any of the carbon-carbon single bonds of said $(C_1-C_{10})$alkyl may optionally be replaced by a carbon-carbon double bond;

wherein the $(C_3-C_{10})$cycloalkyl moiety of said $R^3$ $(C_3-C_{10})$cycloalkyl-$(CH_2)_n$— group may optionally be substituted by one to three substitutents independently selected from the group consisting of hydrogen, halo, CN, $(C_1-C_6)$alkyl optionally substituted with one or more fluorine atoms (preferably one to three fluorine atoms), hydroxy, hydroxy-$(C_1-C_6)$alkyl, $(C_1-C_6)$alkoxy optionally substituted with one or more fluorine atoms (preferably one to three fluorine atoms), $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkylHN—$SO_2$—$(C_1-C_6)$alkyl, $[(C_1-C_6)$alkyl$]_2N$—$SO_2$—$(C_1-C_6)$alkyl, $CF_3SO_3$—, $(C_1-C_6)$alkyl-$SO_3$—, phenyl, $(C_3-C_{10})$cycloalkyl, $(C_2-C_9)$heterocycloalkyl, and $(C_2-C_9)$heteroaryl;

wherein the $(C_2-C_9)$heterocycloalkyl moiety of said $R^3$ $(C_2-C_9)$heterocycloalkyl-$(CH_2)_n$— group may contain from one to three heteroatoms independently selected from nitrogen, sulfur, oxygen, >S(=O), >$SO_2$ or >$NR^6$, wherein said $(C_2-C_9)$heterocycloalkyl moiety of said $(C_2-C_9)$heterocycloalkyl-$(CH_2)_n$— group may optionally be substituted on any of the ring carbon atoms capable of forming an additional bond (preferably one to three substitutents per ring) with a substituent independently selected from the group consisting of hydrogen, halo, CN, $(C_1-C_6)$alkyl optionally substituted with one or more fluorine atoms (preferably one to three fluorine atoms), hydroxy, hydroxy-$(C_1-C_6)$alkyl, $(C_1-C_6)$alkoxy optionally substituted with one or more fluorine atoms (preferably one to three fluorine atoms), $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino $(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N$(C=O)—$(C_1-C_6)$alkyl, $(C_1-C_6)$alkyl-HN(C=O)—$(C_1-C_6)$alkyl, $[(C_1-C_6)$alkyl$]_2N$—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkylHN—$SO_2$—$(C_1-C_6)$alkyl, $[(C_1-C_6)$alkyl$]_2N$—$SO_2$—$(C_1-C_6)$alkyl, $CF_3SO_3$—, $(C_1-C_6)$alkyl-$SO_3$—, phenyl, $(C_3-C_{10})$cycloalkyl, $(C_2-C_9)$heterocycloalkyl, and $(C_2-C_9)$heteroaryl;

wherein the $(C_2-C_9)$heteroaryl moiety of said $R^3$ $(C_2-C_9)$heteroaryl-$(CH_2)_n$— group may contain from one to three heteroatoms independently selected from nitrogen, sulfur or oxygen, wherein said $(C_2-C_9)$heteroaryl moiety of said $(C_2-C_9)$heteroaryl-$(CH_2)_n$— group may optionally be substituted on any of the ring carbon atoms capable of forming an additional bond (preferably one to three substitutents per ring) with a substituent selected from the group consisting of hydrogen, halo, CN, $(C_1-C_6)$alkyl optionally substituted with one or more fluorine atoms (preferably one to three fluorine atoms), hydroxy, hydroxy-$(C_1-C_6)$alkyl, $(C_1-C_6)$alkoxy optionally substituted with one or more fluorine atoms (preferably one to three fluorine atoms), $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N(C=O)$—$(C_1-C_6)$alkyl, $(C_1-C_6)$alkyl-HN(C=O)—$(C_1-C_6)$alkyl, $[(C_1-C_6)$alkyl$]_2N$—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkylHN—$SO_2$—$(C_1-C_6)$alkyl, $[(C_1-C_6)$alkyl$]_2N$—$SO_2$—$(C_1-C_6)$alkyl, $CF_3SO_3$—, $(C_1-C_6)$alkyl-$SO_3$—, phenyl, $(C_3-C_{10})$cycloalkyl, $(C_2-C_9)$heterocycloalkyl, and $(C_2-C_9)$heteroaryl; and wherein said aryl moiety of said $R^3$ aryl-$(CH_2)_n$— group is optionally substituted phenyl or naphthyl, wherein said phenyl and naphthyl may optionally be substituted with from one to three substituents independently selected from the group consisting of hydrogen, halo, CN, $(C_1-C_6)$alkyl optionally substituted with one or more fluorine atoms (preferably one to three fluorine atoms), hydroxy, hydroxy-$(C_1-C_6)$alkyl, $(C_1-C_6)$alkoxy optionally substituted with one or more fluorine atoms (preferably one to three fluorine atoms), $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N(C=O)$—$(C_1-C_6)$alkyl, $(C_1-C_6)$alkyl-HN(C=O)—$(C_1-C_6)$alkyl, $[(C_1-C_6)$alkyl$]_2N$—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkyl HN—$SO_2$—$(C_1-C_6)$alkyl, $[(C_1-C_6)$alkyl$]_2N$—$SO_2$—$(C_1-C_6)$alkyl, $CF_3SO_3$—, $(C_1-C_6)$alkyl-$SO_3$—, phenyl, $(C_3-C_{10})$cycloalkyl, $(C_2-C_9)$heterocycloalkyl, and $(C_2-C_9)$heteroaryl;

or $R^3$ and the carbon to which it is attached form a five to seven membered carbocyclic ring, wherein any of the carbon atoms of said five membered carbocyclic ring may optionally be substituted with a substituent selected from the group consisting of hydrogen, halo, CN, $(C_1-C_6)$alkyl optionally substituted with one or more fluorine atoms (preferably one to three fluorine atoms), hydroxy, hydroxy-$(C_1-C_6)$alkyl, $(C_1-C_6)$alkoxy optionally substituted with one or more fluorine atoms (preferably one to three fluorine atoms), $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N$(C=O)—$(C_1-C_6)$alkyl, $(C_1-C_6)$alkyl-HN(C=O)—$(C_1-C_6)$alkyl, $[(C_1-C_6)$alkyl$]_2N$—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkylHN—$SO_2$—$(C_1-C_6)$alkyl, $[(C_1-C_6)$alkyl$]_2N$—$SO_2$—$(C_1-C_6)$alkyl, $CF_3SO_3$—, $(C_1-C_6)$alkyl-$SO_3$—, phenyl, $(C_3-C_{10})$cycloalkyl, $(C_2-C_9)$heterocycloalkyl, and $(C_2-C_9)$heteroaryl; wherein one of the carbon-carbon bonds of said five to seven membered carbocyclic ring may optionally be fused to an optionally substituted phenyl ring, wherein said substitutents may be independently selected from hydrogen, halo, CN, $(C_1-C_6)$alkyl optionally substituted with one or more fluorine atoms (preferably one to three fluorine atoms), hydroxy, hydroxy-$(C_1-C_6)$alkyl, $(C_1-C_6)$alkoxy optionally substituted with one or more fluorine atoms (preferably one to three fluorine atoms), $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N(C=O)$—$(C_1-C_6)$alkyl, $(C_1-C_6)$alkyl-HN(C=O)—$(C_1-C_6)$alkyl, $[(C_1-C_6)$alkyl$]_2N$—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkylHN—$SO_2$—$(C_1-C_6)$alkyl, $[(C_1-C_6)$alkyl$]_2N$—$SO_2$—$(C_1-C_6)$alkyl, $CF_3SO_3$—, $(C_1-C_6)$alkyl-$SO_3$—, phenyl, $(C_3-C_{10})$cycloalkyl, $(C_2-C_9)$heterocycloalkyl, and $(C_2-C_9)$heteroaryl;

$R^4$ is hydrogen, $(C_1-C_6)$alkyl, hydroxy, $(C_1-C_6)$alkoxy, hydroxy$(C_1-C_6)$alkyl, $(C_1-C_6)$alkoxy$(C=O)$—, $(C_3-C_{10})$cycloalkyl-$(CH_2)_p$—, $(C_2-C_9)$heterocycloalkyl-$(CH_2)_p$—, $(C_2-C_9)$heteroaryl-$(CH_2)_p$—, phenyl-$(CH_2)_p$—, or naphthyl-$(CH_2)_p$—, wherein p is an integer from zero to four; wherein said $(C_2-C_9)$heterocycloalkyl, $(C_2-C_9)$heteroaryl, phenyl and naphthyl groups of said $(C_2-C_9)$heterocycloalkyl-$(CH_2)_p$—, $(C_2-C_9)$heteroaryl-$(CH_2)_p$—, phenyl-$(CH_2)_p$—, or naphthyl-$(CH_2)_p$— may be optionally substituted on any of the ring atoms capable of supporting an additional bond (preferably zero to two substituents per ring) with a substituent selected from the group consisting of hydrogen, halo, CN, $(C_1-C_6)$alkyl optionally substituted with one or more fluorine atoms (preferably one to three fluorine atoms), hydroxy, hydroxy-$(C_1-C_6)$alkyl, $(C_1-C_6)$alkoxy optionally substituted with one or more fluorine atoms (preferably one to three fluorine atoms), $(C_1-C_6)$alkoxy $(C_1-C_6)$alkyl, HO—$(C=O)$—, $(C_1-C_6)$alkyl-O—$(C=O)$—, HO—$(C=O)$—$(C_1-C_6)$alkyl, $(C_1-C_6)$alkyl-O—$(C=O)$—$(C_1-C_6)$alkyl, $(C_1-C_6)$alkyl-$(C=O)$—O—, $(C_1-C_6)$alkyl-$(C=O)$—O—$(C_1-C_6)$alkyl, H(O=C)—, H(O=C)—$(C_1-C_6)$alkyl, $(C_1-C6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino $(C_1-C_6)$alkyl, $[(C_1-C_6)$alkyl$]_2$amino$(C_1-C_6)$alkyl, $H_2N$—$(C=O)$—, $(C_1-C_6)$alkyl-NH—$(C=O)$—, $[(C_1-C_6)$alkyl$]_2N$—$(C=O)$—, $H_2N(C=O)$—$(C_1-C_6)$alkyl, $(C_1-C_6)$alkyl-HN$(C=O)$—$(C_1-C_6)$alkyl, $[(C_1-C_6)$alkyl$]_2N$—$(C=O)$—$(C_1-C_6)$alkyl, H(O=C)—NH—, $(C_1-C_6)$alkyl$(C=O)$—NH, $(C_1-C_6)$alkyl$(C=O)$—[NH]$(C_1-C_6)$alkyl, $(C_1-C_6)$alkyl$(C=O)$—[N$(C_1-C_6)$alkyl]$(C_1-C_6)$alkyl, $(C_1-C_6)$alkyl-S—, $(C_1-C_6)$alkyl-$(S=O)$—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkylHN—$SO_2$—$(C_1-C_6)$alkyl, $[(C_1-C_6)$alkyl$]_2N$—$SO_2$—$(C_1-C_6)$alkyl, $CF_3SO_3$—, $(C_1-C_6)$alkyl-$SO_3$, phenyl, $(C_3-C_{10})$cycloalkyl, $(C_2-C_9)$heterocycloalkyl, and $(C_2-C_9)$heteroaryl;

or $R^4$ and $R^5$ together with the nitrogen atom to which they are attached form a $(C_2-C_9)$heterocycloalkyl group wherein any of the ring atoms of said $(C_2-C_9)$ heterocycloalkyl group may optionally be substituted, preferably from zero to two substituents, with a substituent selected from the group consisting of hydrogen, halo, CN, $(C_1-C_6)$alkyl optionally substituted with one or more fluorine atoms (preferably one to three fluorine atoms), hydroxy, hydroxy-$(C_1-C_6)$alkyl, $(C_1-C_6)$alkoxy optionally substituted with one or more fluorine atoms (preferably one to three fluorine atoms), $(C_1-C_6)$alkoxy$(C_1-C_6)$alkyl, HO—$(C=O)$—, $(C_1-C_6)$alkyl-O—$(C=O)$—, HO—$(C=O)$—$(C_1-C_6)$alkyl, $(C_1-C_6)$alkyl-O—$(C=O)$—$(C_1-C_6)$alkyl, $(C_1-C_6)$alkyl-$(C=O)$—O—, $(C_1-C_6)$alkyl-$(C=O)$—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino $(C_1-C_6)$alkyl, $[(C_1-C_6)$alkyl$]_2$amino$(C_1-C_6)$alkyl, $H_2N$—$(C=O)$—, $(C_1-C_6)$alkyl-NH—$(C=O)$—, $[(C_1-C_6)$alkyl$]_2N$—$(C=O)$—, $H_2N(C=O)$—$(C_1-C_6)$alkyl, $(C_1-C_6)$alkyl-HN$(C=O)$—$(C_1-C_6)$alkyl, $[(C_1-C_6)$alkyl$]_2N$—$(C=O)$—$(C_1-C_6)$alkyl, H(O=C)—NH—, $(C_1-C_6)$alkyl$(C=O)$—NH, $(C_1-C_6)$alkyl$(C=O)$—[NH]$(C_1-C_6)$alkyl, $(C_1-C_6)$alkyl$(C=O)$—[N$(C_1-C_6)$alkyl]$(C_1-C_6)$alkyl, $(C_1-C_6)$alkyl-S—, $(C_1-C_6)$alkyl-$(S=O)$—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkylHN—$SO_2$—$(C_1-C_6)$alkyl, $[(C_1-C_6)$alkyl$]_2N$—$SO_2$—$(C_1-C_6)$alkyl, $CF_3SO_3$—, $(C_1-C_6)$alkyl-$SO_3$—, phenyl, $(C_3-C_{10})$cycloalkyl, $(C_2-C_9)$heterocycloalkyl, and $(C_2-C_9)$heteroaryl, and $(C_2-C_9)$heteroaryl;

$R^5$ is hydrogen, $(C_1-C_6)$alkyl or amino;

$R^6$ is hydrogen, $(C_1-C_6)$alkyl, $(C_1-C_6)$alkoxy-$(CH_2)_g$—, $(C_1-C_6)$alkoxy$(C=O)$—$(CH_2)_g$—, $(C_1-C_6)$alkyl-$(SO_2)$—$(CH_2)_g$—, $(C_6-C_{10})$aryloxy-$(CH_2)_g$—, $(C_6-C_{10})$aryloxy$(C=O)$—$(CH_2)_g$—, or $(C_6-C_{10})$aryl-$(SO_2)$—$(CH_2)_g$—, wherein g is an integer from zero to four;

with the proviso that when one of $R^4$ or $R^5$ is hydrogen, and the other of $R^4$ or $R^5$ is $(C_1-C_6)$alkyl; $R^2$ is $(C_3-C_{10})$cycloalkyl or isopropyl and $R^3$ is $(C_3-C_5)$ alkyl, phenyl, methylvinyl, dimethylvinyl, halovinyl, hydroxy$(C_1-C_3)$alkyl or amino$(C_1-C_4)$alkyl then $R^1$ must be other than indol-5-yl, 6-azaindol-2-yl, 2,3-dichloro-pyrrol-5-yl, 4-hydroxyquinolin-3-yl, 2-hydroxyquinoxalin-3-yl, 6-azaindolin-3-yl, or optionally substituted indol-2 or 3-yl;

and the pharmaceutically acceptable salts of such compounds.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3- naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The compounds of this invention may contain olefin-like double bonds. When such bonds are present, the compounds of the invention exist as cis and trans configurations and as mixtures thereof.

Unless otherwise indicated, the alkyl and alkenyl groups referred to herein, as well as the alkyl moieties of other groups referred to herein (e.g., alkoxy), may be linear or branched, and they may also be cyclic (e.g., cyclopropyl, cyclobutyl, cyclopentyl, cyclohexyl or cycloheptyl) or be linear or branched and contain cyclic moieties. Branched groups such as 2-methylbutyl, 2-methylpentyl are defined such that the lowest number is the carbon furthest from the point of attachment. Unless otherwise indicated, halogen includes fluorine, chlorine, bromine, and iodine.

($C_3$–$C_{10}$)Cycloalkyl when used herein refers to cycloalkyl groups containing zero to two levels of unsaturation such as cyclopropyl, cyclobutyl, cyclopentyl, cyclopentenyl, cyclohexyl, cyclohexenyl, 1,3-cyclohexadiene, cycloheptyl, cycloheptenyl, bicyclo[3.2.1]octane, norbornanyl etc.

($C_2$–$C_9$)Heterocycloalkyl when used herein refers to pyrrolidinyl, tetrahydrofuranyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, chromanyl, etc. One of ordinary skill in the art will understand that the connection of said ($C_2$–$C_9$)heterocycloalkyl rings is through a carbon or a $sp^3$ hybridized nitrogen heteroatom.

($C_2$–$C_9$)Heteroaryl when used herein refers to furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, benzoxazinyl; etc. One of ordinary skill in the art will understand that the connection of said ($C_2$–$C_9$) heterocycloalkyl rings is through a carbon atom or a $sp^3$ hybridized nitrogen heteroatom.

Aryl when used herein refers to phenyl or naphthyl.

The compounds of this invention include all conformational isomers (e.g., cis and trans isomers) and all optical isomers of compounds of the formula I (e.g., enantiomers and diastereomers), as well as racemic, diastereomeric and other mixtures of such isomers.

Preferred compounds of the of formula I include those with the stereochemistry depicted in formula

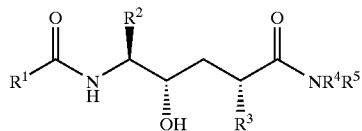

Ia

Preferred compounds of the formula I include those wherein $R^1$ is optionally substituted pyrazolo[3,4-b]pyridinyl, cinnolinyl, pyridinyl, 6,7-dihydro-5H-[1]pyrindinyl, benzothiazolyl, indolyl, pyrazinyl, benzoimidazolyl, benzofuranyl, benzo[b]thiophenyl, naphthalenyl, quinoxalinyl, isoquinolinyl, 5,6,7,8-tetrahydro-quinolin-3-yl or quinolinyl, more preferably pyrazolo[3,4-b]pyridin-5-yl, cinnolin4-yl, pyridin-2-yl, 6,7-dihydro-5H-[1]pyrindin-3-yl, benzothiazol-2-yl, indol-2-yl, pyrazin-2-yl, benzoimidazol-2-yl, benzofuran-2-yl, benzo[b]thiophen-2-yl, naphthalen-2-yl, quinoxalin-2-yl, quinoxalin6-yl, isoquinolin-1-yl, isoquinolin-3-yl, isoquinolin-4-yl, 5,6,7,8-tetrahydro-quinolin-3-yl, quinolin-2-yl, quinolin-3-yl, quinolin4-yl or quinolin-6-yl, most preferably quinoxalin-6-yl, quinolin-2-yl, quinolin-3-yl, quinoxalin-2-yl, quinolin4-yl or quinolin-6-yl.

Other preferred compounds of formula I include those wherein $R^2$ is optionally substituted phenyl, benzyl, naphthyl, cyclohexyl, thienyl, thiazolyl, pyridyl, oxazolyl, furanyl, or thiophenyl; wherein said substituents are independently selected from hydrogen, halo, ($C_1$–$C_6$)alkyl, trifluoromethyl, trifluoromethoxy, hydroxy, —C(=O)—OH, ($C_1$–$C_6$)alkoxy, ($C_1$–$C_6$)alkoxy(C=O)—, $NO_2$, amino, ($C_1$–$C_6$)alkylamino, [($C_1$–$C_6$)alkyl]$_2$amino, ($C_1$–$C_6$)alkyl-O—(C=O)—, HO—(C=O)—($C_1$–$C_6$)alkyl, ($C_1$–$C_6$)alkyl-O—(C=O)—($C_1$–$C_6$)alkyl, ($C_1$–$C_6$)alkyl-(C=O)—O—, ($C_1$–$C_6$)alkyl-(C=O)—O—($C_1$–$C_6$)alkyl, $H_2N$—(C=O)—, ($C_1$–$C_6$)alkyl-NH—(C=O)—, [($C_1$–$C_6$)alkyl]$_2$N—(C=O)—, $H_2N(C=O)$—($C_1$–$C_6$)alkyl, ($C_1$–$C_6$)alkyl-HN(C=O)—($C_1$–$C_6$)alkyl, [($C_1$–$C_6$)alkyl]$_2$N—(C=O)—($C_1$–$C_6$)alkyl, H(O=C)—NH—, ($C_1$–$C_6$)alkyl(C=O)—NH, ($C_1$–$C_6$)alkyl(C=O)—[NH]($C_1$–$C_6$)alkyl, $C_1$–$C_6$)alkyl(C=O)—[N($C_1$–$C_6$)alkyl]($C_1$–$C_6$)alkyl, phenoxy, and benzyloxy.

Other preferred compounds of formula I include those wherein $R^3$ is optionally substituted ($C_1$–$C_{10}$)alkyl, benzyl, pyranyl or ($C_3$–$C_{10}$)cycloalkyl-($CH_2$)$_n$—, wherein any of the carbon-carbon single bonds of said ($C_1$–$C_{10}$)alkyl may be optionally replaced by a carbon-carbon double bond; more preferably optionally substituted n-butyl, t-butyl, 2-methylpropyl, 2-methylbutyl, 3-methylbutyl, n-pentyl, 2-methyl-pentyl, allyl, cyclopentyl, cyclohexyl 2-methylcyclohexyl, cyclohexylmethyl, or cycloheptyl, more preferably wherein the substituent is fluoro, ($C_1$–$C_6$) alkyl or hydroxy.

Examples of specific preferred compounds of the formula I are the following:

7,8-difluoro-quinoline-3-carboxylic acid 1(S)-benzyl-2(S)-hydroxy-7-methyl-4(R)-methylcarbamoyl-octyl)-amide;

8-fluoro-quinoline-3-carboxylic acid 1(S)-benzyl-2(S)-hydroxy-7-methyl-4(R)-methylcarbamoyl-octyl)-amide;

quinoxaline-2-carboxylic acid [4(R)-carbamoyl-7-fluoro-1(S)-(3-fluoro-benzyl)-2(S)-hydroxy-7-methyl-octyl]-amide;

quinoxaline-2-carboxylic acid [4(R)-carbamoyl-1(S)-(2-fluoro-benzyl)-2(S)-hydroxy-7-methyl-octyl]-amide;

quinoxaline-2-carboxylic acid [1(S)-benzyl-4(S)-carbamoyl-4-(2,6-dimethyl-tetrahydro-pyran-4-yl)-2(S)-hydroxy-butyl]-amide;

quinoxaline-2-carboxylic acid [1(S)-benzyl-4(R)-carbamoyl-7-fluoro-2(S)-hydroxy-7-methyl-octyl)]-amide;

quinoxaline-2-carboxylic acid [1(S)-benzyl-5-cyclohexyl-2(S)-hydroxy-4(R)-methylcarbamoyl-pentyl)]-amide;

quinoxaline-2-carboxylic acid [1(S)-cyclohexylmethyl-2(S)-hydroxy-7-methyl-4(R)-methylcarbamoyl-octyl)]-amide;

quinoxaline-2-carboxylic acid [1(S)-benzyl-2(S)-hydroxy-4(S)-hydroxycarbamoyl-4-(1-hydroxy-4-methyl-cyclohexyl)-butyl]-amide;

quinoxaline-2-carboxylic acid [1(S)-benzyl-4(S)-(4,4-difluoro-1-hydroxy-cyclohexyl)-2(S)-(hydroxy4-hydroxycarbamoyl-butyl)]-amide;

quinoxaline-2-carboxylic acid [1(S)-benzyl-4(S)-carbamoyl-4(S)-(4,4-difluoro-cyclohexyl)-2(S)-hydroxy-butyl]-amide;

quinoline-3-carboxylic acid (1(S)-benzyl-4(S)-carbamoyl-4-cyclohexyl-2(S)-hydroxy-butyl)-amide;

quinoxaline-2-carboxylic acid (4(R)-carbamoyl-2(S)-hydroxy-7-methyl-1(S)-thiophen-2-ylmethyl-octyl)-amide;

quinoxaline-2-carboxylic acid [1(S)-benzyl-4(R)-carbamoyl-7-chloro-2(S)-hydroxy-oct-6-enyl)]-amide;

quinoxaline-2-carboxylic acid [1(S)-benzyl-4(R)-carbamoyl-2(S)-hydroxy-5-phenyl-pentyl)]-amide;
N-(1(S)-benzyl-4(R)-carbamoyl-7-fluoro-2(S)-hydroxy-7-methyl-octyl)-5,6-dichloro-nicotinamide;
quinoxaline-2-carboxylic acid (4(R)-carbamoyl-2(S)-hydroxy-7-methyl-1(S)-thiazol-4-ylmethyl-octyl)-amide;
benzothiazole-2-carboxylic acid [1(S)-benzyl-4(R)-carbamoyl-7-fluoro-2(S)-hydroxy-7-methyl-octyl)]-amide; and
benzofuran-2-carboxylic acid [1(S)-benzyl-4(R)-carbamoyl-7-fluoro-2(S)-hydroxy-7-methyl-octyl)]-amide.

Examples of Other Compounds of the Formula I are the Following:

quinoxaline-2-carboxylic acid (4-carbamoyl-7-fluoro-2-hydroxy-7-methyl-1-thiazol-4-ylmethyl-octyl)-amide;
quinoxaline-2-carboxylic acid (7-fluoro-2-hydroxy-4-hydroxycarbamoyl-7-methyl-1-thiazol-4-ylmethyl-octyl)-amide;
quinoxaline-2-carboxylic acid [4-carbamoyl-2-hydroxy4-(1-hydroxy-4-methyl-cyclohexyl)-1-thiazol-4-ylmethyl-butyl]-amide;
quinoxaline-2-carboxylic acid [2-hydroxy-4-hydroxycarbamoyl-4-(1-hydroxy-4-methyl-cyclohexyl)-1-thiazol-4-ylmethyl-butyl]-amide;
quinoxaline-2-carboxylic acid [4-carbamoyl-4-(4,4-difluoro-cyclohexyl)-2-hydroxy-1-thiazol-4-ylmethyl-butyl]-amide;
quinoxaline-2-carboxylic acid [4-(4,4-difluoro-cyclohexyl)-2-hydroxy-4-hydroxycarbamoyl-1-thiazol-4-ylmethyl-butyl]-amide;
quinoxaline-2-carboxylic acid [4-carbamoyl-1-(3,5-difluoro-benzyl)-7-fluoro-2-hydroxy-7-methyl-octyl]-amide;
quinoxaline-2-carboxylic acid [1-(3,5-difluoro-benzyl)-7-fluoro-2-hydroxy-4-hydroxycarbamoyl-7-methyl-octyl]-amide;
quinoxaline-2-carboxylic acid [4-carbamoyl-1-(3,5-difluoro-benzyl)-2-hydroxy-4-(1-hydroxy-4-methyl-cyclohexyl)-butyl]-amide;
quinoxaline-2-carboxylic acid [1(3,5-difluoro-benzyl)-2-hydroxy-4-hydroxycarbamoyl-4-(1-hydroxy-4-methyl-cyclohexyl)-butyl]-amide;
quinoxaline-2-carboxylic acid [4-carbamoyl-1-(3,5-difluoro-benzyl)4-(4,4-difluoro-cyclohexyl)-2-hydroxy-butyl]-amide;
quinoxaline-2-carboxylic acid [1-(3,5-difluoro-benzyl)4-(4,4-difluoro-cyclohexyl)-2-hydroxy-4-hydroxycarbamoyl-butyl]-amide;
quinoxaline-2-carboxylic acid (4-carbamoyl-2-hydroxy-7-methyl-1-pyridin-2-ylmethyl-octyl)-amide;
quinoxaline-2-carboxylic acid (7-fluoro-2-hydroxy-4-hydroxycarbamoyl-7-methyl-1-pyridin-2-ylmethyl-octyl)-amide;
quinoxaline-2-carboxylic acid [4-carbamoyl-4-(2,6-dimethyl-tetrahydro-pyran-4-yl)-2-hydroxy-1-pyridin-2-ylmethyl-butyl]-amide;
quinoxaline-2-carboxylic acid [2-hydroxy-4-hydroxycarbamoyl-4-(1-hydroxy-4-methyl-cyclohexyl)-1-pyridin-2-ylmethyl-butyl]-amide;
quinoxaline-2-carboxylic acid (4-carbamoyl-4-cyclohexyl-2-hydroxy-1-pyridin-2-ylmethyl-butyl)-amide;
quinoxaline-2-carboxylic acid [4-(4,4-difluoro-cyclohexyl)-2-hydroxy-4-hydroxycarbamoyl-1-pyridin-2-ylmethyl-butyl]-amide;
quinoxaline-2-carboxylic acid (4-carbamoyl-7-fluoro-2-hydroxy-7-methyl-1-pyridin-3-ylmethyl-octyl)-amide;
quinoxaline-2-carboxylic acid (2-hydroxy-4-hydroxycarbamoyl-7-methyl-1-pyridin-3-ylmethyl-octyl)-amide;
quinoxaline-2-carboxylic acid [4-carbamoyl-2-hydroxy-4-(1-hydroxy-4-methyl-cyclohexyl)-1-pyridin-3-ylmethyl-butyl]-amide;
quinoxaline-2-carboxylic acid [4-(2,6-dimethyl-tetrahydro-pyran-4-yl)-2-hydroxy-4-hydroxycarbamoyl-1-pyridin-3-ylmethyl-butyl]-amide;
quinoxaline-2-carboxylic acid [4-carbamoyl-4-(4,4-difluoro-cyclohexyl)-2-hydroxy-1-pyridin-3-ylmethyl-butyl]-amide;
quinoxaline-2-carboxylic acid (4-cyclohexyl-2-hydroxy-4-hydroxycarbamoyl-1-pyridin-3-ylmethyl-butyl)-amide;
quinoxaline-2-carboxylic acid [4-carbamoyl-7-fluoro-1-(4-fluoro-benzyl)-2-hydroxy-7-methyl-octyl]-amide;
quinoxaline-2-carboxylic acid [7-fluoro-1-(4-fluoro-benzyl)-2-hydroxy-4-hydroxycarbamoyl-7-methyl-octyl]-amide;
quinoxaline-2-carboxylic acid (4-carbamoyl-1-(4-fluoro-benzyl)-2-hydroxy-4-(1-hydroxy-4-methyl-cyclohexyl)-butyl]-amide;
quinoxaline-2-carboxylic acid [1-(4-fluoro-benzyl)-2-hydroxy-4-hydroxycarbamoyl-4-(1-hydroxy-4-methyl-cyclohexyl)-butyl]-amide;
quinoxaline-2-carboxylic acid [4-carbamoyl-4-(4,4-difluoro-cyclohexyl)-1-(4-fluoro-benzyl)-2-hydroxy-butyl]-amide;
quinoxaline-2-carboxylic acid [4-(4,4-difluoro-cyclohexyl)-1-(4-fluoro-benzyl)-2-hydroxy-4-hydroxycarbamoyl-butyl]-amide;
quinoxaline-2-carboxylic acid [4-carbamoyl-1-(3-fluoro-benzyl)-2-hydroxy-4-(1-hydroxy-cyclohexyl)-butyl]-amide;
quinoxaline-2-carboxylic acid [7-fluoro-1-(3-fluoro-benzyl)-2-hydroxy-4-hydroxycarbamoyl-7-methyl-octyl]-amide;
quinoxaline-2-carboxylic acid [4-carbamoyl-4-(2,6-dimethyl-tetrahydro-pyran-4-yl)-1-(3-fluoro-benzyl)-2-hydroxy-butyl]-amide;
quinoxaline-2-carboxylic acid [1-(3-fluoro-benzyl)-2-hydroxy-4-hydroxycarbamoyl-4-(1-hydroxy-4-methyl-cyclohexyl)-butyl]-amide;
quinoxaline-2-carboxylic acid [4-carbamoyl-4-(4,4-difluoro-cyclohexyl)-1-(3-fluoro-benzyl)-2-hydroxy-butyl]-amide;
quinoxaline-2-carboxylic acid [4-cyclohexyl-1-(3-fluoro-benzyl)-2-hydroxy-4-hydroxycarbamoyl-butyl]-amide;
quinoxaline-2-carboxylic acid [4-carbamoyl-1-(2-fluoro-benzyl)-2-hydroxy-4-(1-hydroxy-cyclohexyl)-butyl]-amide;
quinoxaline-2-carboxylic acid [7-fluoro-1-(2-fluoro-benzyl)-2-hydroxy-4-hydroxycarbamoyl-7-methyl-octyl]-amide;
quinoxaline-2-carboxylic acid [4-carbamoyl-4-(2,6-dimethyl-tetrahydro-pyran-4-yl)-1-(2-fluoro-benzyl)-2-hydroxy-butyl]-amide;
quinoxaline-2-carboxylic acid [1-(2-fluoro-benzyl)-2-hydroxy-4-hydroxycarbamoyl-4-(1-hydroxy-4-methyl-cyclohexyl)-butyl]-amide;
quinoxaline-2-carboxylic acid [4-carbamoyl-4-(4,4-difluoro-cyclohexyl)-1-(2-fluoro-benzyl)-2-hydroxy-butyl]-amide;
quinoxaline-2-carboxylic acid [4-cyclohexyl-1-(2-fluoro-benzyl)-2-hydroxy4-hydroxycarbamoyl-butyl]-amide;
quinoxaline-2-carboxylic acid (4-carbamoyl-7-fluoro-2-hydroxy-7-methyl-1-thiophen-2-ylmethyl-octyl)-amide;

quinoxaline-2-carboxylic acid (7-fluoro-2-hydroxy-4-hydroxycarbamoyl-7-methyl-1-thiophen-2-ylmethyl-octyl)-amide;
quinoxaline-2-carboxylic acid [4-carbamoyl-2-hydroxy4-(1-hydroxy-4-methyl-cyclohexyl)-1-thiophen-2-ylmethyl-butyl]-amide;
quinoxaline-2-carboxylic acid [2-hydroxy-4-hydroxycarbamoyl-4-(1-hydroxy-4-methyl-cyclohexyl)-1-thiophen-2-ylmethyl-butyl]-amide;
quinoxaline-2-carboxylic acid [4-carbamoyl-4-(4,4-difluoro-cyclohexyl)-2-hydroxy-1-thiophen-2-ylmethyl-butyl]-amide;
quinoxaline-2-carboxylic acid [4-(4,4-difluoro-cyclohexyl)-2-hydroxy-4-hydroxycarbamoyl-1-thiophen-2-ylmethyl-butyl]-amide;
quinoxaline-2-carboxylic acid [4-carbamoyl-2-hydroxy-7-methyl-1-(3-trifluoromethyl-benzyl)-octyl]-amide;
quinoxaline-2-carboxylic acid [7-fluoro-2-hydroxy-4-hydroxycarbamoyl-7-methyl-1-(3-trifluoromethyl-benzyl)-octyl]-amide;
quinoxaline-2-carboxylic acid [2-hydroxy-4-carbamoyl-4-(4-hydroxy-2,6-dimethyl-tetrahydro-pyran-4-yl)-1-(3-trifluoromethyl-benzyl)-butyl]-amide;
quinoxaline-2-carboxylic acid [2-hydroxy-4-hydroxycarbamoyl-4-( 1-hydroxy-4-methyl-cyclohexyl)-1-(3-trifluoromethyl-benzyl)-butyl]-amide;
quinoxaline-2-carboxylic acid {4-carbamoyl-4-cyclohexyl)-2-hydroxy-1-(3-trifluoromethyl-benzyl)-butyl}-amide;
quinoxaline-2-carboxylic acid {4-hydroxycarbamoyl-4-(4,4-difluoro-cyclohexyl)-2-hydroxy-1-(3-trifluoromethyl-benzyl)-butyl}-amide;
quinoxaline-2-carboxylic acid [7-fluoro-2-hydroxy-4-carbamoyl-7-methyl-1-(3-trifluoromethoxy-benzyl)-octyl]-amide;
quinoxaline-2-carboxylic acid [4-hydroxycarbamoyl-2-hydroxy-7-methyl-1-(3-trifluoromethoxy-benzyl)-octyl]-amide;
quinoxaline-2-carboxylic acid [2-hydroxy4-carbamoyl-4-(1-hydroxy-4-methyl-cyclohexyl)-1-(3-trifluoromethoxy-benzyl)-butyl]-amide;
quinoxaline-2-carboxylic acid [2-hydroxy4-hydroxycarbamoyl-4-(4-hydroxy-2,6-dimethyl-tetrahydro-pyran-4-yl)-1-(3-trifluoromethoxy-benzyl)-butyl]-amide;
quinoxaline-2-carboxylic acid {4-carbamoyl-4-(4,4-difluoro-cyclohexyl)-2-hydroxy-1-(3-trifluoromethoxy-benzyl)-butyl}-amide;
quinoxaline-2-carboxylic acid {4-hydroxycarbamoyl-4-cyclohexyl)-2-hydroxy-1-(3-trifluoromethoxy-benzyl)-butyl}-amide;
quinoxaline-2-carboxylic acid [7-fluoro-2-hydroxy-4-carbamoyl-7-methyl-1-(4-trifluoromethoxy-benzyl)-octyl]-amide;
quinoxaline-2-carboxylic acid [7-fluoro-2-hydroxy-4-hydroxycarbamoyl-7-methyl-1-(4-trifluoromethoxy-benzyl)-octyl]-amide;
quinoxaline-2-carboxylic acid [2-hydroxy-4-carbamoyl-4-(1-hydroxy-4-methyl-cyclohexyl)-1-(4-trifluoromethoxy-benzyl)-butyl]-amide;
quinoxaline-2-carboxylic acid [2-hydroxy-4-hydroxycarbamoyl-4-(1-hydroxy-4-methyl-cyclohexyl)-1-(4-trifluoromethoxy-benzyl)-butyl]-amide;
quinoxaline-2-carboxylic acid {4-carbamoyl-4-(4,4-difluoro-cyclohexyl)-2-hydroxy-1-(4-trifluoromethoxy-benzyl)-butyl}-amide;
quinoxaline-2-carboxylic acid {4-hydroxycarbamoyl-4-(4,4-difluoro-cyclohexyl)-2-hydroxy-1-(4-trifluoromethoxy-benzyl)-butyl}-amide;
quinoxaline-2-carboxylic acid [4-carbamoyl-2-hydroxy-7-methyl-1-(2-trifluoromethyl-benzyl)-octyl]-amide;
quinoxaline-2-carboxylic acid [7-fluoro-2-hydroxy-4-hydroxycarbamoyl-7-methyl-1-(2-trifluoromethoxy-benzyl)-octyl]-amide;
quinoxaline-2-carboxylic acid [2-hydroxy-4-carbamoyl-4-(4-hydroxy-2,6-dimethyl-tetrahydro-pyran-4-yl)-1-(2-trifluoromethoxy-benzyl)-butyl]-amide;
quinoxaline-2-carboxylic acid [2-hydroxy-4-hydroxycarbamoyl-4-(1-hydroxy4-methyl-cyclohexyl)-1-(2-trifluoromethoxy-benzyl)-butyl]-amide;
quinoxaline-2-carboxylic acid {4-carbamoyl-4-cyclohexyl)-2-hydroxy-1-(2-trifluoromethoxy-benzyl)-butyl}-amide;
quinoxaline-2-carboxylic acid {4-hydroxycarbamoyl-4-(4,4-difluoro-cyclohexyl)-2-hydroxy-1-(2-trifluoromethoxy-benzyl)-butyl}-amide;
quinoxaline-2-carboxylic acid [7-fluoro-2-hydroxy-4-carbamoyl-7-methyl-1-[3-(1-hydroxy-1-methyl-ethyl)-benzyl]-octyl]-amide;
quinoxaline-2-carboxylic acid [4-hydroxycarbamoyl-2-hydroxy-7-methyl-1-[3-(1-hydroxy-1-methyl-ethyl)-benzyl]-octyl]-amide;
quinoxaline-2-carboxylic acid [2-hydroxy-4-carbamoyl-4-(1-hydroxy-4-methyl-cyclohexyl)-1-[3-(1-hydroxy-1-methyl-ethyl)-benzyl]-butyl]-amide;
quinoxaline-2-carboxylic acid [2-hydroxy-4-hydroxycarbamoyl-4-(4-hydroxy-2,6-dimethyl-tetrahydro-pyran-4-yl)-1-3-(1-hydroxy-1-methyl-ethyl)-benzyl]-butyl]-amide;
quinoxaline-2-carboxylic acid {4-carbamoyl-4-(4,4-difluoro-cyclohexyl)-2-hydroxy-1-[3-(1-hydroxy-1-methyl-ethyl)-benzyl]-butyl}-amide;
quinoxaline-2-carboxylic acid {4-hydroxycarbamoyl-4-(cyclohexyl)-2-hydroxy-1-[3-(1-hydroxy-1-methyl-ethyl)-benzyl]-butyl}-amide;
quinoxaline-2-carboxylic acid [7-fluoro-2-hydroxy-4-carbamoyl-7-methyl-1-thiophen-3-ylmethyl-butyl]-amide;
quinoxaline-2-carboxylic acid [7-fluoro-2-hydroxy-4-hydroxycarbamoyl-7-methyl-1-thiophen-3-ylmethyl-butyl]-amide;
quinoxaline-2-carboxylic acid [2-hydroxy-4-carbamoyl-4-(1-hydroxy4-methyl-cyclohexyl)-1-thiophen-3-ylmethyl-butyl]-amide;
quinoxaline-2-carboxylic acid [2-hydroxy-4-hydroxycarbamoyl-4-(1-hydroxy-4-methyl-cyclohexyl)-1-thiophen-3-ylmethyl-butyl]-amide;
quinoxaline-2-carboxylic acid [4-carbamoyl-4-(4,4-difluoro-cyclohexyl)-2-hydroxy-1-thiophen-3-ylmethyl-butyl]-amide;
quinoxaline-2-carboxylic acid [4-hydroxycarbamoyl4-(4,4-difluoro-cyclohexyl)-2-hydroxy-1-thiophen-3-ylmethyl-butyl]-amide;
[[1,8]naphthyridine-3-carboxylic acid (1-benzyl-4-carbamoyl-7-fluoro-2-hydroxy-7-methyl-octyl)-amide;
[1,8]naphthyridine-3-carboxylic acid (1-benzyl-7-fluoro-2-hydroxy-4-hydroxycarbamoyl-7-methyl-octyl)-amide;
[1,8]naphthyridine-3-carboxylic acid [1-benzyl-4-carbamoyl-2-hydroxy-4-(1-hydroxy-4-methyl-cyclohexyl)-butyl]-amide;
[1,8]naphthyridine-3-carboxylic acid [1-benzyl-2-hydroxy-4-hydroxycarbamoyl-4-(1-hydroxy-4-methyl-cyclohexyl)-butyl]-amide;
[1,5]naphthyridine-3-carboxylic acid (1-benzyl-4-carbamoyl-7-fluoro-2-hydroxy-7-methyl-octyl)-amide;
[1,5]naphthyridine-3-carboxylic acid (1-benzyl-7-fluoro-2-hydroxy-4-hydroxycarbamoyl-7-methyl-octyl)-amide;

[1,5]naphthyridine-3-carboxylic acid [1-benzyl-4-carbamoyl-2-hydroxy-4-(1-hydroxy-4-methyl-cyclohexyl)-butyl]-amide;
[1,5]naphthyridine-3-carboxylic acid [1-benzyl-2-hydroxy-4-hydroxycarbamoyl-4-(1-hydroxy-4-methyl-cyclohexyl)-butyl]-amide;
[1,8]naphthyridine-2-carboxylic acid (1-benzyl-4-carbamoyl-7-fluoro-2-hydroxy-7-methyl-octyl)-amide;
[1,8]naphthyridine-2-carboxylic acid (1-benzyl-7-fluoro-2-hydroxy-4-hydroxycarbamoyl-7-methyl-octyl)-amide;
[1,8]naphthyridine-2-carboxylic acid [1-benzyl-4-carbamoyl-2-hydroxy-4-(1-hydroxy-4-methyl-cyclohexyl)-butyl]-amide;
[1,8]naphthyridine-2carboxylic acid [1-benzyl-2-hydroxy-4-hydroxycarbamoyl-4-(1-hydroxy-4-methyl-cyclohexyl)-butyl]-amide;
[1,6]naphthyridine-2-carboxylic acid (1-benzyl-4-carbamoyl-7-fluoro-2-hydroxy-7-methyl-octyl)-amide;
[1,6]naphthyridine-2-carboxylic acid (1-benzyl-7-fluoro-2-hydroxy-4-hydroxycarbamoyl-7-methyl-octyl)-amide;
[1,6]naphthyridine-2-carboxylic acid [1-benzyl-4-carbamoyl-2-hydroxy-4-(1-hydroxy-4-methyl-cyclohexyl)-butyl]-amide;
[1,6]naphthyridine-2-carboxylic acid [1-benzyl-2-hydroxy-4-hydroxycarbamoyl-4-(1-hydroxy-4-methyl-cyclohexyl)-butyl]-amide;
quinoline-3-carboxylic acid 1(S)-cyclohexylmethyl-2(S)-hydroxy-6-methyl-4(R)-methylcarbamoyl-heptyl)-amide;
quinoxaline-2-carboxylic acid 1(S)-cyclohexylmethyl-2(S)-hydroxy-6-methyl-4(R)-methylcarbamoyl-heptyl)-amide;
quinoxaline-2-carboxylic acid (6-chloro-1(S)-cyclohexylmethyl-2(S)-hydroxy4(S)-methylcarbamoyl-hept-6-enyl)-amide;
quinoline-3-carboxylic acid (2(S)-hydroxy-1(S)-isobutyl-6-methyl-4(R)-methylcarbamoyl-heptyl)-amide;
quinoxaline-2-carboxylic acid 1(S)-sec-butyl-2(S)-hydroxy-6-methyl-4(R)-methylcarbamoyl-heptyl)-amide;
quinoline-3-carboxylic acid 1(S)-cyclohexylmethyl-2(S)-hydroxy-6-methyl-4(R)-methylcarbamoyl-hept-6-enyl)-amide;
quinoxaline-2-carboxylic acid 1(S)-cyclohexylmethyl-2(S)-hydroxy-6-methyl-4(R)-methylcarbamoyl-hept-6-enyl)-amide;
N-1(S)-cyclohexylmethyl-2(S)-hydroxy-6-methyl-4(R)-methylcarbamoyl-heptyl)-5-phenyl-nicotinamide;
quinoline-3-carboxylic acid 1(S)-benzyl-2(S)-hydroxy-6-methyl-4(R)-methylcarbamoyl-heptyl)-amide;
quinoxaline-2-carboxylic acid 1(S)-cyclohexylmethyl-4(R)-dimethylcarbamoyl-2(S)-hydroxy-6-methyl-hept-6-enyl)-amide;
quinoline-3-carboxylic acid 1(S)-cyclohexylmethyl-2(S)-hydroxy-6-methyl-4(R)-methylcarbamoyl-heptyl)-amide;
quinoxaline-2-carboxylic acid 1(S)-cyclohexylmethyl-2(S)-hydroxy-6-methyl-4(R)-methylcarbamoyl-heptyl)-amide;
isoquinoline-4(R)-carboxylic acid 1(S)-cyclohexylmethyl-2(S)-hydroxy-6-methyl-4(R)-methylcarbamoyl-heptyl)-amide;
quinoline-3-carboxylic acid (4(R)-carbamoyl-1(S)-cyclohexylmethyl-2(S)-hydroxy-6-methyl-heptyl)-amide;
quinoline-3-carboxylic acid (5-cyclohexyl-1(S)-cyclohexylmethyl-2(S)-hydroxy-4(R)-methylcarbamoyl-pentyl)-amide;
quinoline-3-carboxylic acid 1(S)-cyclohexylmethyl-2(S)-hydroxy-6-methyl-4(R)-methylcarbamoyl-heptyl)-amide;
quinoline-3-carboxylic acid 1(S)-cyclohexylmethyl-2(S)-hydroxy-6-methyl-4(S)-methylcarbamoyl-heptyl)-amide;
quinoline-3-carboxylic acid 1(S)-cyclohexylmethyl-2(S)-hydroxy-4(R)-methylcarbamoyl-5-phenyl-pentyl)-amide;
quinoxaline-2-carboxylic acid 1(S)-cyclohexylmethyl-2(S)-hydroxy-4(R)-methylcarbamoyl-5-phenyl-pentyl)-amide;
quinoline-3-carboxylic acid 1(S)-benzyl-4(R)-butylcarbamoyl-2(S)-hydroxy-6-methyl- heptyl)-amide;
quinoline-3-carboxylic acid 1(S)-benzyl-4(R)-cyclobutylcarbamoyl-2(S)-hydroxy-6-methyl-heptyl)-amide;
quinoline-3-carboxylic acid 1(S)-benzyl-4(R)-benzylcarbamoyl-2(S)-hydroxy-6-methyl-heptyl)-amide;
quinoline-3-carboxylic acid 1(S)-benzyl-4(R)-cyclopropylcarbamoyl-2(S)-hydroxy-6-methyl-heptyl)-amide;
quinoline-3-carboxylic acid 1(S)-benzyl-2(S)-hydroxy-6-methyl-4(S)-methylcarbamoyl-heptyl)-amide;
quinoline-3-carboxylic acid 1(S)-benzyl-4(R)-ethylcarbamoyl-2(S)-hydroxy-6-methyl-heptyl)-amide;
quinoline-3-carboxylic acid 1(S)-benzyl-2(S)-hydroxy-6-methyl-4(R)-propylcarbamoyl-heptyl)-amide;
quinoline-3-carboxylic acid [1-benzyl-2(S)-hydroxy-4(R)-(2(S)-hydroxy-ethylcarbamoyl)-6-methyl-heptyl]-amide;
cinnoline-4(R)-carboxylic acid 1(S)-benzyl-2(S)-hydroxy-6-methyl-4(R)-methylcarbamoyl-heptyl)-amide;
isoquinoline-4(R)-carboxylic acid 1(S)-benzyl-2(S)-hydroxy-6-methyl-4(R)-methylcarbamoyl-heptyl)-amide;
quinoxaline-2-carboxylic acid 1(S)-benzyl-2(S)-hydroxy-6-methyl-4(R)-methylcarbamoyl-heptyl)-amide;
N-1(S)-Benzyl-2(S)-hydroxy-6-methyl-4(R)-methylcarbamoyl-heptyl)-5-bromo-nicotinamide;
quinoline-3-carboxylic acid 1(R)-cyclohexylmethyl-2(R)-hydroxy-6-methyl-4(S)-methylcarbamoyl-heptyl)-amide;
quinoxaline-2-carboxylic acid [1-(4-benzyloxy-benzyl)-2(S)-hydroxy-6-methyl-4(R)-methylcarbamoyl-heptyl]-amide;
quinoline-3-carboxylic acid [1-(4-benzyloxy-benzyl)-2(S)-hydroxy-6-methyl-4(R)-methylcarbamoyl-heptyl]-amide;
isoquinoline-1-carboxylic acid 1(S)-benzyl-2(S)-hydroxy-6-methyl-4(R)-methylcarbamoyl-heptyl)-amide;
quinoline-4(R)-carboxylic acid 1(S)-benzyl-2(S)-hydroxy-6-methyl-4(R)-methylcarbamoyl-heptyl)-amide;
quinoline-6-carboxylic acid 1(S)-benzyl-2(S)-hydroxy-6-methyl-4(R)-methylcarbamoyl-heptyl)-amide;
quinoline-3-carboxylic acid [2(S)-hydroxy-1-(4-hydroxy-benzyl)-6-methyl-4(R)-methylcarbamoyl-heptyl]-amide;
quinoline-2-carboxylic acid 1(S)-benzyl-2(S)-hydroxy-6-methyl-4(R)-methylcarbamoyl-heptyl)-amide;
naphthalene-2-carboxylic acid 1(S)-benzyl-2(S)-hydroxy-6-methyl-4(R)-methylcarbamoyl-heptyl)-amide;
quinoline-3-carboxylic acid 1(S)-benzyl-5-cyclohex-1-enyl-2(S)-hydroxy-4(R)-methylcarbamoyl-pentyl)-amide;
quinoline-3-carboxylic acid [1-benzyl-2(S)-hydroxy-6-methyl-4(R)-(3-methyl-butylcarbamoyl)-heptyl]-amide;
quinoxaline-2-carboxylic acid 1(S)-benzyl-2(S)-hydroxy-6-methyl-4(S)-methylcarbamoyl-heptyl)-amide;
trifluoro-methanesulfonic acid 4-{3(S)-hydroxy-7-methyl-5(R)-methylcarbamoyl-2(S)-[(quinoline-3-carbonyl)-amino]-octyl}-phenyl ester;
trifluoro-methanesulfonic acid 4-{3(S)-hydroxy-7-methyl-5(R)-methylcarbamoyl-2(S)-[(quinoxaline-2-carbonyl)-amino]-octyl}-phenyl ester;
quinoline-3-carboxylic acid 1(S)-benzyl-5-cyclohexyl-2(S)-hydroxy-4(R)-methylcarbamoyl-pentyl)-amide;
quinoxaline-2-carboxylic acid 1(S)-benzyl-5-cyclohexyl-2(S)-hydroxy-4(R)-methylcarbamoyl-pentyl)-amide;
isoquinoline-3-carboxylic acid 1(S)-benzyl-5-cyclohexyl-2(S)-hydroxy-4(R)-methylcarbamoyl-pentyl)-amide;

N-1(S)-benzyl-5-cyclohexyl-2(S)-hydroxy-4(R)-methylcarbamoyl-pentyl)-5-bromo-nicotinamide;
quinoline-3-carboxylic acid 1(S)-benzyl-2(S)-hydroxy-6-methyl-4(R)-prop-2-ynylcarbamoyl-heptyl)-amide;
quinoline-3-carboxylic acid 1(S)-cyclohexylmethyl-2(S)-hydroxy-4(R)-hydroxycarbamoyl-6-methyl-heptyl)-amide;
quinoline-3-carboxylic acid 2(S)-hydroxy-1(S)-(4-methoxy-benzyl)-6-methyl-4(R)-methylcarbamoyl-heptyl]-amide;
isoquinoline-3-carboxylic acid (5-cyclohexyl-1(S)-cyclohexylmethyl-2(S)-hydroxy-4(R)-methylcarbamoyl-pentyl)-amide;
5-bromo-N-(5-cyclohexyl-1(S)-cyclohexylmethyl-2(S)-hydroxy-4(R)-methylcarbamoyl-pentyl)-nicotinamide;
quinoxaline-2-carboxylic acid [2(S)-hydroxy-1(S)-(4-methoxy-benzyl)-6-methyl-4(R)-methylcarbamoyl-heptyl]-amide;
isoquinoline-4(R)-carboxylic acid (5-cyclohexyl-1(S)-cyclohexylmethyl-2(S)-hydroxy-4(R)-methylcarbamoyl-pentyl)-amide;
quinoline-2-carboxylic acid 1(S)-benzyl-5-cyclohexyl-2(S)-hydroxy-4(R)-methylcarbamoyl-pentyl)-amide;
isoquinoline-4(R)-carboxylic acid 1(S)-benzyl-5-cyclohexyl-2(S)-hydroxy-4(R)-methylcarbamoyl-pentyl)-amide;
quinoxaline-2-carboxylic acid [2(S)-hydroxy-1(S)-(4-hydroxy-benzyl)-6-methyl-4(R)-methylcarbamoyl-heptyl]-amide;
quinoxaline-2-carboxylic acid (5-cyclohexyl-1(S)-cyclohexylmethyl-2(S)-hydroxy-4(R)-methylcarbamoyl-pentyl)-amide;
quinoline-3-carboxylic acid [1(S)-(4-chloro-benzyl)-2(S)-hydroxy-6-methyl-4(R)-methylcarbamoyl-heptyl]-amide;
quinoxaline-2-carboxylic acid [1(S)-(4-chloro-benzyl)-2(S)-hydroxy-6-methyl-4(R)-methylcarbamoyl-heptyl]-amide;
quinoline-3-carboxylic acid 1(S)-cyclohexylmethyl-2(S)-hydroxy-7-methyl-4(R)-methylcarbamoyl-octyl)-amide;
quinoxaline-2-carboxylic acid 1(S)-cyclohexylmethyl-2(S)-hydroxy-7-methyl-4(R)-methylcarbamoyl-octyl)-amide;
quinoline-3-carboxylic acid [1(S)-(4-chloro-benzyl)-5-cyclohexyl-2(S)-hydroxy-4(R)-methylcarbamoyl-pentyl]-amide;
quinoxaline-2-carboxylic acid [1(S)-(4-chloro-benzyl)-5-cyclohexyl-2(S)-hydroxy-4(R)-methylcarbamoyl-pentyl]-amide;
quinoline-2-carboxylic acid [1(S)-(4-chloro-benzyl)-5-cyclohexyl-2(S)-hydroxy-4(R)-methylcarbamoyl-pentyl]-amide;
benzofuran-2-carboxylic acid 1(S)-benzyl-2(S)-hydroxy-6-methyl-4(R)-methylcarbamoyl-heptyl)-amide;
N-1(S)-benzyl-2(S)-hydroxy-6-methyl-4(R)-methylcarbamoyl-heptyl)-5,6-dichloro-nicotinamide;
quinoline-3-carboxylic acid 1(S)-benzyl-2(S)-hydroxy-7-methyl-4(R)-methylcarbamoyl-octyl)-amide;
N-1(S)-benzyl-2(S)-hydroxy-7-methyl-4(R)-methylcarbamoyl-octyl)-5-bromo-nicotinamide;
5,6,7,8-tetrahydro-quinoline-3-carboxylic acid 1(S)-benzyl-2(S)-hydroxy-6-methyl-4(R)-methylcarbamoyl-heptyl)-amide;
quinoxaline-2-carboxylic acid 1(S)-benzyl-2(S)-hydroxy-7-methyl-4(R)-methylcarbamoyl-octyl)-amide;
quinoline-2-carboxylic acid 1(S)-benzyl-2(S)-hydroxy-7-methyl-4(R)-methylcarbamoyl-octyl)-amide;
isoquinoline4(R)-carboxylic acid 1(S)-benzyl-2(S)-hydroxy-7-methyl-4(R)-methylcarbamoyl-octyl)-amide;
quinoxaline-2-carboxylic acid [1-(3,4-dichloro-benzyl)-2(S)-hydroxy-6-methyl-4(R)-methylcarbamoyl-heptyl]-amide;
benzo[b]thiophene-2-carboxylic acid 1(S)-benzyl-2(S)-hydroxy-6-methyl-4(R)-methylcarbamoyl-heptyl)-amide;
2-methyl-quinoline-3-carboxylic acid 1(S)-benzyl-2(S)-hydroxy-6-methyl-4(R)-methylcarbamoyl-heptyl)-amide;
6,7-dimethoxy-quinoline-3-carboxylic acid 1(S)-benzyl-2(S)-hydroxy-6-methyl-4(R)-methylcarbamoyl-heptyl)-amide;
6,7-difluoro-quinoline-3-carboxylic acid 1(S)-benzyl-2(S)-hydroxy-6-methyl-4(R)-methylcarbamoyl-heptyl)-amide;
1H-benzoimidazole-2-carboxylic acid 1(S)-benzyl-2(S)-hydroxy-6-methyl-4(R)-methylcarbamoyl-heptyl)-amide;
5-methyl-pyrazine-2-carboxylic acid 1(S)-benzyl-2(S)-hydroxy-6-methyl-4(R)-methylcarbamoyl-heptyl)-amide;
quinoline-3-carboxylic acid [1(S)-(4-fluoro-benzyl)-2(S)-hydroxy-6-methyl-4(R)-methylcarbamoyl-heptyl]-amide;
quinoxaline-2-carboxylic acid [1(S)-(4-fluoro-benzyl)-2(S)-hydroxy-6-methyl-4(R)-methylcarbamoyl-heptyl]-amide;
5-chloro-1H-indole-2-carboxylic acid 1(S)-benzyl-2(S)-hydroxy-6-methyl-4(R)-methylcarbamoyl-heptyl)-amide;
quinoxaline-2-carboxylic acid 1(S)-benzyl-4(R)-carbamoyl-2(S)-hydroxy-7-methyl-octyl)-amide;
2-methoxy-quinoline-3-carboxylic acid 1(S)-benzyl-2(S)-hydroxy-6-methyl-4(R)-methylcabamoyl-heptyl)-amide;
5,6-dichloro-1H-benzoimidazole-2-carboxylic acid 1(S)-benzyl-2(S)-hydroxy-6-methyl-4(R)-methylcarbamoyl-heptyl)-amide;
benzothiazole-2-carboxylic acid 1(S)-benzyl-2(S)-hydroxy-6-methyl-4(R)-methylcarbamoyl-heptyl)-amide;
7,8-difluoro-quinoline-3-carboxylic acid 1(S)-benzyl-2(S)-hydroxy-6-methyl-4(R)-methylcarbamoyl-heptyl)-amide;
6,7,8-trifluoro-quinoline-3-carboxylic acid 1(S)-benzyl-2(S)-hydroxy-6-methyl-4(R)-methylcarbamoyl-heptyl)-amide;
5,8-dimethyl-quinoline-3-carboxylic acid 1(S)-benzyl-2(S)-hydroxy-6-methyl-4(R)-methylcarbamoyl-heptyl)-amide;
quinoxaline-2-carboxylic acid 1(S)-benzyl-4(R)-butylcarbamoyl-2(S)-hydroxy-7-methyl-octyl)-amide;
quinoline-3-carboxylic acid [1(S)-(3,4-dichloro-benzyl)-2(S)-hydroxy-6-methyl-4(R)-methylcarbamoyl-heptyl]-amide;
5,6,7,8-tetrahydro-quinoline-3-carboxylic acid 1(S)-benzyl-2(S)-hydroxy-7-methyl-4(R)-methylcarbamoyl-octyl)-amide;
quinoline-3-carboxylic acid 1(S)-benzyl-5-cyclopentyl-2(S)-hydroxy-4(R)-methylcarbamoyl-pentyl)-amide;
quinoxaline-2-carboxylic acid 1(S)-benzyl-5-cyclopentyl-2(S)-hydroxy-4(R)-methylcarbamoyl-pentyl)-amide;
N-1(S)-benzyl-5-cyclopentyl-2(S)-hydroxy-4(R)-methylcarbamoyl-pentyl)-5-bromo-nicotinamide;
5,6,7,8-tetrahydro-quinoline-3-carboxylic acid 1(S)-benzyl-5-cyclopentyl-2(S)-hydroxy-4(R)-methylcarbamoyl-pentyl)-amide;
quinoxaline-2-carboxylic acid 1(S)-benzyl-4(R)-carbamoyl-5-cyclopentyl-2(S)-hydroxy-pentyl)-amide;
6,7-dihydro-5H-[1]pyrindine-3-carboxylic acid 1(S)-benzyl-2(S)-hydroxy-7-methyl-4(R)-methylcarbamoyl-octyl)-amide;
quinoxaline-2-carboxylic acid [1(S)-(4,4-difluoro-cyclohexylmethyl)-2(S)-hydroxy-6-methyl-4(R)-methylcarbamoyl-heptyl]-amide;
quinoxaline-2-carboxylic acid [1(S)-(4,4-difluoro-cyclohexylmethyl)-2(S)-hydroxy-7-methyl-4(R)-methylcarbamoyl-octyl]-amide;
quinoxaline-2-carboxylic acid 1(S)-benzyl-4(R)-ethylcarbamoyl-2(S)-hydroxy-7-methyl-octyl)-amide;
quinoxaline-2-carboxylic acid 1(S)-benzyl-2(S)-hydroxy-7-methyl-4(R)-propylcarbamoyl-octyl)-amide;

quinoxaline-2-carboxylic acid 1(S)-benzyl-4(R)-cyclopropylcarbamoyl-2(S)-hydroxy-7-methyl-octyl)-amide;

quinoxaline-2-carboxylic acid 1(S)-benzyl-4(R)-cyclobutylcarbamoyl-2(S)-hydroxy-7-methyl-octyl)-amide;

quinoxaline-2-carboxylic acid [1(S)-(4-difluoromethoxy-benzyl)-2(S)-hydroxy-7-methyl-4(R)-methylcarbamoyl-octyl]-amide;

4-{3(S)-hydroxy-7-methyl-5(R)-methylcarbamoyl-2(S)-[(quinoxaline-2-carbonyl)-amino]-octyl}-benzoic acid methyl ester;

quinoxaline-2-carboxylic acid 1(S)-benzyl-4(R)-carbamoyl-2(S)-hydroxy-butyl)-amide;

6,7,8-trifluoro-quinoline-3-carboxylic acid 1(S)-benzyl-2(S)-hydroxy-7-methyl-4(R)-methylcarbamoyl-octyl)-amide;

6,7,8-trifluoro-quinoline-3-carboxylic acid 1(S)-benzyl-4(R)-carbamoyl-2(S)-hydroxy-7-methyl-octyl)-amide;

6,8-difluoro-quinoline-3-carboxylic acid 1(S)-benzyl-2(S)-hydroxy-7-methyl-4(R)-methylcarbamoyl-octyl)-amide;

6,8-difluoro-quinoline-3-carboxylic acid 1(S)-benzyl-4(R)-carbamoyl-2(S)-hydroxy-7-methyl-octyl)-amide;

quinoxaline-2-carboxylic acid 1(S)-benzyl-4(R)-butylcarbamoyl-5-cyclopentyl-2(S)-hydroxy-pentyl)-amide;

6-methyl-pyridine-2-carboxylic acid 1(S)-benzyl-2(S)-hydroxy-6-methyl-4(R)-methylcarbamoyl-heptyl)-amide;

quinoxaline-2-carboxylic acid 1(S)-benzyl-2(S)-hydroxy-8-methyl-4(R)-methylcarbamoyl-nonyl)-amide;

quinoxaline-2-carboxylic acid 1(S)-benzyl-4(R)-carbamoyl-2(S)-hydroxy-8-methyl-nonyl)-amide;

quinoxaline-2-carboxylic acid 1(S)-biphenyl-4(R)-ylmethyl-2(S)-hydroxy-7-methyl-4(R)-methylcarbamoyl-octyl)-amide;

quinoxaline-2-carboxylic acid 1(S)-benzyl4(R)-carbamoyl-2(S)-hydroxy-7-methyl-oct-6-enyl)-amide;

quinoxaline-2-carboxylic acid (2(S)-hydroxy-6-methyl-4(R)-methylcarbamoyl-1(S)-naphthalen-2-ylmethyl-heptyl)-amide;

quinoxaline-2-carboxylic acid 1(S)-benzyl-4(R)-carbamoyl-2(S)-hydroxy-7,7-dimethyl-octyl)-amide;

quinoxaline-2-carboxylic acid 1(S)-benzyl-2(S)-hydroxy-7,7-dimethyl-4(R)-methylcarbamoyl-octyl)-amide;

quinoxaline-2-carboxylic acid 1(S)-benzyl-4(R)-carbamoyl-2(S)-hydroxy-5-phenyl-pentyl)-amide;

quinoxaline-2-carboxylic acid 1(S)-biphenyl4(R)-ylmethyl-4(R)-carbamoyl-2(S)-hydroxy-7-methyl-octyl)-amide;

quinoxaline-2-carboxylic acid [1(S)-benzyl-5-(4,4-difluoro-cyclohexyl)-2(S)-hydroxy-4(R)-methylcarbamoyl-pentyl]-amide;

quinoxaline-2-carboxylic acid [1(S)-benzyl-4(R)-carbamoyl-5-(4,4-difluoro-cyclohexyl)-2(S)-hydroxy-pentyl]-amide;

quinoxaline-2-carboxylic acid [1(S)-(3-fluoro-benzyl)-2(S)-hydroxy-7-methyl-4(R)-methylcarbamoyl-octyl]-amide;

quinoxaline-2-carboxylic acid [4(R)-carbamoyl-1(S)-(3(S)-fluoro-benzyl)-2(S)-hydroxy-7-methyl-octyl]-amide;

quinoxaline-2-carboxylic acid 1(S)-benzyl-2(S)-hydroxy-7-methyl-4(R)-40methylcarbamoyl-oct-6-enyl)-amide;

6,7,8-trifluoro-quinoline-3-carboxylic acid 1(S)-benzyl-2(S)-hydroxy-7-methyl-4(R)-methylcarbamoyl-nonyl)-amide;

quinoxaline-2-carboxylic acid 1(S)-benzyl-4(R)-carbamoyl-2(S)-hydroxy-7-methyl-nonyl)-amide;

quinoxaline-2-carboxylic acid 1(S)-benzyl-7-fluoro-2(S)-hydroxy-7-methyl-4(R)-methylcarbamoyl-octyl)-amide;

quinoxaline-2-carboxylic acid 1(S)-benzyl-4(R)-carbamoyl-7-fluoro-2(S)-hydroxy-7-methyl-octyl)-amide;

quinoxaline-2-carboxylic acid 1(S)-benzyl-2(S)-hydroxy-7-methyl-4(R)-methylcarbamoyl-nonyl)-amide;

quinoxaline-2-carboxylic acid 1(S)-benzyl-4(R)-dimethylcarbamoyl-2(S)-hydroxy-7-methyl-octyl)-amide;

7,8-difluoro-quinoline-3-carboxylic acid 1(S)-benzyl-2(S)-hydroxy-4(R)-methylcarbamoyl-5-phenyl-pentyl)-amide;

7,8-difluoro-quinoline-3-carboxylic acid 1(S)-benzyl-2(S)-hydroxy-7-methyl-4(R)-methylcarbamoyl-octyl)-amide;

8-fluoro-quinoline-3-carboxylic acid 1(S)-benzyl-2(S)-hydroxy-7-methyl-4(R)-methylcarbamoyl-octyl)-amide;

quinoxaline-2-carboxylic acid 1(S)-benzyl-2(S)-hydroxy-4(R)-methylcarbamoyl-non-6-enyl)-amide;

quinoxaline-2-carboxylic acid 1(S)-benzyl-4(R)-carbamoyl-2(S)-hydroxy-non-6-enyl)-amide;

7,8difluoro-quinoline-3-carboxylic acid 1(S)-benzyl-4(R)-carbamoyl-2(S)-hydroxy-7-methyl-octyl)-amide;

8-fluoro-quinoline-3-carboxylic acid 1(S)-benzyl-4(R)-carbamoyl-2(S)-hydroxy-7-methyl-octyl)-amide;

4(S)hydroxy-2(R)-(3-methyl-butyl)-6-phenyl-5(S)-[(quinoxaline-2(R)-carbonyl)-amino]-hexanoic acid;

quinoxaline-2-carboxylic acid 1(S)-benzyl-4(R)-carbamoyl-2(S)-hydroxy-nonyl)-amide;

2-{2(S)-hydroxy-4-phenyl-3(S)-[(quinoxaline-2-carbonyl)-amino]-butyl}-N1,N4-dimethyl-succinamide;

quinoxaline-2-carboxylic acid 1(S)-benzyl-4-ethylcarbamoyl-7-fluoro-2(S)-hydroxy-7-methyl-octyl)-amide;

quinoxaline-2-carboxylic acid 1(S)-benzyl-4(R)-butylcarbamoyl-7-fluoro-2(S)-hydroxy-7-methyl-octyl)-amide;

quinoxaline-2-carboxylic acid [7-fluoro-1(S)-(4-fluoro-benzyl)-2(S)-hydroxy-7-methyl-4(R)-methylcarbamoyl-octyl]-amide;

quinoxaline-2-carboxylic acid [4(R)-carbamoyl-1(S)-(3,4-dichloro-benzyl)-7-fluoro-2(S)-hydroxy-7-methyl-octyl]-amide;

7,8-difluoro-quinoline-3-carboxylic acid [4(R)-carbamoyl-1(S)-(3,4-dichloro-benzyl)-7-fluoro-2(S)-hydroxy-7-methyl-octyl]-amide;

quinoxaline-2-carboxylic acid (4(R)-carbamoyl-2(S)-hydroxy-7-methyl-1(S)-phenethyl-octyl)-amide;

7,8-difluoro-quinoline-3-carboxylic acid [4(R)-carbamoyl-7-fluoro-1(S)-(4-fluoro-benzyl)-2(S)-hydroxy-7-methyl-octyl]-amide;

quinoxaline-2-carboxylic acid [4(R)-carbamoyl-7-fluoro-1(S)-(4-fluoro-benzyl)-2(S)-hydroxy-7-methyl-octyl]-amide;

quinoxaline-2-carboxylic acid {1(S)-[4(R)-(3-methyl-butyl)-5-oxo-tetrahydro-furan-2-yl]-2(S)-phenyl-ethyl}-amide;

quinoxaline-2-carboxylic acid [1(S)-benzyl-7-fluoro-2(S)-hydroxy-7-methyl-4(R)-(4-methyl-piperazine-1-carbonyl)-octyl]-amide;

quinoxaline-2-carboxylic acid [1(S)-benzyl-4(R)-carbamoyl-2(S)-hydroxy-5-(tetrahydro-pyran-4(R)-yl)-pentyl]-amide;

quinoxaline-2-carboxylic acid [1(S)-benzyl-7-fluoro-2(S)-hydroxy-7-methyl-4(R)-(piperidine-1-carbonyl)-octyl]-amide;

quinoxaline-2-carboxylic acid [1(S)-benzyl-7-fluoro-2(S)-hydroxy-7-methyl-4(R)-(morpholine4(R)-carbonyl)-octyl]-amide;

quinoxaline-2-carboxylic acid [1(S)-benzyl-7-fluoro-2(S)-hydroxy-7-methyl-4(R)-(3-morpholin-4-yl-propionyl)-octyl]-amide;

quinoxaline-2-carboxylic acid [1(S)-benzyl-3-(2-carbamoyl-indan-2-yl)-2(S)-hydroxy-propyl]-amide;
quinoxaline-2-carboxylic acid 1(S)-benzyl-2(S)-hydroxy-4(R)-methylcarbamoyl-7-phenyl-hept-6-enyl)-amide;
quinoline-2-carboxylic acid 1(S)-benzyl-4(R)-carbamoyl-7-fluoro-2(S)-hydroxy-7-methyl-octyl)-amide;
6,7-dihydro-5H-[1]pyrindine-3-carboxylic acid 1(S)-benzyl-4(R)-carbamoyl-7-fluoro-2(S)-hydroxy-7-methyl-octyl)-amide;
quinoxaline-2-carboxylic acid (1(S)-benzyl-4-carbamoyl-4(S)-cyclohexyl-2(S)-hydroxy-butyl)-amide;
quinoxaline-2-carboxylic acid (1(S)-benzyl-4-carbamoyl-4(S)-cyclohexyl-2(S)-hydroxy-butyl)-amide;
quinoxaline-2-carboxylic acid (1(S)-benzyl-4-carbamoyl-4(S)-cyclohexyl-2(S)-hydroxy-butyl)-amide;
quinoxaline-2-carboxylic acid (1(S)-benzyl-4-carbamoyl-4(S)-cyclopentyl-2(S)-hydroxy-butyl)-amide;
quinoline-3-carboxylic acid 1(S)-benzyl-4(R)-carbamoyl-7-fluoro-2(S)-hydroxy-7-methyl-octyl)-amide;
N-1(S)-benzyl-4(R)-carbamoyl-7-fluoro-2(S)-hydroxy-7-methyl-octyl)-5-bromo-nicotinamide;
quinoxaline-2-carboxylic acid [4(R)-carbamoyl-1-(2(S)-fluoro-benzyl)-2(S)-hydroxy-7-methyl-octyl]-amide;
quinoxaline-2-carboxylic acid [4(R)-carbamoyl-1(S)-(2(S)-fluoro-benzyl)-2(S)-hydroxy-7-methyl-octyl]-amide;
quinoxaline-2-carboxylic acid [1(S)-benzyl-4(R)-carbamoyl-2(S)-hydroxy-4(S)-(4-isopropyl-cyclohexyl)-butyl]-amide;
quinoxaline-2-carboxylic acid (4(R)-carbamoyl-2(S)-hydroxy-7-methyl-1(S)-thiophen-2-ylmethyl-octyl)-amide;
quinoxaline-2-carboxylic acid (4(R)-carbamoyl-2(S)-hydroxy-7-methyl-1(S)-thiazol-4(R)-ylmethyl-octyl)-amide;
quinoxaline-2-carboxylic acid [1(S)-benzyl4(S)-carbamoyl-2(S)-hydroxy-4(S)-(3,3,5,5-tetramethyl-cyclohexyl)-butyl]-amide;
quinoxaline-2-carboxylic acid (1(S)-benzyl-4(S)-carbamoyl-2(S)-hydroxy-4(S)-indan-2-yl-butyl)-amide;
quinoxaline-2-carboxylic acid (1(S)-benzyl-4(S)-carbamoyl-4(S)-cycloheptyl-2(S)-hydroxy-butyl)-amide;
quinoxaline-2-carboxylic acid (1(S)-benzyl-4(R)-carbamoyl-2(S)-hydroxy-5-propyl-octyl)-amide;
quinoxaline-2-carboxylic acid (1(S)-benzyl-4(R)-carbamoyl-2(S)-hydroxy-5-propyl-oct-5-enyl)-amide;
quinoxaline-2-carboxylic acid 1(S)-benzyl-4(R)-carbamoyl-2,7-dihydroxy-7-methyl-octyl)-amide;
quinoxaline-2-carboxylic acid 1(S)-benzyl-7-chloro-2(S)-hydroxy-4(R)-methylcarbamoyl-hept-6-enyl)-amide;
quinoxaline-2-carboxylic acid 1(S)-benzyl-7-chloro-2(S)-hydroxy-4(R)-methylcarbamoyl-hept-6-enyl)-amide;
quinoxaline-2-carboxylic acid 1(S)-benzyl-6-chloro-2(S)-hydroxy-4(S)-methylcarbamoyl-hept-6-enyl)-amide;
quinoxaline-2-carboxylic acid 1(S)-benzyl-4(R)-carbamoyl-6-chloro-2(S)-hydroxy-hept-6-enyl)-amide;
quinoxaline-2-carboxylic acid 1(S)-benzyl-4(R)-carbamoyl-6-cyclopropyl-2(S)-hydroxy-hexyl)-amide;
quinoxaline-2-carboxylic acid 1(S)-benzyl-6-cyclopropyl-2(S)-hydroxy-4(R)-methylcarbamoyl-hexyl)-amide;
quinoxaline-2-carboxylic acid [1(S)-benzyl-4(R)-carbamoyl-2(S)-hydroxy4(S)-(4-methyl-cyclohexyl)-butyl]-amide;
quinoxaline-2-carboxylic acid (1(S)-benzyl-4(R)-carbamoyl-2(S)-hydroxy4(S)-indan-2-yl-butyl)-amide;
quinoxaline-2-carboxylic acid [1(S)-benzyl-4(R)-carbamoyl-2(S)-hydroxy-5-(4-trifluoromethoxy-phenyl)-pentyl]-amide;
quinoxaline-2-carboxylic acid [1-benzyl-4(R)-carbamoyl-5-(4-fluoro-phenyl)-2(S)-hydroxy-pentyl]-amide;
quinoxaline-2-carboxylic acid 1(S)-benzyl-4(R)-carbamoyl-7-chloro-2(S)-hydroxy-hept-6-enyl)-amide;
quinoxaline-2-carboxylic acid 1(S)-benzyl-4(R)-carbamoyl-7-chloro-2(S)-hydroxy-hept-6-enyl)-amide;
3-Hydroxy-quinoxaline-2-carboxylic acid 1(S)-benzyl-4(R)-carbamoyl-7-fluoro-2(S)-hydroxy-7-methyl-octyl)-amide;
quinoxaline-2-carboxylic acid 1(S)-benzyl-4(R)-benzylcarbamoyl-7-fluoro-2(S)-hydroxy-7-methyl-octyl)-amide;
quinoxaline-2-carboxylic acid {1(S)-benzyl-7-fluoro-2(S)-hydroxy-7-methyl-4(R)-[(pyridin-3-ylmethyl)-carbamoyl]-octyl}-amide;
quinoxaline-2-carboxylic acid 1(S)-benzyl-8,8-trifluoro-2(S)-hydroxy-4(R)-methylcarbamoyl-7-trifluoromethyl-octyl)-amide;
quinoxaline-2-carboxylic acid 1(S)-benzyl-4(R)-carbamoyl-8,8-trifluoro-2(S)-hydroxy-7-trifluoromethyl-octyl)-amide;
quinoxaline-2-carboxylic acid [2(S)-hydroxy-7-methyl-4(R)-methylcarbamoyl-1(S)-(4-methylcarbamoyl-benzyl)-octyl]-amide;
quinoxaline-2-carboxylic acid (1(S)-benzylp-4(R)-carbamoyl-5-ethyl-2(S)-hydroxy-heptyl)-amide;
quinoxaline-2-carboxylic acid [1(S)-benzyl-4(S)-carbamoyl-2(S)-hydroxy4(S)-(tetrahydro-pyran-4-yl)-butyl]-amide;
quinoxaline-2-carboxylic acid [1(S)-benzyl-7-fluoro-2(S)-hydroxy-7-methyl-4(R)-(2(R)-pyridin-2-yl-ethylcarbamoyl)-octyl]-amide;
quinoxaline-2-carboxylic acid [1(S)-benzyl-4(R)-(3,4-dimethoxy-benzylcarbamoyl)-7-fluoro-2(S)-hydroxy-7-methyl-octyl]-amide;
quinoxaline-2-carboxylic acid 1(S)-benzyl-4(R)-carbamoyl-2(S)-hydroxy-6-methoxy-hexyl)-amide;
quinoxaline-2-carboxylic acid 1(S)-benzyl-4(R)-carbamoyl-7-chloro-2(S)-hydroxy-oct-6-enyl)-amide;
quinoxaline-2-carboxylic acid 1(S)-benzyl-7-chloro-2(S)-hydroxy-4(R)-methylcarbamoyl-oct-6-enyl)-amide;
quinoxaline-2-carboxylic acid [1(S)-benzyl-4(R)-carbamoyl-4(S)-(3,5-dimethyl-cyclohexyl)-2(S)-hydroxy-butyl]-amide;
quinoxaline-2-carboxylic acid {1(S)-benzyl-7-fluoro-2(S)-hydroxy-7-methyl-4(R)-[(pyridin-2-ylmethyl)-carbamoyl]-octyl}-amide;
quinoxaline-2-carboxylic acid {1(S)-benzyl-7-fluoro-2(S)-hydroxy-4(R)-[2-(4-hydroxy-phenyl)-ethylcarbamoyl]-7-methyl-octyl}-amide;
quinoxaline-2-carboxylic acid {1(S)-benzyl-7-fluoro-2(S)-hydroxy-7-methyl-4(R)-[(thiophen-2-ylmethyl)-carbamoyl]-octyl}-amide;
quinoxaline-2-carboxylic acid 1(S)-benzyl-4(R)-carbamoyl-2(S)-hydroxy-6-phenoxy-hexyl)-amide;
quinoxaline-2-carboxylic acid 1(S)-benzyl-4(R)-carbamoyl-2(S)-hydroxy-6-isopropoxy-hexyl)-amide;
quinoxaline-2-carboxylic acid {1(S)-benzyl-7-fluoro-2(S)-hydroxy-7-methyl-4(R)-[2-(4-sulfamoyl-phenyl)-ethylcarbamoyl]-octyl}-amide;
quinoxaline-2-carboxylic acid {1(S)-benzyl-7-fluoro-2(S)-hydroxy-7-methyl-4(R)-[(pyridin-4-ylmethyl)-carbamoyl]-octyl}-amide;
quinoxaline-2-carboxylic acid [1(S)-benzyl4-(2-ethylsulfanyl-ethylcarbamoyl)-7-fluoro-2(S)-hydroxy-7-methyl-octyl]-amide;
quinoxaline-2-carboxylic acid [1(S)-benzyl-7-fluoro-2(S)-hydroxy-4(R)-(2-methoxy-ethylcarbamoyl)-7-methyl-octyl]-amide;

quinoxaline-2-carboxylic acid [1(S)-benzyl-7-fluoro-2(S)-hydroxy-7-methyl-4(R)-(2-pyridin-3-yl-ethylcarbamoyl)-octyl]-amide;

quinoxaline-2-carboxylic acid [1(S)-benzyl-7-fluoro-2(S)-hydroxy-7-methyl-4(R)-(2-pyridin-4(R)-yl-ethylcarbamoyl)-octyl]-amide;

quinoxaline-6-carboxylic acid 1(S)-benzyl-4(R)-carbamoyl-7-fluoro-2(S)-hydroxy-7-methyl-octyl)-amide;

quinoxaline-2-carboxylic acid 1(S)-benzyl-6-tert-butoxy-4(R)-carbamoyl-2(S)-hydroxy-hexyl)-amide;

quinoxaline-2-carboxylic acid {1(S)-benzyl-7-fluoro-2(S)-hydroxy-7-methyl-4(R)-(2-1(S)-methyl-1H-pyrrol-2-yl)-ethylcarbamoyl]-octyl}-amide;

quinoxaline-2-carboxylic acid [1(S)-benzyl-4(S)-carbamoyl-4-(1,1-dioxo-hexahydro-thiopyran-4-yl)-2(S)-hydroxy-butyl]-amide;

quinoxaline-2-carboxylic acid (1(S)-benzyl-7-fluoro-2(S)-hydroxy-4(R)-[2-(6-methoxy-1H-indol-3-yl)-ethylcarbamoyl]-7-methyl-octyl}-amide;

quinoxaline-2-carboxylic acid [1(S)-benzyl-7-fluoro-2(S)-hydroxy-4(R)-(2-methoxy-benzylcarbamoyl)-7-methyl-octyl]-amide;

quinoxaline-2-carboxylic acid [1(S)-benzyl-7-fluoro-2(S)-hydroxy-4(R)-(3-methoxy-benzylcarbamoyl)-7-methyl-octyl]-amide;

quinoxaline-2-carboxylic acid [1(S)-benzyl-7-fluoro-2(S)-hydroxy-7-methyl-4(R)-(2-thiophen-2-yl-ethylcarbamoyl)-octyl]-amide;

quinoxaline-2-carboxylic acid {1(S)-benzyl-7-fluoro-2(S)-hydroxy4(R)-[2-(1H-indol-3-yl)-ethylcarbamoyl]-7-methyl-octyl}-amide;

quinoxaline-2-carboxylic acid {4(R)-[2-(4-amino-phenyl)-ethylcarbamoyl]-1(S)-benzyl-7-fluoro-2(S)-hydroxy-7-methyl-octyl}-amide;

quinoxaline-2-carboxylic acid {1(S)-benzyl-4(R)-[2-(3,5-dimethoxy-phenyl)-ethylcarbamoyl]-7-fluoro-2(S)-hydroxy-7-methyl-octyl}-amide;

quinoxaline-2-carboxylic acid {1(S)-benzyl-4(R)-[2-(3,4-dimethoxy-phenyl)-ethylcarbamoyl]-7-fluoro-2(S)-hydroxy-7-methyl-octyl}-amide;

quinoxaline-2-carboxylic acid {1(S)-benzyl-7-fluoro-4(R)-[(furan-2-ylmethyl)-carbamoyl]-2(S)-hydroxy-7-methyl-octyl}-amide;

quinoxaline-2-carboxylic acid {1(S)-benzyl-4(R)-[2-(2,5-dimethoxy-phenyl)-ethylcarbamoyl]-7-fluoro-2(S)-hydroxy-7-methyl-octyl}-amide;

quinoxaline-2-carboxylic acid [1(S)-benzyl-7-fluoro-2(S)-hydroxy-4(R)-(4-methoxy-benzylcarbamoyl)-7-methyl-octyl]-amide;

quinoxaline-2-carboxylic acid 1(S)-benzyl-4(R)-carbamoyl-6-cyclohexyloxy-2(S)-hydroxy-hexyl)-amide;

quinoxaline-2-carboxylic acid {4(R)-[(1H-benzoimidazol-2-ylmethyl)-carbamoyl]-1(S)-benzyl-7-fluoro-2(S)-hydroxy-7-methyl-octyl}-amide;

quinoxaline-2-carboxylic acid [1(S)-benzyl-7-fluoro-2(S)-hydroxy-4(R)-(2(S)-hydroxymethyl-pyrrolidine-1-carbonyl)-7-methyl-octyl]-amide;

quinoxaline-2-carboxylic acid {1 (S)-benzyl-7-fluoro-2(S)-hydroxy-7-methyl-4(R)-[(tetrahydrofuran-2-ylmethyl)-carbamoyl]-octyl}-amide;

quinoxaline-2-carboxylic acid [1(S)-benzyl4-carbamoyl-4(S)-(4,4-difluoro-cyclohexyl)-2(S)-hydroxy-butyl]-amide;

quinoxaline-2-carboxylic acid [1(S)-benzyl-4(R)-(2,3-dimethoxy-benzylcarbamoyl)-7-fluoro-2(S)-hydroxy-7-methyl-octyl]-amide;

quinoxaline-2-carboxylic acid [1(S)-benzyl-4(S)-carbamoyl-2(S)-hydroxy-4-(1-hydroxy-cyclohexyl)-butyl]-amide;

quinoxaline-2-carboxylic acid [1(S)-benzyl-4(S)-carbamoyl-4-(2,6-dimethyl-tetrahydro-pyran-4-yl)-2(S)-hydroxy-butyl]-amide;

quinoxaline-2-carboxylic acid [4(R)-carbamoyl-7-fluoro-1(S)-(3-fluoro-benzyl)-2(S)-hydroxy-7-methyl-octyl]-amide;

7,8-difluoro-quinoline-3-carboxylic acid 1(S)-benzyl-4(R)-carbamoyl-7-fluoro-2(S)-hydroxy-7-methyl-octyl)-amide;

N-1(S)-benzyl-4(R)-carbamoyl-7-fluoro-2(S)-hydroxy-7-methyl-octyl)-5,6-dichloro-nicotinamide;

benzofuran-2-carboxylic acid 1(S)-benzyl-4(R)-carbamoyl-7-fluoro-2(S)-hydroxy-7-methyl-octyl)-amide;

cinnoline-4(R)-carboxylic acid 1(S)-benzyl-4(R)-carbamoyl-7-fluoro-2(S)-hydroxy-7-methyl-octyl)-amide;

quinoxaline-2-carboxylic acid [4(R)-carbamoyl-7-fluoro-2(S)-hydroxy-1-(4-iodo-benzyl)-7-methyl-octyl]-amide;

pyrazine-2-carboxylic acid 1(S)-benzyl-4(R)-carbamoyl-7-fluoro-2(S)-hydroxy-7-methyl-octyl)-amide;

6,7,8-trifluoro-quinoline-3-carboxylic acid 1(S)-benzyl-4(R)-carbamoyl-7-fluoro-2(S)-hydroxy-7-methyl-octyl)-amide;

quinoline-6-carboxylic acid 1(S)-benzyl-4(R)-carbamoyl-7-fluoro-2(S)-hydroxy-7-methyl-octyl)-amide;

isoquinoline-3-carboxylic acid 1(S)-benzyl-4(R)-carbamoyl-7-fluoro-2(S)-hydroxy-7-methyl-octyl)-amide;

2-methoxy-quinoline-3-carboxylic acid 1(S)-benzyl-4(R)-carbamoyl-7-fluoro-2(S)-hydroxy-7-methyl-octyl)-amide;

1H-benzoimidazole-2-carboxylic acid 1(S)-benzyl-4(R)-carbamoyl-7-fluoro-2(S)-hydroxy-7-methyl-octyl)-amide;

benzothiazole-2-carboxylic acid 1(S)-benzyl-4(R)-carbamoyl-7-fluoro-2(S)-hydroxy-7-methyl-octyl)-amide;

5-methyl-pyrazine-2-carboxylic acid 1(S)-benzyl-4(R)-carbamoyl-7-fluoro-2(S)-hydroxy-7-methyl-octyl)-amide;

quinoxaline-2-carboxylic acid 1(S)-benzyl-4(R)-carbamoyl-2(S)-hydroxy-5-pyridin-3-yl-pentyl)-amide;

quinoxaline-2-carboxylic acid [1(S)-benzyl-4(S)-carbamoyl-2(S)-hydroxy-4-(1-hydroxy-cyclohexyl)-butyl]-amide;

quinoline-3-carboxylic acid (1(S)-benzyl-4(S)-carbamoyl-4-cyclohexyl-2(S)-hydroxy-butyl)-amide;

quinoline-2-carboxylic acid (1(S)-benzyl-4(S)-carbamoyl-4-cyclohexyl-2(S)-hydroxy-butyl)-amide;

fluoro-quinoline-3-carboxylic acid (1(S)-benzyl-4(S)-carbamoyl-4-cyclohexyl-2(S)-hydroxy-butyl)-amide;

N-(1(S)-benzyl-4(S)-carbamoyl-4-cyclohexyl-2(S)-hydroxy-butyl)-5,6-dichloro-nicotinamide;

N-(1(S)-benzyl-4(S)-carbamoyl-4-cyclohexyl-2(S)-hydroxy-butyl)-5-bromo-nicotinamide;

quinoxaline-2-carboxylic acid (4(R)-carbamoyl-7-fluoro-2(S)-hydroxy-7-methyl-1-phenyl-octyl)-amide;

quinoxaline-2-carboxylic acid 1(S)-benzyl-4(R)-carbamoyl-2(S)-hydroxy-5-pyridin-2-yl-pentyl)-amide;

quinoxaline-2-carboxylic acid [4(R)-carbamoyl-2(S)-hydroxy-4-(1-hydroxy-cyclohexyl)-1(S)-thiophen-2-ylmethyl-butyl]-amide;

quinoxaline-2-carboxylic acid [1(S)-benzyl-4(S)-carbamoyl-2(S)-hydroxy-4-(4-hydroxy-tetrahydro-thiopyran-4-yl)-butyl]-amide;

1,3-dimethyl-1H-pyrazolo[3,4-b]pyridine-5-carboxylic acid 1(S)-benzyl-4(R)-carbamoyl-7-fluoro-2(S)-hydroxy-7-methyl-octyl)-amide;

quinoxaline-2-carboxylic acid (1(S)-benzyl-7-fluoro-2(S)-hydroxy-4(R)-hydroxycarbamoyl-7-methyl-octyl)-amide;

quinoxaline-2-carboxylic acid (1(S)-benzyl-7-fluoro-2(S)-hydroxy-4(R)-methoxycarbamoyl-7-methyl-octyl)-amide;

7,8-difluoro-quinoline-3-carboxylic acid (1(S)-benzyl-4(R)-carbamoyl-2(S)-hydroxy-5-phenyl-pentyl)-amide;

quinoxaline-2-carboxylic acid [1(S)-benzyl-4(R)-carbamoyl-5-(2-chloro-phenyl)-2(S)-hydroxy-pentyl]-amide;

quinoxaline-2-carboxylic acid (1(S)-benzyl-4(R)-carbamoyl-2(S)-hydroxy-5-o-tolyl-pentyl)-amide;

quinoxaline-2-carboxylic acid (1(S)-benzyl-2(S)-hydroxy-4(R)-hydroxycarbamoyl-5-phenyl-pentyl)-amide;

quinoxaline-2-carboxylic acid [1(S)-benzyl-4(S)-carbamoyl-2(S)-hydroxy-4-(1-hydroxy-cyclopentyl)-butyl]-amide;

quinoxaline-2-carboxylic acid [1(S)-benzyl4(S)-carbamoyl-2(S)-hydroxy4-(1-hydroxy-4-methyl-cyclohexyl)-butyl]-amide;

quinoxaline-2-carboxylic acid [1(S)-benzyl-4(S)-carbamoyl-5-(3,4-dichloro-phenyl)-2(S)-hydroxy-pentyl]-amide;

quinoxaline-2-carboxylic acid [1(S)-benzyl-4(R)-carbamoyl-5-(2-fluoro-phenyl)-2(S)-hydroxy-pentyl]-amide;

quinoxaline-2-carboxylic acid [1(S)-benzyl-2(S)-hydroxy-4(S)-hydroxycarbamoyl4-(1-hydroxy-cyclopentyl)-butyl]-amide;

quinoxaline-2-carboxylic acid [1(S)-benzyl4(S)-carbamoyl-2(S)-hydroxy4-(1-hydroxy-3-methyl-cyclopentyl)-butyl]-amide;

quinoxaline-2-carboxylic acid [1(S)-benzyl-2(S)-hydroxy-4(S)-hydroxycarbamoyl4-(1-hydroxy-4-methyl-cyclohexyl)-butyl]-amide;

N-(1(S)-benzyl-4(R)-carbamoyl-2(S)-hydroxy-5-phenyl-pentyl)-5-bromo-nicotinamide;

8-Fluoro-quinoline-3-carboxylic acid (1(S)-benzyl-4(R)-carbamoyl-2(S)-hydroxy-5-phenyl-pentyl)-amide;

6,7-dihydro-5H-[1]pyrindine-3-carboxylic acid (1(S)-benzyl4(R)-carbamoyl-2(S)-hydroxy-5-phenyl-pentyl)-amide;

quinoline-3-carboxylic acid (1(S)-benzyl-4(R)-carbamoyl-2(S)-hydroxy-5-phenyl-pentyl)-amide;

quinoxaline-2-carboxylic acid [1(S)-benzyl-4(S)-carbamoyl-2(S)-hydroxy-4-(1-hydroxy-3,5-dimethyl-cyclohexyl)-butyl]-amide;

quinoxaline-2-carboxylic acid [1(S)-benzyl-2(S)-hydroxy-4(S)-hydroxycarbamoyl-4-(1-hydroxy-3,5-dimethyl-cyclohexyl)-butyl]-amide;

quinoxaline-2-carboxylic acid [1(S)-benzyl-4(S)-carbamoyl-2(S)-hydroxy4-(1-hydroxy-cycloheptyl)-butyl]-amide;

quinoxaline-2-carboxylic acid [1(S)-benzyl-2(S)-hydroxy-4(S)-hydroxycarbamoyl-4-(1-hydroxy-cycloheptyl)-butyl]-amide;

quinoxaline-2-carboxylic acid [1(S)-benzyl-4(R)-carbamoyl-5-(3-fluoro-phenyl)-2(S)-hydroxy-pentyl]-amide;

quinoxaline-2-carboxylic acid (1(S)-benzyl-4(R)-carbamoyl-2(S)-hydroxy-5-m-tolyl-pentyl)-amide;

quinoxaline-2-carboxylic acid (1(S)-benzyl-2(S)-hydroxy4-isobutylcarbamoyl-butyl)-amide;

quinoxaline-2-carboxylic acid [1(S)-benzyl-4(S)-carbamoyl-2(S)-hydroxy4-(2-hydroxy-adamantan-2-yl)-butyl]-amide;

quinoxaline-2-carboxylic acid [1(S)-benzyl-4(S)-carbamoyl-2(S)-hydroxy-4-(9-hydroxy-bicyclo[3.3.1]non-9-yl)-butyl]-amide;

quinoxaline-2-carboxylic acid [1(S)-benzyl-2(S)-hydroxy-4(S)-(2-hydroxy-adamantan-2-yl)-4-hydroxycarbamoyl-butyl]-amide;

quinoxaline-2-carboxylic acid [1(S)-benzyl-2(S)-hydroxy-4(S)-(9-hydroxy-bicyclo[3.3.1]non-9-yl)-4-hydroxycarbamoyl-butyl]-amide;

quinoxaline-2-carboxylic acid [1(S)-benzyl-4(R)-carbamoyl-2(S)-hydroxy-5-(3-methoxy-phenyl)-pentyl]-amide;

quinoxaline-2-carboxylic acid [1(S)-benzyl-4(S)-carbamoyl-2(S)-hydroxy-4-(1-hydroxy-4-propyl-cyclohexyl)-butyl]-amide;

quinoxaline-2-carboxylic acid [1(S)-benzyl-2(S)-hydroxy-4(S)-hydroxycarbamoyl-4-(1-hydroxy-4-propyl-cyclohexyl)-butyl]-amide;

quinoxaline-2-carboxylic acid [1(S)-benzyl-4(R)-carbamoyl-2(S)-hydroxy-5-(4-methoxy-phenyl)-pentyl]-amide;

quinoxaline-2-carboxylic acid [1(S)-benzyl-4(S)-carbamoyl-4(S)-(4-ethyl-1-hydroxy-cyclohexyl)-2-hydroxy-butyl]-amide;

quinoxaline-2-carboxylic acid [1(S)-benzyl-4(S)-carbamoyl-2(S)-hydroxy-4-(1-hydroxy-4,4-dimethyl-cyclohexyl)-butyl]-amide;

quinoxaline-2-carboxylic acid [1(S)-benzyl-2(S)-hydroxy-4(S)-hydroxycarbamoyl-4-(1-hydroxy-4,4-dimethyl-cyclohexyl)-butyl]-amide;

quinoxaline-2-carboxylic acid [1(S)-benzyl-4(S)-carbamoyl-4-(4,4-difluoro-1-hydroxy-cyclohexyl)-2-hydroxy-butyl]-amide;

quinoxaline-2-carboxylic acid [4(R)-carbamoyl-1(S)-(3-fluoro-benzyl)-2(S),7-dihydroxy-7-methyl-octyl]-amide;

quinoxaline-2-carboxylic acid [4(R)-carbamoyl-1(S)-(3,5-difluoro-benzyl)-2(S),7-dihydroxy-7-methyl-octyl]-amide;

quinoxaline-2-carboxylic acid 4(R)-carbamoyl-1(S)-(3-chloro-benzyl)-2(S),7-dihydroxy-7-methyl-octyl]-amide;

quinoxaline-2-carboxylic acid [1(S)-(3-chloro-benzyl)-2(S),7-dihydroxy-4(R)-hydroxycarbamoyl-7-methyl-octyl]-amide;

7,8-Difluoro-quinoline-3-carboxylic acid (1S)-benzyl-4(R)-carbamoyl-2(S),7-dihydroxy-7-methyl-octyl)-amide;

6,7,8-Trifluoro-quinoline-3-carboxylic acid (1(S)-benzyl-4(R)-carbamoyl-2(S),7-dihydroxy-7-methyl-octyl)-amide;

quinoxaline-2-carboxylic acid [1(S)-(3,5-difluoro-benzyl)-2(S),7-dihydroxy-4(R)-hydroxycarbamoyl-7-methyl-octyl]-amide;

quinoxaline-2-carboxylic acid (1(S)-benzyl-2(S),7-dihydroxy-4(R)-hydroxycarbamoyl-7-methyl-octyl)-amide;

7,8-Difluoro-quinoline-3-carboxylic acid (1(S)-benzyl-4(R)-ethylcarbamoyl-2(S),7-dihydroxy-7-methyl-octyl)-amide;

N-(1(S)-Benzyl-4(R)-carbamoyl-2(S),7-dihydroxy-7-methyl-octyl)-4-trifluoromethyl-nicotinamide;

quinoxaline-2-carboxylic acid [4(R)-carbamoyl-1(S)-(2-chloro-benzyl)-2(S),7-dihydroxy-7-methyl-octyl]-amide;

7,8-Difluoro-quinoline-3-carboxylic acid [1(4R)-carbamoyl-1(S)-(3-fluoro-benzyl)-2(S),7-dihydroxy-7-methyl-octyl]-amide;

quinoxaline-2-carboxylic acid [1(S)-(2-fluoro-benzyl)-2(S),7-dihydroxy4(R)-hydroxycarbamoyl-7-methyl-octyl]-amide;

quinoxaline-2-carboxylic acid (4(R)-carbamoyl-2(S),7-dihydroxy-7-methyl-1(S)-thiophen-2-ylmethyl-octyl)-amide;

quinoxaline-2-carboxylic acid [4(R)-carbamoyl-1(S)-(2-fluoro-benzyl)-2(S),7-dihydroxy-7-methyl-octyl]-amide;
quinoxaline-2-carboxylic acid [1(S)-(3,4-difluoro-benzyl)-2(S),7-dihydroxy-4(R)-hydroxycarbamoyl-7-methyl-octyl]-amide;
quinoxaline-2-carboxylic acid [4(R)-carbamoyl-I(S)-(3,4-difluoro-benzyl)-2(S),7-dihydroxy-7-methyl-octyl]-amide;
quinoxaline-2-carboxylic acid (4(R)-carbamoyl-2(S),7-dihydroxy-7-methyl-1(S)-naphthalen-1-ylmethyl-octyl)-amide;
6,7,8-Trifluoro-quinoline-3-carboxylic acid [4(R)-carbamoyl-1(S)-(3-fluoro-benzyl)-2(S),7-dihydroxy-7-methyl-octyl]-amide;
quinoxaline-2-carboxylic acid (4(R)-carbamoyl-2(S),7-dihydroxy-7-methyl-1(S)-naphthalen-2-ylmethyl-octyl)-amide;
quinoxaline-2-carboxylic acid (2(S),7-dihydroxy-4(R)-hydroxycarbamoyl-7-methyl-1(S)-naphthalen-2-ylmethyl-octyl)-amide;
quinoxaline-2-carboxylic acid (1(S)-benzo[b]thiophen-3-ylmethyl-4(R)-carbamoyl-2(S),7-dihydroxy-7-methyl-octyl)-amide;
quinoxaline-2-carboxylic acid [1-benzyl-4-carbamoyl-2-hydroxy-5-(4-hydroxy-phenyl)-pentyl]-amide;
quinoxaline-2-carboxylic acid [1-benzyl-4-carbamoyl-2-hydroxy-5-(3-hydroxy-phenyl)-pentyl]-amide;
quinoxaline-2-carboxylic acid [1-benzyl-4-carbamoyl-2-hydroxy-5-(2-hydroxy-phenyl)-pentyl]-amide;
quinoxaline-2-carboxylic acid [1-benzyl-4-carbamoyl-2-hydroxy-5-(2-hydroxy-5-methyl-phenyl)-pentyl)-amide;
quinoxaline-2-carboxylic acid [1-benzyl-4-carbamoyl-2-hydroxy-5-(2-hydroxy-3-methyl-phenyl)-pentyl)-amide;
quinoxaline-2-carboxylic acid [1-benzyl-4-carbamoyl-5-(3-ethoxy-2-hydroxy-phenyl)-2-hydroxy-pentyl]-amide;
quinoxaline-2-carboxylic acid [1-benzyl-4-carbamoyl-2-hydroxy-5-(4-hydroxy-3,5-dimethyl-phenyl)-pentyl]-amide;
quinoxaline-2-carboxylic acid (1-benzyl-4-carbamoyl-2,6-dihydroxy-6-methyl-heptyl)-amide;
quinoxaline-2-carboxylic acid (1-benzyl-4-carbamoyl-2-hydroxy-5-(1-hydroxy-cyclohexyl)-pentyl]-amide;
quinoxaline-2-carboxylic acid (1(S)-benzyl-4(S)-(4,4-difluoro-1-hydroxy-cyclohexyl)-2(S)-hydroxy4-hydroxycarbamoyl-butyl]-amide; and
quinoxaline-2-carboxylic acid [1(S)-benzyl-4(S)-carbamoyl-2(S)-hydroxy4-(1-hydroxy-4-trifluoromethyl-cyclohexyl)-butyl]-amide.

The present invention also relates to a pharmaceutical composition for treating or preventing a disorder or condition selected from autoimmune diseases (such as rheumatoid arthritis, type I diabetes (recent onset), inflammatory bowel disease, optic neuritis, psoriasis, multiple sclerosis, polymyalgia rheumatica, uveitis, and vasculitis), acute and chronic inflammatory conditions (such as osteoarthritis, adult respiratory distress syndrome, Respiratory Distress Syndrome of infancy, ischemia reperfusion injury, and glomerulonephritis), allergic conditions (such as asthma and atopic dermatitis), infection associated with inflammation (such as viral inflammation (including influenza and hepatitis) and Guillian-Barre), transplantation tissue rejection, atherosclerosis, restenosis, HIV infectivity (co-receptor usage), and granulomatous diseases (including sarcoidosis, leprosy and tuberculosis). in a mammal, preferably a human, comprising an amount of a compound of the formula I or a pharmaceutically acceptable salt thereof effective in treating or preventing such disorder or condition and a pharmaceutically acceptable carrier.

The present invention also relates to a pharmaceutical composition for treating or preventing a disorder or condition that can be treated or prevented by inhibiting MIP-1α binding to the receptor CCR1 in a mammal, preferably a human, comprising an amount of a compound of the formula I, or a pharmaceutically acceptable salt thereof, effective in treating or preventing such disorder or condition and a pharmaceutically acceptable carrier. Examples of such disorders and conditions are those enumerated in the preceding paragraph.

The present invention also relates to a method for treating or preventing a disorder or condition selected from autoimmune diseases (such as rheumatoid arthritis, type I diabetes (recent onset), inflammatory bowel disease, optic neuritis, psoriasis, multiple sclerosis, polymyalgia rheumatica, uveitis, and vasculitis), acute and chronic inflammatory conditions (such as osteoarthritis, adult respiratory distress syndrome, Respiratory Distress Syndrome of infancy, ischemia reperfusion injury, and glomerulonephritis), allergic conditions (such as asthma and atopic dermatitis), infection associated with inflammation (such as viral inflammation (including influenza and hepatitis) and Guillian-Barre), transplantation tissue rejection, atherosclerosis, restenosis, HIV infectivity (co-receptor usage), and granulomatous diseases (including sarcoidosis, leprosy and tuberculosis) in a mammal, preferably a human, comprising administering to a mammal in need of such treatment or prevention an amount of a compound of the formula I, or a pharmaceutically acceptable salt thereof, that is effective in treating or preventing such disorder or condition.

The present invention also relates to a method for treating or preventing a disorder or condition that can be treated or prevented by antagonizing the CCR1 receptor in a mammal, preferably a human, comprising administering to a mammal in need of such treatment or prevention an amount of a compound of the formula I, or a pharmaceutically acceptable salt thereof, that is effective in treating or preventing such disorder or condition.

The present invention also relates to a pharmaceutical composition for treating or preventing a disorder or condition selected from autoimmune diseases (such as rheumatoid arthritis, type I diabetes (recent onset), inflammatory bowel disease, optic neuritis, psoriasis, multiple sclerosis, polymyalgia rheumatica, uveitis, and vasculitis), acute and chronic inflammatory conditions (such as osteoarthritis, adult respiratory distress syndrome, Respiratory Distress Syndrome of infancy, ischemia reperfusion injury, and glomerulonephritis), allergic conditions (such as asthma and atopic dermatitis), infection associated with inflammation (such as viral inflammation (including influenza and hepatitis) and Guillian-Barre), transplantation tissue rejection, atherosclerosis, restenosis, HIV infectivity (co-receptor usage), and granulomatous diseases (including sarcoidosis, leprosy and tuberculosis) in a mammal, preferably a human, comprising a CCR1 receptor antagonizing effective amount of a compound of the formula I, or a pharmaceutically acceptable salt thereof, and a pharmaceutically acceptable carrier.

The present invention also relates to a pharmaceutical composition for treating or preventing a disorder or condition that can be treated or prevented by antagonizing the CCR1 receptor in a mammal, preferably a human, comprising a CCR1 receptor antagonizing effective amount of a compound of the formula I, or a pharmaceutically acceptable salt thereof, and a pharmaceutically acceptable carrier.

The present invention also relates to a method for treating or preventing a disorder or condition selected from autoimmune diseases (such as rheumatoid arthritis, type I diabetes (recent onset), inflammatory bowel disease, optic neuritis, psoriasis, multiple sclerosis, polymyalgia rheumatica, uveitis, and vasculitis), acute and chronic inflammatory conditions (such as osteoarthritis, adult respiratory distress syndrome, Respiratory Distress Syndrome of infancy, ischemia reperfusion injury, and glomerulonephritis), allergic conditions (such as asthma and atopic dermatitis), infection associated with inflammation (such as viral inflammation (including influenza and hepatitis) and Guillian-Barre), transplantation tissue rejection, atherosclerosis, restenosis, HIV infectivity (co-receptor usage), and granulomatous diseases (including sarcoidosis, leprosy and tuberculosis) in a mammal, preferably a human, comprising administering to a mammal in need of such treatment or prevention a CCR1 receptor antagonizing effective amount of a compound of formula I, or a pharmaceutically acceptable salt thereof.

This invention also encompasses pharmaceutical compositions containing and methods of treating or preventing comprising administering prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain. Prodrugs also include compounds of formula I in which the secondary amide and its β-hydroxy when taken together form a group of the formula

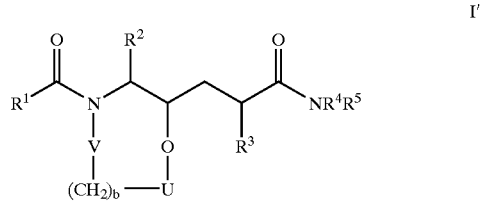

wherein $R^1$, $R^2$, $R^3$, $R^4$ and $R^5$ are as defined in formula I and U and V are independently carbonyl, methylene, $So_2$ or $SO_3$, and b is an integer from one to three wherein each methylene group is optionally substituted with hydroxy.

DETAILED DESCRIPTION OF THE INVENTION

Compounds of the formula I may be prepared according to the following reaction schemes and discussion. Unless otherwise indicated g, n, m, p, and $R^1$ through $R^6$ and structural formula I in the reaction Schemes and discussion that follow are as defined above.

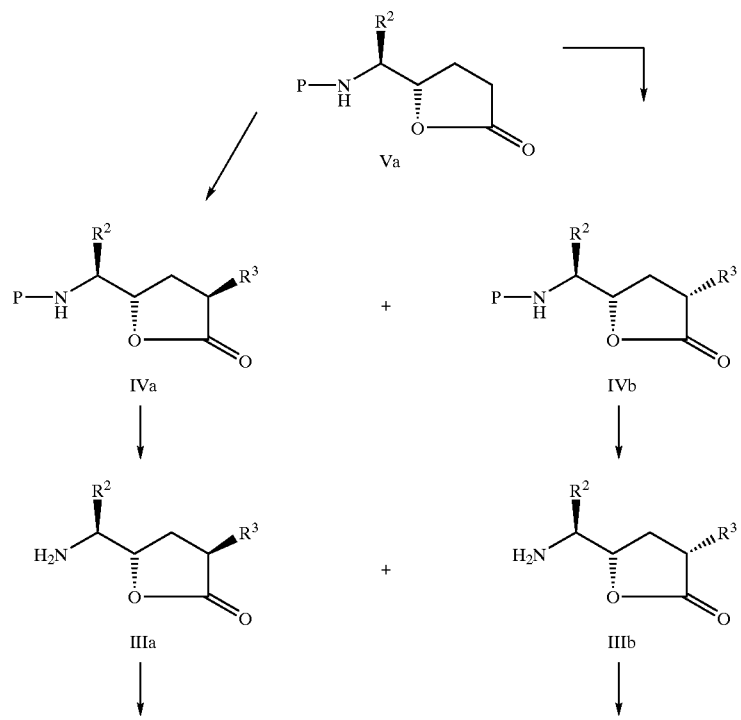

-continued

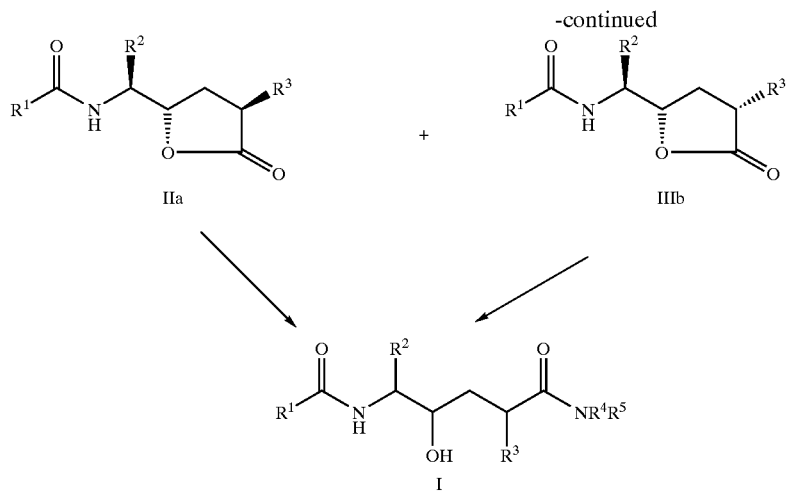

Scheme 1 refers to the preparation of compounds of the formula I having the exact stereochemistry

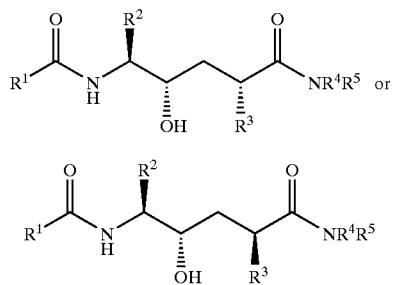

Compounds of the formula Ia and Ib, or any of the intermediates thereof, can be separated by column chromatography according to methods well known to those of ordinary skill in the art, to yield pure compounds of the formula Ia and Ib.

Referring to Scheme 1, compounds of the formula I, wherein either or both $R^4$ or $R^5$ are other than hydrogen, are prepared from compounds of the formula II (i.e. IIa and IIb) by reaction with a compound of the formula $R^4R^5NH$ in a polar solvent at a temperature from about 0° C. to about 100° C., preferably the boiling point of the solvent used, i.e. 65° C. when methanol is the solvent. Suitable solvents include, alcohols, such as methanol, ethanol, or butanols or ethers such as glyme or dioxane (an acid catalyst is preferably used with an ether solvent). Preferably the solvent is dioxane.

Alternatively, compounds of formula I, wherein either or both $R^4$ and $R^5$ are hydrogen, can be prepared from compounds of formula II, (i.e. IIa and IIb) by reaction with ammonia or another volatile amine in a polar solvent at a temperature from about –10° C. to about 35° C., preferably at about 30° C. Suitable solvents include, alcohols, such as methanol, ethanol, or butanols; or ethers such as glyme or dioxane (an acid catalyst may be used with an ether solvent). Preferably the solvent is methanol.

Compounds of formula II are prepared by coupling a compound of formula III (i.e. IIIa and IIIb) with an acid of the formula $R^1CO_2H$. Such a coupling reaction is generally conducted at a temperature of about –30° C. to about 80° C., preferably about 0° C. to about 25° C. Examples of suitable coupling reagents which activate the carboxylic acid functionality are dicyclohexylcarbodiimide/ hydroxybenzotriazole (DCC/HBT), N-3-dimethylaminopropyl-N'-ethylcarbodiimide (EDC)/HBT, 2-ethyoxy-1-ethoxycarbonyl-1,2-dihydroquinoline (EEDQ), carbonyl diimidazole (CDI)/ dimethylaminopyridine (DMAP), and diethylphosphorylcyanide. The coupling is conducted in an inert solvent, preferably an aprotic solvent, such as acetonitirile, dichloromethane, chloroform, and dimethylformamide. The preferred solvent is dichloromethane.

For a discussion of other conditions used for amide coupling see Houben-Weyl, Vol. XV, part II, E. Wunsch, Ed., George Theime Veriag, 1974, Stuttgart, and those described in M. Bodanszky. *Principles of Peptide Synthesis*, Springer-Verlag, Berlin (1984) and *The Peptides, Analysis, Synthesis and Biology* (ed. E. Gross and J. Meienhofer), Vols 1–5. (Academic Press, New York) 1979–1983.

The compounds of formula III, wherein $R^3$ is $(C_1-C_{10})$ alkyl, $(C_3-C_{10})$cycloalkyl-$(CH_2)_{n-}$, $(C_2-C_9)$ heterocycloalkyl-$(CH_2)_{n-}$, $(C_2-C_9)$heteroaryl-$(CH_2)_{n-}$, or aryl-$(CH_2)_{n-}$ can be prepared by deprotection of compounds of the formula IV (i.e. IVa and IVb). Suitable protecting groups, of the formula P, include carbobenzyloxy, t-butoxy carbonyl or 9-fluorenyl-methylenoxy carbonyl.

For example:

(a) If the protecting group, P, of the compound of the formula IV is carbobenzyloxy, the latter may be removed by hydrogenation with a nobel metal catalyst such as palladium or palladium hydroxide on carbon in the presence of hydrogen. The hydrogenation is generally conducted at a temperature of about 0° C. to about 100° C., preferably about 20° C. to 50° C.

(b) If the protecting group, P, is t-butoxycarbonyl group, such group may be removed by acidolysis. Acidolysis may be conducted with HCl in dioxane or with trifluoracetic acid in methylene chloride at a temperature of about –30° C. to about –70° C., preferably about –5° C. to about 35° C.

(c) If the protecting group, P, is 9-fluorenylmethylenoxycarbonyl, such group may be removed by treatment with an amine base, preferably piperidine. This reaction may be run in piperidine as solvent at 10° C. to about 100° C., preferably at 25° C.

Compounds of the formula III, wherein $R^3$ is substituted $(C_1-C_{10})$alkyl, $(C_3-C_{10})$cycloalkyl-$(CH_2)_{n-}$ or $(C_2-C_9)$ heterocycloalkyl-$(CH_2)_{n-}$ may be prepared from compounds of the formula IV, wherein $R^3$ is $(C_1-C_{10})$alkyl, ($C_3$–$C_{10}$)cycloalkyl-$(CH_2)_n$— or ($C_2$–$C_9$)heterocycloalkyl-$(CH_2)_n$—, wherein one of the carbon-carbon single bonds is replaced by a carbon-carbon double bond, by methods well known to those of ordinary skill in the art. Specifically, one example of introduction of substitution into the $R^3$ group, a compound of formula III, wherein $R^3$ is ($C_1$–$C_{10}$)alkyl substituted by one to three fluoro groups can be prepared from compounds of the formula IV, wherein $R^3$ is ($C_1$–$C_{10}$) alkyl, wherein one of the carbon-carbon single bonds of said ($C_1$–$C_{10}$)alkyl has been replaced by a carbon-carbon double bond, by reaction with hydrogen fluoride in pyridine (i.e. pyridinium poly(hydrogen fluoride), in a reaction inert solvent. Suitable solvents include cyclohexane, toluene or benzene, preferably benzene. The aforesaid reaction is run at a temperature from about −78° C. to about 35° C. Preferably, this reaction is carried out in benzene at about 25° C.

Compounds of the formula IV, wherein $R^3$ is ($C_1$–$C_{10}$) alkyl, ($C_3$–$C_{10}$)cycloalkyl-$(CH_2)_n$—, ($C_2$–$C_9$) heterocycloalkyl-$(CH_2)_n$—, ($C_2$–$C_9$)heteroaryl-$(CH_2)_n$— or aryl-$(CH_2)_n$—, wherein n is other than zero, can be prepared by reaction of a compound of formula V with a compound of the formula $R^3$-L, wherein L is a leaving group, in the presence of a strong base in an aprotic polar solvent. Suitable leaving groups include chloro, fluoro, bromo, iodo, mesylate, triflate or tosylate. Preferably, the leaving group is a triflate, iodide or bromide. Triflates may be easily prepared according to the method of Beard, et al., *J Org Chem.*, 38, 3673(1973). Suitable bases include lithium dialkyl amides such as lithium N-isopropyl-N-cyclohexylamide or potassium hydride. Suitable solvents include ethers (such as THF, glyme or dioxane) benzene or toluene, preferably THF. The aforesaid reaction is conducted at about −78° C. to about 0° C., preferably at about −78° C.

Alternatively, compounds of the formula IV, wherein $R^3$ is ($C_1$–$C_{10}$)alkyl, ($C_3$–$C_{10}$)cycloalkyl-$(CH_2)_n$— or ($C_2$–$C_9$) heterocycloalkyl-$(CH_2)_n$— can be prepared by reaction of a compound of formula V with an aldehyde or ketone precursor of $R^3$ in an aldol condensation. For example, a compound of the formula V can be reacted with a compound of the formula $R^3$(=O) in the presence of a base, to form an aldol intermediate of the formula

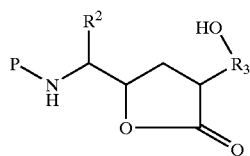

VI which may be isolated and taken on to final product or converted directly in the same reaction step to a compound of the formula IV by the loss of water. The degree of completion for the conversion of compounds of the formula II to the aldol product of formula I may be assessed using one or more analytical techniques, such as thin layer chromatography (tlc) or mass spectrometry. In some instances it may be possible or desirable to isolate the intermediate of formula VI. In such case, the compound of formula VI may be converted into the compound of formula IV by the elimination of water using techniques which are familiar to those skilled in the art, for example, by heating to the reflux temperature a solution of the compound of formula VI in a solvent such as benzene, toluene or xylene, in the presence of a catalytic amount of phosphorous pentoxide, benzene-or p-toluene-sulfonic acid with provision for the removal of the water generated, preferably (methoxycarbonylsulfamoyl)-triethylammonium hydroxide (Burgess reagent). Such water removal techniques may involve the use of molecular sieves or a Dean-Stark trap to isolate the water created as an azeotrope with the solvent.

The aldol reaction is typically carried out in a polar solvent such as DMSO, DMF, tetrahydrofuran (THF), methanol or ethanol, at a temperature from about −78° C. to about 80° C. Preferably, this reaction is carried out in THF at about −78° C. Suitable bases for use in the aldol formation step include potassium carbonate ($K_2CO_3$), sodium carbonate ($Na_2CO_3$), sodium hydride (NaH), sodium methoxide, potassium-tert.-butoxide, lithium diisopropylamide, pyrrolidine and piperidine. Lithium diisopropylamide is preferred. Aldol condensations are described in "*Modem Synthetic Reactions*," Herbert O. House, 2d. Edition, W. A. Benjamin, Menlo Park, Calif., 629–682(1972), *J. Org. Chem.*, 49, 2455(1984), and *Tetrahedron*, 38 (20), 3059(1982).

Compounds of the formula IV wherein $R^3$ is unsaturated can be converted to saturated analogues by hydrogenating the compounds containing a carbon-carbon double bond, using standard techniques that are well known to those skilled in the art. For example, reduction of the double bond may be effected with hydrogen gas ($H_2$), using catalysts such as palladium on carbon (Pd/C), palladium on barium sulfate (Pd/BaSO_4), platinum on carbon (PVC), or tris (triphenylphosphine) rhodium chloride (Wilkinson's catalyst), in an appropriate solvent such as methanol, ethanol, THF, dioxane or ethyl acetate, at a pressure from about 1 to about 5 atmospheres and a temperature from about 10° C. to about 60° C., as described in *Catalytic Hydrogenation in Organic Synthesis*, Paul Rylander, Academic Press Inc., San Diego, 31–63 (1979). The following conditions are preferred: Pd on carbon, methanol at 25° C. and 50 psi of hydrogen gas pressure. This method also provides for introduction of hydrogen isotopes (i.e., deuterium, tritium) by replacing $^1H_2$ with $^2H_2$ or $^3H_2$ in the above procedure.

An alternative procedure employing the use of reagents such as ammonium formate and Pd/C in methanol at the reflux temperature under an inert atmosphere (e.g., nitrogen or argon gas) is also effective in reducing the carbon-carbon double bond of compounds of the formula I. Another alternative method involves selective reduction of the carbon-carbon bond. This can be accomplished using samarium and iodine or samarium iodide ($SmI_2$) in methanol or ethanol at about room temperature, as described by R. Yanada et. al., *Synlett.*, 443–4 (1995).

Compounds of the formula V can be prepared by methods well known to those of ordinary skill in the art or are commercially available. Specifically, compounds of the formula Va and Vb (shown below) can be prepared by the method of Fray et al., (*J. Org. Chem.*, 51, 4828–4833(1986)) using an (S)-aldehyde of the formula

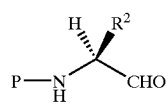

VII

Compounds of the formula VII are prepared by reducing amino acids or amino esters to alcohols (Stanfield et al., *J. Org. Chem.* 46, 4799–4800 (1981), Soai et al., *Bull. Chem. Soc.* Jpn., 57, 2327 (1984)) followed by oxidation of the alcohols to aldehydes of the formula VII (Luly et al., *J.Org. Chem.*, 53 (26), 6109–6112 (1988) and Denis et al., *J Org. Chem.*, 56 (24), 6939–6942 (1991).). Un-natural amino acids can be prepared according to the method of Myers et al., *Tet. Lett.* 36, (1995) and Myers et al. *J. Am. Chem. Soc.,* 117, 8488–8489 (1995).

Alternatively, compounds of the formula V can also be made by the method of DeCamp et al., (*Tetrahedron Lett.,* 32, 1867 (1991)).

Compounds of the formula I, with the exact stereochemistry

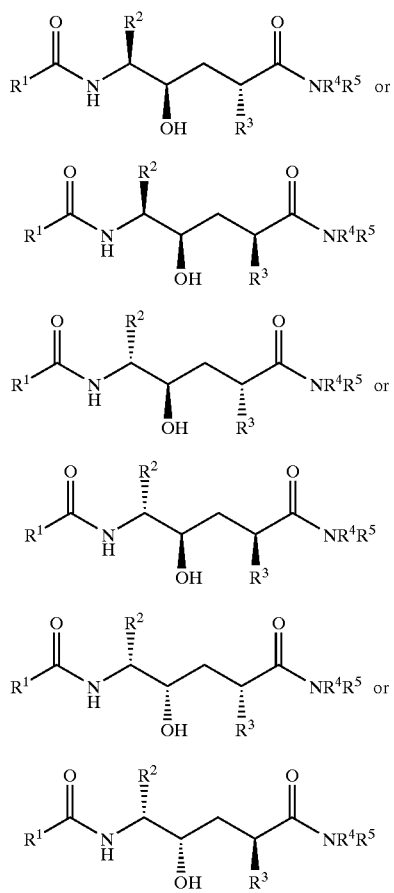

can be prepared according to the methods of Scheme 1, using either the minor lactone diastereomer of the formula,

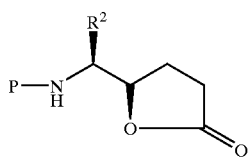

which can be prepared by the method of Fray, supra, from the (S)-aldehyde, or the alternate diastereomeric pair of the formula

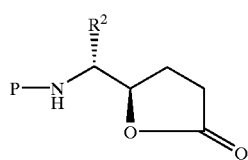

-continued

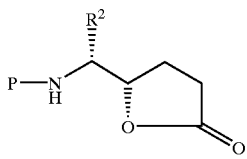

which can be prepared using the corresponding (R)-aldehyde according to the method of Fray, supra.

Aldehyde or ketone precursors of the group $R^3$ are commercially available (e.g., cyclohexanone) or can be made by methods well known to those of ordinary skill in the art, such as described in *J. Am. Chem. Soc.,* 90, 7001 (1968) and *J. Org. Chem.,* 40, 574 (1975).

Unless indicated otherwise, the pressure of each of the above reactions is not critical. Generally, the reactions will be conducted at a pressure of about one to about three atmospheres, preferably at ambient pressure (about one atmosphere).

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

Compounds of the formula I and their pharmaceutically acceptable salts (hereinafter also referred to, collectively, as "the active compounds") are potent antagonists of the CCR1 receptors. The active compounds are useful in the treatment or prevention of autoimmune diseases (such as rheumatoid arthritis, type I diabetes (recent onset), inflammatory bowel disease, optic neuritis, psoriasis, multiple sclerosis, polymyalgia rheumatica, uveitis, and vasculitis), acute and chronic inflammatory conditions (such as osteoarthritis, adult respiratory distress syndrome, Respiratory Distress Syndrome of infancy, ischemia reperfusion injury, and glomerulonephritis), allergic conditions (such as asthma and atopic dermatitis), infection associated with inflammation (such as viral inflammation (including influenza and hepatitis) and Guillian-Barre), transplantation tissue rejection, atherosclerosis, restenosis, HIV infectivity (co-receptor usage), and granulomatous diseases (including sarcoidosis, leprosy and tuberculosis).

The activity of the compounds of the invention can be assessed according to procedures know to those of ordinary skill in the art. Examples of recognized methods for determining CCR1 induced migration can be found in Coligan, J. E., Kruisbeek, A. M., Margulies, D. H., Shevach, E. M., Strober, W. editors: *Current Protocols In Immunology*, 6.12.1–6.12.3.(John Wiley and Sons, NY, 1991). One specific example of how to determine the activity of a compound for inhibiting migration is described in detail below.

Chemotaxis Assay

The ability of compounds to inhibit the chemotaxis to various chemokines can be evaluated using standard 48 or 96 well Boyden Chambers with a 5 micron polycarbonate filter. All reagents and cells can be prepared in standard RPMI (BioWhitikker Inc.) tissue culture medium supplemented with 1 mg/ml of bovine serum albumin. Briefly, MIP-1α (Peprotech, Inc., P.O. Box 275, Rocky Hill N.J.) or other test agonists, were placed into the lower chambers of the Boyden chamber. A polycarbonate filter was then applied and the upper chamber fastened. The amount of agonist chosen is that determined to give the maximal amount of chemotaxis in this system (e.g., 1 nM for MIP-1α should be adequate).

THP-1 cells (ATCC TIB-202), primary human monocytes, or primary lymphocytes, isolated by standard techniques can then be added to the upper chambers in triplicate together with various concentrations of the test compound. Compound dilutions can be prepared using standard serological techniques and are mixed with cells prior to adding to the chamber.

After a suitable incubation period at 37 degrees centigrade (e.g. 3.5 hours for THP-1 cells, 90 minutes for primary monocytes), the chamber is removed, the cells in the upper chamber aspirated, the upper part of the filter wiped and the number of cells migrating can be determined according to the following method.

For THP-1 cells, the chamber (a 96 well variety manufactured by Neuroprobe) can be centrifuged to push cells off the lower chamber and the number of cells can be quantitated against a standard curve by a color change of the dye fluorocein diacetate.

For primary human monocytes, or lymphocytes, the filter can be stained with Dif Quik® dye (American Scientific Products) and the number of cells migrating can be determined microscopically.

The number of cells migrating in the presence of the compound are divided by the number of cells migrating in control wells (without the compound). The quotant is the % inhibition for the compound which can then be plotted using standard graphics techniques against the concentration of compound used. The 50% inhibition point is then determined using a line fit analysis for all concentrations tested. The line fit for all data points must have an coefficient of correlation (R squared) of >90% to be considered a valid assay.

All of the compounds of the invention that were tested had $IC_{50}$ of less than 25 μM, in the Chemotaxis assay.

The compositions of the present invention may be formulated in a conventional manner using one or more pharmaceutically acceptable carriers. Thus, the active compounds of the invention may be formulated for oral, buccal, intranasal, parenteral (eg., intravenous, intramuscular or subcutaneous) or rectal administration or in a form suitable for administration by inhalation or insufflation. The active compounds of the invention may also be formulated for sustained delivery.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insulator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., rheumatoid arthritis) is 0.1 to 1000 mg of the active ingredient per unit dose which could be administered, for example, 1 to 4 times per day.

Aerosol formulations for treatment of the conditions referred to above (e.g,, rheumatoid arthritis) in the average adult human are preferably arranged so that each metered dose or "puff" of aerosol contains 20 $\mu$g to 1000 $\mu$g of the compound of the invention. The overall daily dose with an aerosol will be within the range 0.1 mg to 1000 mg. Administration may be several times daily, for example 2, 3, 4 or 8 times, giving for example, 1, 2 or 3 doses each time.

The active agents can be formulated for sustained delivery according to methods well known to those of ordinary skill in the art. Examples of such formulations can be found in U.S. Pat. Nos. 3,538,214, 4,060,598, 4,173,626, 3,119,742, and 3,492,397.

The compounds of the invention can also be utilized in combination therapy with other therapeutic agents such as with immunosuppressant agents such as cyclosporin A and FK-506, Cellcept®, rapamycin, leuflonamide or with classical anti-inflammatory agents (e.g. cyclooxygenase/ lipoxegenase inhibitors) such as tenidap, aspirin, acetaminophen, naproxen and piroxicam, steroids including prednisone, azathioprine and biological agents such as OKT-3, anti IL-2 monoclonal antibodies (such as TAC),.

The following Examples illustrate the preparation of the compounds of the present invention. Melting points are uncorrected. NMR data are reported in parts per million ($\delta$) and are referenced to the deuterium lock signal from the sample solvent (deuteriochloroform unless otherwise specified). Commercial reagents were utilized without further purification. THF refers to tetrahydrofuran. DMF refers to N,N-dimethylformamide. Chromatography refers to column chromatography performed using 32–63 mm silica gel and executed under nitrogen pressure (flash chromatography) conditions. Low Resolution Mass Spectra (LRMS) were recorded on either a Hewlett Packard 5989®, utilizing chemical ionization (ammonium), or a Fisons (or Micro Mass) Atmospheric Pressure Chemical Ionization (APCI) platform which uses a 50/50 mixture of acetonitrile/ water with 0.1% formic acid as the ionizing agent. Room or ambient temperature refers to 20–25° C. All non-aqueous reactions were run under a nitrogen atmosphere for convenience and to maximize yields. Concentration at reduced pressure means that a rotary evaporator was used. The names for the compounds of the invention were created by the Autonom 2.0 PC-batch version from Beilstein Informationssysteme GmbH (ISBN 3-89536-976-4).

EXAMPLE 1

QUINOKINE-3-CARBOXYLIC ACID (1(S)-CYCLOHEXYLMETHYL-2(S)-HYDROXY-6-METHYL-4(R)-METHYLCARBAMOYL-HEPTYL-6-ENYL)-AMIDE

METHOD A

QUINOLINE-3-CARBOXYLIC ACID {1-[4-(2-METHYLPROPEN-2-YL)-5-OXO-TETRAHYDROFURAN-2-YL]-2-CYCLOHEXYL-ETHYL}-AMIDE

To a solution of 1-{4-(2-methylpropen-2-yl)-[5-oxo-tetrahydrofuran-2-yl]-2-cyclohexyl-ethyl}-carbamic acid tert-butyl ester (302 mg, 0.83 mmol)(prepared according to the method of Fray, supra, except that (S)-2-(tert-butoxycarbonylamino)-3-cyclohexyl-1-propionaldehyde is the starting material aldehyde) in 15 mL of methylene chloride was added 1.5 mL of trifluoroacetic acid. The mixture was stirred at room temperature under a nitrogen atmosphere for 2 hours at which time the solvent was removed by azeotropic distillation under reduced pressure, using toluene as a cosolvent during the distillation. The resulting crude oil was dissolved in methylene chloride (5 mL) and quinoline-3-carboxylic acid (219 mg, 1.26 mmol), hydroxybenzotriazole (HOBT)(188 mg, 1.39 mmol), triethylamine (0.25 mL, 1.80 mmol) and N-3-dimethylaminopropyl-N'-ethylcarbodiimide (EDC)(248 mg, 1.29 mmol) was added. The resulting mixture was stirred at room temperature for 16 hours. The solution was transferred to a separatory funnel with 15 mL of methylene chloride and washed with 10% citric acid, saturated sodium bicarbonate and brine. The organic layer was dried over sodium sulfate and the solvent removed in vacuo. The remaining crude oil was purified by silica gel chromatography eluting with 3:1 hexanes:ethyl acetate to provide quinoline-3-carboxylic acid {1(S)-[4(R)-(2-methylpropen-2-yl)-5-oxo-tetrahydrofuran-2(S)-yl]-2-cyclohexyl-ethyl}-amide as a white foam (236 mg, 67%).

LRMS: 421(MH+); $^1$H NMR (300 MHz, CDCl$_3$): $\delta$0.90–1.89 (m, 13H), 1.63 (s, 3H), 2.03–2.14 (m, 2H), 2.38 (m, 2H), 2.48 (d, 1H, J=14.6 Hz), 2.73 (m, 1H), 4.63 (m, 2H), 4.69 (s, 1H), 4.79 (s, 1H), 6.9 (brs, 1H), 7.59 (t, 1H, J=7.8 Hz), 7.77 (t, 1H), J=8.4 Hz), 7.88 (d, 1H, J=8.3 Hz), 8.08 (d, 1H, J=8.4 Hz), 8.67 (s, 1H), 9.37 (d, 1H, J=2.1 Hz).

METHOD B

QUINOLINE-3-CARBOXYLIC ACID (1(S)-CYCLOHEXYLMETHYL-2(S)-HYDROXY-6-METHYL-4(R)-METHYLCARBAMOYL-HEPTYL-6-ENYL)-AMIDE

Methylamine was bubbled into a solution of the product from Method A (55 mg, 0.129 mmol) in methanol (2.5 mL). The solution was stirred for 2 hours at room temperature and the solvent was removed under reduced pressure to provide the title compound (57 mg, 98%) as a pure white solid.

LRMS: 453 (MH+), 421, 283, 173; $^1$H NMR (300 MHz, CDCl$_3$): $\delta$0.82–1.87 (m, 13H), 1.65 (s, 3H), 2.13 (dd, 1H, J=14.1, 8.7 Hz), 2.38 (d, 1H, J=14.2 Hz), 2.71 (d, 3H, J=4.7 Hz), 2.74 (m, 1H), 3.77 (d, 1H, J=8.7), 4.23 (br, 1H), 4.69 (s, 1H), 4.72 (s, 1H), 5.03 (brs, 1H), 6.60 (q, 1H, J=4.7 Hz), 7.24 (d, 1H, J=9.3), 7.54 (t, 1H, J=7.1), 7.73 (t, 1H, J=7.1 Hz), 7.81 (d, 1H, J=7.1 Hz), 8.04 (d, 1H, J=8.4), 8.61 (d, 1H, J=1.9), 9.33 (s, 1H).

EXAMPLE 2

QUINOXALINE-2-CARBOXYLIC ACID (1(S)-BENZYL-4(R)-BENZYLCARBAMOYL-7-FLUORO-2(S)-HYDROXY-7-METHYL-OCTYL)-AMIDE ALLYLIC ALKYLATION

METHOD C

{1(S)-[4(R)-(3-METHYL-BUT-2-ENYL)-5-OXO-TETRAHYDRO-FURAN-2(S)-YL]-2-PHENYL-ETHYL}-CARBAMIC ACID TERT-BUTYL ESTER

To a flame dried round bottom flask under a nitrogen atmosphere was added tetrahydrofuran (40 mL) followed by 1,1,1,3,3,3-hexamethyldisilazane (8 mL, 37.8 mmol). The mixture was cooled to 0° C. and n-butyl lithium (14.5 mL of a 2.5 M solution in hexanes, 36.0 mmol) was added. The mixture was stirred for 15 minutes, then cooled to −78° C. in dry ice/acetone bath. {1(S)-[5-Oxo-tetrahydro-furan-2(S)-yl]-2-phenyl-ethyl}-carbamic acid tert-butyl ester (5 g, 16.4 mmol) (prepared by the method of Fray, *J. Org. Chem.*, (51) 4828 (1986)) dissolved in tetrahydrofuran (50 mL) was added dropwise via syringe and stirring continued for 30 minutes. A solution of 4-bromo-2-methyl-2-butene (2.07 mL, 18.0 mmol) in 40 mL of THF was added dropwise via syringe. Stirring was continued for 3 hours during which time the temperature rose to −60° C. The mixture was quenched by slow addition of saturated, aqueous ammonium chloride (25 mL). Upon warming to room temperature, the solution was diluted with ether (300 mL) and transferred to a separatory funnel. The organic phase was washed with saturated aqueous citric acid (2×100 mL), saturated aqueous sodium bicarbonate (NaHCO$_3$)(2×100 mL), and 100 mL brine. The organic layer was dried over magnesium sulfate (MgSO$_4$) and the solvent removed under reduced pressure. Thin layer chromatography in 1:2 hexane/diethyl ether (Et$_2$O) revealed product with an R$_f$ of 0.8. The resulting crude oil was chromatographed on silica gel (225 g) eluting with 2:1 hexanes/diethyl ether to provide 4.73 g (77%) of the title compound. TLC: 1:2 Hexanes/Et$_2$O R$_f$: 0.8. $^1$H NMR (400 MHz, CDCl$_3$): δ7.27 ppm (5H, m), 5.02 (1H, b), 4.52 (1H, d, J=9.3 Hz), 4.42 (1H, t, J=7.1 Hz), 3.98 (1H, dt, J=8.5, 7.8 Hz), 2.93 (2H, m), 2.88 (1H, b), 2.68 (1H, m), 2.41 (1H, m), 2.24 (1H, m), 1.92 (1H, m), 1.65 (3H,s), 1.58 (3H,s), 1.37 (9H, s).

METHOD D

5(S)-(1(S)-AMINO-2-PHENYL-ETHYL)-3(R)-(3-FLUORO-3-METHYL-BUTYL)-DIHYDRO-FURAN-2-ONE

To a solution of product from Method C (9.81 g, 26.3 mmol) in dry benzene (300 mL) was added HF.pyridine (88 mL). The resulting solution was stirred at ambient temperature for 4 hours, then transferred to a 4 L beaker. To this was added ice, and the pH was slowly adjusted to 8–9 by addition of 2 M aqueous sodium hydroxide (NaOH$_{aq}$). The mixture was extracted with ethyl acetate (EtOAc) and the organics dried over magnesium sulfate, and then filtered and concentrated. Chromatography on silica gel yielded the title compound (5.68 g, 74%).

METHOD E

QUINOXALINE-2-CARBOXYLIC ACID {1(S)-[4(R)-(3-FLUORO-3-METHYL-BUTYL)-5-OXO-TETRAHYDRO-FURAN-2(S)-YL]-2-PHENYL-ETHYL}-AMIDE

To a solution of quinoxaline carboxylic acid (5.05 g, 29.0 mmol) in methylene chloride (100 mL) was added dimethylaminopyridine (DMAP) (3.55 g, 29.0 mmol) and EDCl (5.55 g, 29.0 mmol). The solution was stirred 10 minutes, then the product from Method D, above, (5.68 g, 19.4 mmol) was added in one portion. The solution was stirred for 12 hours, then diluted with diethyl ether and washed with saturated aqueous brine. The organics were dried over magnesium sulfate, and then filtered and concentrated. The crude product was purified by silica gel chromatography to yield the title compound (5.62 g, 64%).

METHOD F

QUINOXALINE-2-CARBOXYLIC ACID (1(S)-BENZYL-4(R)-BENZYLCARBAMOYL-7-FLUORO-2(S)-HYDROXY-7-METHYL-OCTYL)-AMIDE

To a solution of the product from Method E (0.10 g, 0.22 mmol) in dioxane (2 mL) was added glacial acetic acid (0.038 mL, 0.66 mmol) and benzylamine (approx. 1 mL, excess). The resulting solution was warmed to reflux for 1 hour, cooled to ambient temperature and diluted with water. The solution was extracted with ethyl acetate and the combined organics were dried over magnesium sulfate (MgSO$_4$), filtered and concentrated. Chromatography on silica gel, followed by recrystallization from methylene chloride/hexanes gave the title compound (0.068 g, 56%). m.p. 183–184° C.

EXAMPLE 3

METHOD F'

QUINOXALINE-2-CARBOXYLIC ACID (1-BENZYL-7-FLUORO-2-HYDROXY-4-HYDROXYCARBAMOYL-7-METHYL-OCTYL)-AMIDE

Hydroxylamine hydrochloride (1.55 g, 22.4 mmol) and KOH (1.51 g, 26.7 mmol) were combined in anhydrous methanol (20 mL) and stirred for 30 minutes under a dry nitrogen atmosphere, and then filtered. To the resulting filtrate was added the product from Method E (500 mg, 1.17 mmol) and the reaction mixture was stirred for 16 hours at room temperature. The solvent was removed in vacuo and the residue solvated in EtOAc (50 mL) and transferred to a separated funnel. The organic layer was washed with water and brine and dried (MgSO4). After filtration the solvent was removed in vacuo and the remaining residue recrystallized (methylene chloride/Hexanes) to give a pale yellow solid (330 mg, 58%) m.p. 165–166° C.

EXAMPLE 4

QUINOXALINE-2-CARBOXYLIC ACID (1(S)-BENZYL-4(R)-CARBAMOYL-2(S)-HYDROXY-7-METHYL-OCTYL)-AMIDE

METHOD G

ALKENE HYDROGENATION {1(S)-[4(R)-(3-METHYL-BUTYL)-5-OXO-TETRAHYDRO-FURAN-2(S)-YL]-2-PHENYL-ETHYL}-CARBAMIC ACID TERT-BUTYL ESTER

The product from Method C, from Example 2 above, (3.0 g, 8.04 mmol) was placed in a 250 mL Parr Shaker bottle and dissolved in ethanol (50 mL). Under a nitrogen atmosphere, Palladium (Pd) on activated carbon (0.30 g, 10% Pd content) was added to the solution. The mixture was placed on a Parr Shaker hydrogenator at 50 psi for 5 hours at room temperature. The hydrogenation mixture was diluted with ethyl acetate and then poured through a Celite® pad while washing copiously with ethyl acetate. The solvent of the filtrate was removed in vacuo to yield the title compound, 2.63 g (88%).

$^1$H NMR (400 MHz, CDCl$_3$): δ7.27 (5H, m), 4.54 (1H, d, J=9.8 Hz), 4.46 (1H, t, J=6.9), 4.0 (1H, dt), 2.89 (2H, d, J=8.1), 2.57 (1H, m), 2.32 (1H, b), 1.89 (1H, m), 1.79 (1H, m), 1.52 (2H, m), 1.37 (9H, s), 1.23 (2H, m), 0.86 (6H, d, J=6.6 Hz).

The product from Method G was converted into the title compound by procedures analogous to those of Methods A and B except that quinoline-3-carboxylic acid is replaced with quinoxaline-2-carboxylic acid and methylamine is replaced with ammonia gas to yield 0.095 g (72%) of the title compound.

$^1$H NMR (400 MHz, CDCl$_3$): δ9.61(1H, s), 8.32 (1H, d, J=8.9 Hz), 8.16 (2H, m), 7.86 (2H,m), 7.28 (10H, m), 7.19 (1H, m), 5.70 (1H, b), 5.29 (1H, b), 4.27 (1H, m), 8.21 (1H, d, J=4.4 Hz), 3.91 (1H, m), 3.11 (2H, m), 2.46 (1H, m), 1.74 (1H, t, J=6.4 Hz), 1.61 (1H, m), 1.42 (2H, m), 1.17 (1H, m), 1.09 (1H, m), 0.81 (3H, d, J=7.1 Hz), 0.79 (3H, d, J=7.1 Hz). $^{13}$C NMR (100 MHz, CDCl$_3$): d 179.11, 163.73, 143.90, 143.76, 143.15, 140.28, 137.96, 131.68, 130.84, 129.84, 129.44, 129.25, 128.58, 126.60, 68.55, 55.90, 43.44, 38.39, 36.90, 36.70, 29.77, 28.03, 22.42

EXAMPLE 5

QUINOXALINE-2-CARBOXYLIC ACID 1(S)-BENZYL-4(R)-CARBAMOYL-2(S)-HYDROXY-7,7-DIMETHYL-OCTYL)-AMIDE

METHOD H

TRIFLATE ALKYLATION {1-[4-(3,3-DIMETHYL-BUTYL)-5-OXO-TETRAHYDRO-FURAN-2-YL]-2-PHENYL-ETHYL}-CARBAMIC ACID TERT-BUTYL ESTER

To a flame dried round bottom flask under a nitrogen atmosphere was added terahydrofuran (THF) (2 mL) and 1,1,1,3,3,3 hexamethyldisilazane (0.82 mL, 3.88 mmol). The mixture was cooled to 0° C. and n-butyl lithium (1.48 mL of a 2.5 M solution in hexanes, 3.72 mmol) was added dropwise via syringe. The mixture was stirred for 15 minutes and then cooled to −78° C. {1(S)-[5-Oxo-tetrahydro-furan-2(S)-yl]-2-phenyl-ethyl}-carbamic acid tert-butyl ester (0.52 g, 1.69 mmol prepared by the method of Fray, supra) dissolved in tetrahydrofuran (2 mL) was slowly added to the solution via syringe and the solution was stirred for 1 hour. A solution of the desired triflate, i.e. 3,3-dimethylbutyl triflate (0.92 g, 3.37 mmol)(prepared according to the method of Beard, et al., J Org Chem., 38, 3673 (1973)) in tetrahydrofuran (2 mL) was added dropwise via syringe and the mixture was stirred for 2 hours at −78° C. The mixture was quenched by addition of saturated aqueous ammonium chloride (NH$_4$Cl) (25 mL). Upon warming to room temperature, the mixture was diluted with ethyl acetate (40 mL), transferred to a separatory funnel, and washed with saturated aqueous NH$_4$Cl (2×40 mL), saturated NaHCO$_3$ (2×40 mL), and brine (40 mL). The organic layers were dried (MgSO$_4$) and the solvent removed under reduced pressure. The resulting crude oil was chromatographed on silica gel (25 g) eluting with 100 mL 5:1 hexanes/ethyl acetate followed by 400 mL 4:1 hexanes/ethyl acetate. This provided 0.36 g (50%) of the title compound.

TLC: (4:1 hexanes/ethyl acetate) R$_f$: 0.3. $^1$H NMR (400 MHz, CDCl$_3$): δ7.25 (m, 7H), 6.92 (t, 1H, J=7.5 Hz), 6.85 (d, 2H, J=8.1 Hz), 4.67 (d, 2H, J=6.0 Hz), 4.49 (t, 1H, J=9.6 Hz), 4.06 (m, 3H), 2.89 (m, 3H), 2.43 (m, 1H), 2.26 (m, 1H), 2.05 (m, 1H), 1.95 (m, 1H), 1.37 (s, 9H).

The product of Method H was converted to the title compound by procedures analogous to those of Methods A and B, from Example 1, except that quinoline-3-carboxylic acid is replaced with quinoxaline-2-carboxylic acid and methylamine is replaced with ammonia gas.

EXAMPLE 6

QUINOXALINE-2-CARBOXYLIC ACID [1(S)-BENZYL-4(S)-CARBAMOYL-2(S)-HYDROXY-4-(1-HYDROXY-CYCLOHEXYL)-BUTYL]-AMIDE AND

QUINOXALINE-2-CARBOXYLIC ACID [1(S)-BENZYL-4(R)-CARBAMOYL-2(S)-HYDROXY-4-(1-HYDROXY-CYCLOHEXYL)-BUTYL]-AMIDE

METHOD I

{1(S)-[4(S)-(1-HYDROXY-CYCLOHEXYL)-5-OXO-TETRAHYDRO-FURAN-2(S)-YL]-2-PHENYL-ETHYL}-CARBAMIC ACID TERT-BUTYL ESTER

To a solution of diisopropylamine (0.90 mL, 6.88 mmol) in THF (10 mL) at 0° C. was added a solution of n-butyl lithium (2.7 mL, 6.71 mmol, 2.5 M in hexanes). The solution was stirred for 15 minutes, then cooled to −78° C. To this was added dropwise a solution of {1(S)-[5-Oxo-tetrahydro-furan-2(S)-yl]-2-phenyl-ethyl}-carbamic acid tert-butyl ester (1.0 g, 3.27 mmol prepared as in example 2, method C) in tetrahydrofuran (10 mL) and the reaction was stirred an additional 30 minutes. To this was added the appropriate ketone, e.g., cyclohexanone) (0.37 mL, 3.60 mmol), and the solution was warmed to ambient temperature. The reaction was quenched by addition of saturated aqueous bicarbonated NaHCO$_3$) solution and the mixture extracted with diethyl ether. The combined organics were dried over magnesium sulfate (MgSO4), filtered and concentrated. Chromatography on silica gel gave a mixture of separable diastereomers of {[1(S)-[4(S)-(1-hydroxy-cyclohexyl)-5-oxo-tetrahydro-furan-2(S)-yl]-2-phenyl-ethyl}-carbamic acid tert-butyl ester (0.687 g) and {1(S)-[4(R)-(1-hydroxy-cyclohexyl)-5-oxo-tetrahydro-furan-2(S)-yl]-2-phenyl-ethyl}-carbamic acid tert-butyl ester (0.269 g) in 67% overall yield.

The products from Method I were converted to the title compounds by procedures analogous to those of Methods A and B, from Example 1, except that quinoline-3-carboxylic acid is replaced with quinoxaline-2-carboxylic acid and methylamine is replaced with ammonia gas.

EXAMPLE 7

FLUORO-QUINOLINE-3-CARBOXYLIC ACID (1(S)-BENZYL4(S)-CARBAMOYL-4-CYCLOHEXYL-2(S)-HYDROXY-BUTYL)-AMIDE AND

FLUORO-QUINOLINE-3-CARBOXYLIC ACID (1(S)-BENZYL4(R)-CARBAMOYL-4-CYCLOHEXYL-2(S)-HYDROXY-BUTYL)-AMIDE

METHOD J

{1(S)-[4(S)-(1-HYDROXY-CYCLOHEXYL)-5-OXO-TETRAHYDRO-FURAN-2(S)-YL]-2-PHENYL-ETHYL}-CARBAMIC ACID TERT-BUTYL ESTER

To a solution of the title compound from Method I, Example 5, (1.38 g, 3.42 mmol) in benzene (40 mL) was added (methoxycarbonylsulfamoyl)-triethylammonium hydroxide, inner salt (Burgess reagent) (1.30 g, 5.47 mmol) and the solution was warmed to reflux for 2 hours. The reaction was diluted with diethyl ether and washed with saturated aqueous brine. The organics were dried over magnesium sulfate, filtered and concentrated to give the crude elimination product. This was directly dissolved in 5:1 tetrahydrofuran/methanol (THF/MeOH) (30 mL) and transferred to a Parr flask containing 10% palladium on carbon (Pd/C) (1 g). The mixture was hydrogenated at 35 psi for 1.5 hours, then filtered through a pad of Celite and the filtrate concentrated. Chromatography on silica gel yielded the title compound as a mixture of separable diastereomers {1(S)-[4(S)-(1-hydroxy-cyclohexyl)-5-oxo-tetrahydro-furan-2(S)-yl]-2-phenyl-ethyl}-carbamic acid tert-butyl ester (0.53 g) and {1(S)-[4(R)-(1-hydroxy-cyclohexyl)-5-oxo-tetrahydro-furan-2(S)-yl]-2-phenyl-ethyl}-carbamic acid tert-butyl ester (0.29 g) in 62% overall yield.

The products from Method J were converted to the title compounds by procedures analogous to those of Methods A and B, from Example 1, except that quinoline-3-carboxylic acid is replaced with quinoxaline-2-carboxylic acid and methylamine is replaced with ammonia gas.

EXAMPLES 8–312

The compounds from Table 1 were prepared according to the methods described above, substituting where appropriate the correct $R^2$ aldehyde, $R^3$ group (such as allylic halide, alkyl triflate, ketone, etc.), $R^1$ carboxylic acid or $R^4$ and $R^5$ amine where appropriate.

TABLE 1

| EXAMPLE | NAME | M.P. (° C.) | LRMS |
|---|---|---|---|
| 8. | Quinoxaline-2-carboxylic acid 1(S)-cyclohexylmethyl-2(S)-hydroxy-6-methyl-4(R)-methylcarbamoyl-heptyl)-amide | | 455 |
| 9. | Quinoxaline-2-carboxylic acid (6-chloro-1-cyclohexylmethyl-2(S)-hydroxy-4(S)-methylcarbamoyl-hept-6-enyl)-amide | | |
| 10. | Quinoline-3-carboxylic acid (2(S)-hydroxy-1(S)-isobutyl-6-methyl-4(R)-methylcarbamoyl-heptyl)-amide | 155–157 | 414 |
| 11. | Quinoxaline-2-carboxylic acid 1(S)-sec-butyl-2(S)-hydroxy-6-methyl-4(R)-methylcarbamoyl-heptyl)-amide | 69–71 | 415 |
| 12. | Quinoline-3-carboxylic acid 1(S)-cyclohexylmethyl-2(S)-hydroxy-6-methyl-4(R)-methylcarbamoyl-hept-6-enyl)-amide | | 452 |
| 13. | Quinoxaline-2-carboxylic acid 1(S)-cyclohexylmethyl-2(S)-hydroxy-6-methyl-4(R)-methylcarbamoyl-hept-6-enyl)-amide | | 453 |
| 14. | N-1(S)-Cyclohexylmethyl-2(S)-hydroxy-6-methyl-4(R)-methylcarbamoyl-heptyl)-5-phenyl-nicotinamide | 115–119 | |
| 15. | Quinoline-3-carboxylic acid 1(S)-benzyl-2(S)-hydroxy-6-methyl-4(R)-methylcarbamoyl-heptyl)-amide | 162–163 | |
| 16. | Quinoxaline-2-carboxylic acid 1(S)-cyclohexylmethyl-4(R)-dimethylcarbamoyl-2(S)-hydroxy-6-methyl-hept-6-enyl)-amide | | 467 |
| 17. | Quinoline-3-carboxylic acid 1(S)-cyclohexylmethyl-2(S)-hydroxy-6-methyl-4(S)-methylcarbamoyl-heptyl)-amide | 171–175 | 453, 436 |
| 18. | Quinoxaline-2-carboxylic acid 1(S)-cyclohexylmethyl-2(S)-hydroxy-6-methyl-4(S)-methylcarbamoyl-heptyl)-amide | | 455, 437 |
| 19. | Isoquinoline-4-carboxylic acid 1(S)-cyclohexylmethyl-2(S)-hydroxy-6-methyl-4(S)-methylcarbamoyl-heptyl)-amide | 180–182 | 454 |
| 20. | Quinoline-3-carboxylic acid (4(R)carbamoyl-1(S)-cyclohexylmethyl-2(S)-hydroxy-6-methyl-heptyl)-amide | 186–188 | 440, 478, 423 |
| 21. | Quinoline-3-carboxylic acid (5-cyclohexyl-1(S)-cyclohexylmethyl-2(S)-hydroxy-4(R)-methylcarbamoyl-pentyl)-amide | 170.5–172.5 | 494 |
| 22. | Quinoline-3-carboxylic acid 1(S)-cyclohexylmethyl-2(S)-hydroxy-6-methyl-4(R)-methylcarbamoyl-heptyl)-amide | | 454 |
| 23. | Quinoline-3-carboxylic acid 1(S)-cyclohexylmethyl-2(S)-hydroxy-6-methyl-4(S)-methylcarbamoyl-heptyl)-amide | 200–201.5 | 454 |
| 24. | Quinoline-3-carboxylic acid 1(S)-cyclohexylmethyl-2(S)-hydroxy-4(R)-methylcarbamoyl-5-phenyl-pentyl)-amide | 199–200.5 | 488 |
| 25. | Quinoxaline-2-carboxylic acid 1(S)-cyclohexylmethyl-2(S)-hydroxy-4(R)-methylcarbamoyl-5-phenyl-pentyl)-amide | 109–110.5 | 489 |
| 26. | Quinoline-3-carboxylic acid 1(S)-benzyl-4(R)-butylcarbamoyl-2(S)-hydroxy-6-methyl-heptyl)-amide | 142–144 | 490, 417 |
| 27. | Quinoline-3-carboxylic acid 1(S)-benzyl-4(R)-cyclobutylcarbamoyl-2(S)-hydroxy-6-methyl-heptyl)-amide | 148–150 | 488, 417 |
| 28. | Quinoline-3-carboxylic acid 1(S)-benzyl-4(R)-benzylcarbamoyl-2(S)-hydroxy-6-methyl-heptyl)-amide | 158–162 | 524 417 |
| 29. | Quinoline-3-carboxylic acid 1(S)-benzyl-4(R)-cyclopropylcarbamoyl-2(S)-hydroxy-6-methyl-heptyl)-amide | 174–179 | 474 |
| 30. | Quinoline-3-carboxylic acid 1(S)-benzyl-2(S)-hydroxy-6-methyl-4(S)-methylcarbamoyl-heptyl)-amide | 190–192.5 | 448 |
| 31. | Quinoline-3-carboxylic acid 1(S)-benzyl-4(R)-ethylcarbamoyl-2(S)-hydroxy-6-methyl-heptyl)-amide | 175–176 | 462 |
| 32. | Quinoline-3-carboxylic acid 1(S)-benzyl-2(S)-hydroxy-6-methyl-4(R)-propylcarbamoyl-heptyl)-amide | | 476 |
| 33. | Quinoline-3-carboxylic acid [1-benzyl-2(S)-hydroxy-4(R)-(2-hydroxy-ethylcarbamoyl)-6-methyl-heptyl]-amide | 158–162 | 478 |
| 34. | Cinnoline-4(R)-carboxylic acid 1(S)-benzyl-2(S)-hydroxy-6-methyl-4(R)-methylcarbamoyl-heptyl)-amide | 185–186.5 | 449 |
| 35. | Isoquinoline-4-carboxylic acid 1(S)-benzyl-2(S)-hydroxy-6-methyl-4(R)-methylcarbamoyl-heptyl)-amide | 200–201 | 448 |
| 36. | Quinoxaline-2-carboxylic acid 1(S)-benzyl-2(S)-hydroxy-6-methyl-4(R)-methylcarbamoyl-heptyl)-amide | 166–167 | 449 |
| 37. | N-1(S)-Benzyl-2(S)-hydroxy-6-methyl-4(R)-methylcarbamoyl-heptyl)-5-bromo-nicotinamide | 184.5–185.5 | 478 |
| 38. | Quinoline-3-carboxylic acid 1(R)-cyclohexylmethyl-2(R)-hydroxy-6-methyl-4(S)-methylcarbamoyl-heptyl)-amide | | 454 |

TABLE 1-continued

| EXAMPLE | NAME | M.P. (° C.) | LRMS |
|---|---|---|---|
| 39. | Quinoxaline-2-carboxylic acid [1(S)-(4-benzyloxy-benzyl)-2(S)-hydroxy-6-methyl-4(R)-methylcarbamoyl-heptyl]-amide, | 196–197 | 554 |
| 40. | Quinoline-3-carboxylic acid [1(S)-(4-benzyloxy-benzyl)-2(S)-hydroxy-6-methyl-4(R)-methylcarbamoyl-heptyl]-amide | 178–179 | 555 |
| 41. | Isoquinoline-1-carboxylic acid 1(S)-benzyl-2(S)-hydroxy-6-methyl-4(R)-methylcarbamoyl-heptyl)-amide | 178–179 | 448 |
| 42. | Quinoline-4-carboxylic acid 1(S)-benzyl-2(S)-hydroxy-6-methyl-4(R)-methylcarbamoyl-heptyl)-amide | 189–192 | 448 |
| 43. | Quinoline-6-carboxylic acid 1(S)-benzyl-2(S)-hydroxy-6-methyl-4(R)-methylcarbamoyl-heptyl)-amide | 165–167 | 448 |
| 44. | Quinoline-3-carboxylic acid [2(S)-hydroxy-1(S)-(4-hydroxy-benzyl)-6-methyl-4(R)-methylcarbamoyl heptyl]-amide | 220.5–222.5 | 464 |
| 45. | Quinoline-2-carboxylic acid 1(S)-benzyl-2(S)-hydroxy-6-methyl-4(R)-methylcarbamoyl-heptyl)-amide | 160–161.5 | 449 |
| 46. | Naphthalene-2-carboxylic acid 1(S)-benzyl-2(S)-hydroxy-6-methyl-4(R)-methylcarbamoyl-heptyl)-amide | 218–220 | 447 |
| 47. | Quinoline-3-carboxylic acid 1(S)-benzyl-5-cyclohex-1-enyl-2(S)-hydroxy-4(R)-methylcarbamoyl-pentyl)-amide | 172–174 | 486 |
| 48. | Quinoline-3-carboxylic acid [1(S)-benzyl-2(S)-hydroxy-6-methyl-4(R)-(3-methyl-butylcarbamoyl)-heptyl]-amide | 153–154 | 504 |
| 49. | Quinoxaline-2-carboxylic acid 1(S)-benzyl-2(S)-hydroxy-6-methyl-4(S)-methylcarbamoyl-heptyl)-amide | 157–163 | 449 |
| 50. | Trifluoro-methanesulfonic acid 4-{3(S)-hydroxy-7-methyl-5(R)-methylcarbamoyl-2(S)-[(quinoline-3-carbonyl)-amino]-octyl}-phenyl ester | 168–170 | 596 |
| 51. | Trifluoro-methanesulfonic acid 4-{3(S)-hydroxy-7-methyl-5(R)-methylcarbamoyl-2(S)-[(quinoxaline-2-carbonyl)-amino)-octyl]-phenyl ester | | 597 |
| 52. | Quinoline-3-carboxylic acid 1(S)-benzyl-5-cyclohexyl-2(S)-hydroxy-4(R)-methylcarbamoyl-pentyl)-amide | 185–187 | 488 |
| 53. | Quinoxaline-2-carboxylic acid 1(S)-benzyl(-5-cyclohexyl-2(S)-hydroxy-4(R)-methylcarbamoyl-pentyl)-amide | 132–134 | 489, 471 |
| 54. | Isoquinoline-3-carboxylic acid 1(S)-benzyl-5-cyclohexyl-2(S)-hydroxy-4(R)-methylcarbamoyl-pentyl)-amide | 150.5–151.5 | 488 |
| 55. | N-1(S)-Benzyl-5-cyclohexyl-2(S)-hydroxy-4(R)-methylcarbamoyl-pentyl)-5-bromo-nicotinamide | 199–200.5 | 518 |
| 56. | Quinoline-3-carboxylic acid 1(S)-benzyl-2(S)-hydroxy-6-methyl-4(R)-prop-2-ynylcarbamoyl-heptyl)-amide | | 472 |
| 57. | Quinoline-3-carboxylic acid 1(S)-cyclohexylmethyl-2(S)-hydroxy-4(R)-hydroxycarbamoyl-6-methyl-heptyl)-amide | | 456, 438, 423 |
| 58. | Quinoline-3-carboxylic acid 2(S)-hydroxy-1(S)-(4-methoxy-benzyl)-6-methyl-4(R)-methylcarbamoyl-hepty]-amide | 176–177 | 478 |
| 59. | Isoquinoline-3-carboxylic acid (5-cyclohexyl-1(S)-cyclohexylmethyl-2(S)-hydroxy-4(R)-methylcarbamoyl-pentyl)-amide | 205–207 | 494 |
| 60. | 5-Bromo-N-(5-cyclohexyl-1(S)-cyclohexylmethyl-2(S)-hydroxy-4(R)-methylcarbamoyl-pentyl)-nicotinamide | 173.5–175 | 444 |
| 61. | Quinoxaline-2-carboxylic acid [2(S)-hydroxy-1(S)-(4-methoxy-benzyl)-6-methyl-4(R)-methylcarbamoyl-heptyl]-amide | | 479 |
| 62. | Isoquinoline-4-carboxylic acid (5-cyclohexyl-1(S)-cyclohexylmethyl-2(S)-hydroxy-4(R)-methylcarbamoyl-pentyl)-amide | 220.5–224 | 494 |
| 63. | Quinoline-2-carboxylic acid 1(S)-benzyl-5-cyclohexyl-2(S)-hydroxy-4(R)-methylcarbamoyl-pentyl)-amide | 120–122 | 488 |
| 64. | Isoquinoline-4-carboxylic acid 1(S)-benzyl-5-cyclohexyl-2(S)-hydroxy-4(R)-methylcarbamoyl-pentyl)-amide, | 177–180 | 488 |
| 65. | Quinoxaline-2-carboxylic acid [2(S)-hydroxy-1(S)-(4-hydroxy-benzyl)-6-methyl-4(R)-methylcarbamoyl-heptyl]-amide, | 170–172 | 465 |
| 66. | Quinoxaline-2carboxylic acid (5-cyclohexyl-1 (S)-cyclohexylmethyl-2(S)-hydroxy-4(R)-methyl carbamoyl-pentyl)-amide | | 496 |
| 67. | Quinoline-3-carboxylic acid [1(S)-(4-chloro-benzyl)-2(S)-hydroxy-6-methyl-4(R)-methylcarbamoyl-heptyl]-amide | 212.5–213.5 | 482 |
| 68. | Quinoxaline-2-carboxylic acid [1(S)-(4-chloro-benzyl)-2(S)-hydroxy-6-methyl-4(R)-methylcarbamoyl-heptyl]-amide | | 483 |
| 69. | Quinoline-3-carboxylic acid 1(S)-cyclohexylmethyl-2(S)-hydroxy-7-methyl-4(R)-methylcarbamoyl-octyl)-amide | 173.5–175 | 468, 450 |
| 70. | Quinoxaline-2-carboxylic acid 1(S)-cyclohexylmethyl-2(S)-hydroxy-7-methyl-4(R)-methylcarbamoyl-octyl)-amide | 78–80 | 470 |
| 71. | Quinoline-3-carboxylic acid [1(S)-(4-chloro-benzyl)-5-cyclohexyl-2(S)-hydroxy-4(R)-methylcarbamoyl-pentyl]-amide | 198–201 | 522 |
| 72. | Quinoxaline-2-carboxylic acid [1(S)-(4-chloro-benzyl)-5-cyclohexyl-2(S)-hydroxy-4(R)-methylcarbamoyl-pentyl]-amide | | 523 |
| 73. | Quinoline-2-carboxylic acid [1(S)-(4-chloro-benzyl)-5-cyclohexyl-2(S)-hydroxy-4(R)-methylcarbamoyl-pentyl]-amide | | 522 |
| 74. | Benzofuran-2-carboxylic acid 1(S)-benzyl-2(S)-hydroxy-6-methyl-4(R)-methylcarbamoyl-heptyl)-amide | 181–183 | 437 |
| 75. | N-1(S)-Benzyl-2(S)-hydroxy-6-methyl-4(R)-methylcarbamoyl-heptyl)-5,6-dichloro-nicotinamide | 195–196 | 466, 432 |
| 76. | Quinoline-3-carboxylic acid 1(S)-benzyl-2(S)-hydroxy-7-methyl-4(R)-methylcarbamoyl-octyl)-amide | 188–190 | 462 |
| 77. | N-1(S)-Benzyl-2(S)-hydroxy-7-methyl-4(R)-methylcarbamoyl-octyl)-5-bromo-nicotinamide | 188–189 | 490 |
| 78. | 5,6,7,8-Tetrahydro-quinoline-3-carboxylic acid 1(S)-benzyl-2(S)-hydroxy-6-methyl-4(R)-methylcarbamoyl-heptyl)-amide | 142.5–144.5 | 452 |

TABLE 1-continued

| EXAMPLE | NAME | M.P. (° C.) | LRMS |
|---|---|---|---|
| 79. | Quinoxaline-2-carboxylic acid 1(S)-benzyl-2(S)-hydroxy-7-methyl-4(R)-methylcarbamoyl-octyl)-amide | 147–149 | 463 |
| 80. | Quinoline-2-carboxylic acid 1(S)-benzyl-2(S)-hydroxy-7-methyl-4(R)-methylcarbamoyl-octyl)-amide, | 156–158 | 462 |
| 81. | Isoquinoline-4-carboxylic acid 1(S)-benzyl-2(S)-hydroxy-7-methyl-4(R)-methylcarbamoyl-octyl)-amide | 199–202 | 462 |
| 82. | Quinoxaline-2-carboxylic acid [1(S)-(3,4-dichloro-benzyl)-2(S)-hydroxy-6-methyl-4(R)-methylcarbamoyl-heptyl]-amide | | 517, 483 |
| 83. | Benzo[b]thiophene-2-carboxylic acid 1(S)-benzyl-2(S)-hydroxy-6-methyl-4(R)-methylcarbamoyl-heptyl)-amide | 179–181 | 453 |
| 84. | 2-Methyl-quinoline-3-carboxylic acid 1(S)-benzyl-2(S)-hydroxy-6-methyl-4(R)-methylcarbamoyl-heptyl)-amide | 225–226.5 | 462 |
| 85. | 6,7-Dimethoxy-quinoline-3-carboxylic acid 1(S)-benzyl-2(S)-hydroxy-6-methyl-4(R)-methylcarbamoyl-heptyl)-amide | 211–214 | 508 |
| 86. | 6,7-Difluoro-quinoline-3-carboxylic acid 1(S)-benzyl-2(S)-hydroxy-6-methyl-4(R)-methylcarbamoyl-heptyl)-amide | 187–189 | 484, 466 |
| 87. | 1H-Benzoimidazole-2-carboxylic acid 1(S)-benzyl-2(S)-hydroxy-6-methyl-4(R)-methylcarbamoyl-heptyl)-amide | 136–140 | 437 |
| 88. | 5-Methyl-pyrazine-2-carboxylic acid 1(S)-benzyl-2(S)-hydroxy-6-methyl 4(R)-methylcarbamoyl-heptyl)-amide | 171.5–172.5 | 413 |
| 89. | Quinoline-3-carboxylic acid [1(S)-(4-fluoro-benzyl)-2(S)-hydroxy-6-methyl-4(R)-methylcarbamoyl-heptyl]-amide | 184–186 | 466 |
| 90. | Quinoxaline-2-carboxylic acid [1(S)-(4-fluoro-benzyl)-2(S)-hydroxy-6-methyl-4(R)-methylcarbamoyl-heptyl)-amide | 153–156 | 467 |
| 91 | 5-Chloro-1H-indole-2-carboxylic acid 1(S)-benzyl-2(S)-hydroxy-6-methyl-4(R)-methylcarbamoyl-heptyl)-amide | 245–247 | 470 |
| 92. | Quinoxaline-2-carboxylic acid 1 S)-benzyl-4(R)-carbamoyl-2(S)-hydroxy-7-methyl-octyl)-amide | 194–194.5 | 449, 432 |
| 93. | 2-Methoxy-quinoline-3-carboxylic acid 1(S)-benzyl-2(S)-hydroxy-6-methyl-4(R)-methylcarbamoyl-heptyl)-amide, | 175–181 | 478 |
| 94. | 5,6-Dichloro-1H-benzoimidazole-2-carboxylic acid 1(S)-benzyl-2(S)-hydroxy-6-methyl-4(R)-methylcarbamoyl-heptyl)-amide | 114–117 | 505 |
| 95. | Benzothiazole-2-carboxylic acid 1(S)-benzyl-2(S)-hydroxy-6-methyl-4(R)-methylcarbamoyl-heptyl)-amide | 86–89 | 454 |
| 96. | 7,8-Difluoro-quinoline-3-carboxylic acid 1(S)-benzyl-2(S)-hydroxy-6-methyl-4(R)-methylcarbamoyl-heptyl)-amide | 179–182 | 484 |
| 97. | 6,7,8-Trifluoro-quinoline-3-carboxylic acid 1(S)-benzyl-2(S)-hydroxy-6-methyl-4(R)-methylcarbamoyl-heptyl)-amide | 156–161 | 502, 484 |
| 98. | 5,8-Dimethyl-quinoline-3-carboxylic acid 1(S)-benzyl-2(S)-hydroxy-6-methyl-4(R)-methylcarbamoyl-heptyl)-amide | 197–199 | 476 |
| 99. | Quinoxaline-2-carboxylic acid 1(S)-benzyl-4(R)-butylcarbamoyl-2(S)-hydroxy-7-methyl-octyl)-amide | 103–106 | 505 |
| 100. | Quinoline-3-carboxylic acid [1(S)-(3,4-dichloro-benzyl)-2(S)-hydroxy-6-methyl-4(R)-methylcarbamoyl-heptyl]-amide | | 516 |
| 101. | 5,6,7,8-Tetrahydro-quinoline-3-carboxylic acid 1(S)-benzyl-2(S)-hydroxy-7-methyl-4(R)-methylcarbamoyl-octyl)-amide | 169.5–172.5 | 466 |
| 102. | Quinoline-3-carboxylic acid 1(S)-benzyl-5-cyclopentyl-2(S)-hydroxy-4(R)-methylcarbamoyl-pentyl)-amide | 176–178 | 474 |
| 103. | Quinoxaline-2-carboxylic acid 1(S)-benzyl-5-cyclopentyl-2(S)-hydroxy-4(R)-methylcarbamoyl-pentyl)-amide | 120–122 | 475 |
| 104. | N-1(S)-Benzyl-5-cyclopentyl-2(S)-hydroxy-4(R)-methylcarbamoyl-pentyl)-5-bromo-nicotinamide | 194–198 | 504 |
| 105. | 5,6,7,8-Tetrahydro-quinoline-3-carboxylic acid 1(S)-benzyl-5-cyclopentyl-2(S)-hydroxy-4(R)-methylcarbamoyl-pentyl)-amide, | 143–146 | 478 |
| 106. | Quinoxaline-2-carboxylic acid 1(S)-benzyl-4(R)-carbamoyl-5-cyclopentyl-2(S)-hydroxy-pentyl)-amide | 217–219 | 461, 444 |
| 107. | 6,7-Dihydro-5H-[1]pyrindine-3-carboxylic acid 1(S)-benzyl-2(S)-hydroxy-7-methyl-4(R)-methylcarbamoyl-octyl)-amide | 154.5–156 | 452, 349 |
| 108. | Quinoxaline-2-carboxylic acid [1(S)-(4,4-difluoro-cyclohexylmethyl)-2(S)-hydroxy-6-methyl-4(R)-methylcarbamoyl-heptyl]-amide | 95–98 | 491, 473 |
| 109. | Quinoxaline-2-carboxylic acid [1(S)-(4,4-difluoro-cyclohexylmethyl)-2(S)-hydroxy-7-methyl-4(R)-methylcarbamoyl-octyl]-amide | 95–98 | 506, 488 |
| 110. | Quinoxaline-2-carboxylic acid 1(S)-benzyl-4(R)-ethylcarbamoyl-2(S)-hydroxy-7-methyl-octyl)-amide | 129–133 | 478 |
| 111. | Quinoxaline-2-carboxylic acid 1(S)-benzyl-2(S)-hydroxy-7-methyl-4(R)-propylcarbamoyl-octyl)-amide | 125–130 | 492 |
| 112. | Quinoxaline-2-carboxylic acid 1(S)-benzyl-4(R)-cyclopropylcarbamoyl-2(S)-hydroxy-7-methyl-octyl)-amide | 168–169 | 490, 472 |
| 113. | Quinoxaline-2-carboxylic acid 1(S)-benzyl-4(R)-cyclobutylcarbamoyl-2(S)-hydroxy-7-methyl-octyl)-amide | 148–150 | 504, 486 |
| 114. | Quinoxaline-2-carboxylic acid [1(S)-(4-difluoromethoxy-benzyl)-2(S)-hydroxy-7-methyl-4(R)-methylcarbamoyl-octyl]-amide | 151–154 | 530 |
| 115. | 4-{3(S)-Hydroxy-7-methyl-5(R)-methylcarbamoyl-2(S)-[(quinoxaline-2-carbonyl)-amino]-octyl}-benzoic acid methyl ester | 87–95 | 508 |
| 116. | Quinoxaline-2-carboxylic acid 1(S)-benzyl-4-carbamoyl-2(S)-hydroxy-butyl)-amide | | 379 |
| 117. | 6,7,8-Trifluoro-quinoline-3-carboxylic acid 1(S)-benzyl-2(S)-hydroxy-7-methyl-4(R)-methylcarbamoyl-octyl)-amide | 206–207 | 516, 498 |
| 118. | 6,7,8-Trifluoro-quinoline-3-carboxylic acid 1(S)-benzyl-4(R)-carbamoyl-2(S)-hydroxy-7-methyl-octyl)-amide | 205–206 | 502, 485 |
| 119. | 6,8-Difluoro-quinoline-3-carboxylic acid 1(S)-benzyl-2(S)-hydroxy-7-methyl-4(R)-methylcarbamoyl-octyl)-amide | 198–200 | 498 |
| 120. | 6,8-Difluoro-quinoline-3-carboxylic acid 1(S)-benzyl-4(R)-carbamoyl-2(S)-hydroxy-7-methyl-octyl)-amide | 188–190 | 484, 467 |

TABLE 1-continued

| EXAMPLE | NAME | M.P. (° C.) | LRMS |
|---|---|---|---|
| 121. | Quinoxaline-2-carboxylic acid 1(S)-benzyl-4(R)-butylcarbamoyl-5-cyclopentyl-2(S)-hydroxy-pentyl)-amide | 102–104 | 517, 499 |
| 122. | 6-Methyl-pyridine-2-carboxylic acid 1(S)-benzyl-2(S)-hydroxy-6-methyl-4(R)-methylcarbamoyl-heptyl)-amide | 74–76 | |
| 123. | Quinoxaline-2-carboxylic acid 1(S)-benzyl-2(S)-hydroxy-8-methyl-4(R)-methylcarbamoyl-nonyl)-amide | 145.5–146.5 | 477 |
| 124. | Quinoxaline-2-carboxylic acid 1(S)-benzyl-4(R)-carbamoyl-2(S)-hydroxy-8-methyl-nonyl)-amide | 163–165 | 463 |
| 125 | Quinoxaline-2-carboxylic acid 1(S)-biphenyl-4-ylmethyl-2(S)-hydroxy-7-methyl-4(R)-methylcarbamoyl-octyl)-amide | 123–125 | 539, 521, 508 |
| 126. | Quinoxaline-2-carboxylic acid 1(S)-benzyl-4(R)-carbamoyl-2(S)-hydroxy-7-methyl-oct-6-enyl)-amide | 168–170 | 447, 430 |
| 127. | Quinoxaline-2-carboxylic acid (2(S)-hydroxy-6-methyl-4(R)-methylcarbamoyl-1(S)-naphthalen-2-ylmethyl-heptyl)-amide | 121–123 | |
| 128. | Quinoxaline-2-carboxylic acid 1(S)-benzyl-4(R)-carbamoyl-2(S)-hydroxy-7,7-dimethyl-octyl)-amide | 77–79 | 463, 446 |
| 129. | Quinoxaline-2-carboxylic acid 1(S)-benzyl-2(S)-hydroxy-7,7-dimethyl-4(R)-methylcarbamoyl-octyl)-amide | 195–199 | 477, 459 |
| 130. | Quinoxaline-2-carboxylic acid 1(S)-benzyl-4(R)-carbamoyl-2(S)-hydroxy-5-phenyl-pentyl)-amide | 168–172 | 469, 452 |
| 131. | Quinoxaline-2-carboxylic acid 1(S)-biphenyl-4-ylmethyl-4(R)-carbamoyl-2(S)-hydroxy-7-methyl-octyl)-amide | 205–206 | 508 |
| 132. | Quinoxaline-2-carboxylic acid [1(S)-benzyl-5-(4,4-difluoro-cyclohexyl)-2(S)-hydroxy-4(R)-methylcarbamoyl-pentyl]-amide | 170–172 | 525, 507 |
| 133. | Quinoxaline-2-carboxylic acid [1(S)-benzyl-4(R)-carbamoyl-5-(4,4-difluoro-cyclohexyl)-2(S)-hydroxy-pentyl]-amide | 174–176 | 511, 493 |
| 134. | Quinoxaline-2-carboxylic acid [1(S)-(3-fluoro-benzyl)-2(S)-hydroxy-7-methyl-4(R)-methylcarbamoyl-octyl]-amide | 158.5–159.5 | 481, 463 |
| 135. | Quinoxaline-2-carboxylic acid [4(R)-carbamoyl-1(S)-(3-fluoro-benzyl)-2(S)-hydroxy-7-methyl-octyl]-amide | 191–191.5 | 467, 449 |
| 136. | Quinoxaline-2-carboxylic acid 1(S)-benzyl-2(S)-hydroxy-7-methyl-4(R)-methylcarbamoyl-oct-6-enyl)-amide | 65–68 | 461, 443 |
| 137. | 6,7,8-Trifluoro-quinoline-3-carboxylic acid 1(S)-benzyl-2(S)-hydroxy-7(S)-methyl-4(R)-methylcarbamoyl-nonyl)-amide | 158–161 | 541, 523 |
| 138. | Quinoxaline-2-carboxylic acid 1(S)-benzyl-4(R)-carbamoyl-2(S)-hydroxy-7(S)-methyl-nonyl)-amide | 185–187 | 446 |
| 139. | Quinoxaline-2-carboxylic acid 1(S)-benzyl-7-fluoro-2(S)-hydroxy-7-methyl-4(R)-methylcarbamoyl-octyl)-amide | 148–150 | 482, 463 |
| 140. | Quinoxaline-2-carboxylic acid 1(S)-benzyl-4(R)-carbamoyl-7-fluoro-2(S)-hydroxy-7-methyl-octyl)-amide | 184–186 | 467, 449 |
| 141. | Quinoxaline-2-carboxylic acid 1(S)-benzyl-2(S)-hydroxy-7-methyl-4(R)-methylcarbamoyl-nonyl)-amide | 137–139.5 | 478 |
| 142. | Quinoxaline-2-carboxylic acid 1(S)-benzyl-4(R)-dimethylcarbamoyl-2(S)-hydroxy-7-methyl-octyl)-amide | 68–70 | |
| 143. | 78-Difluoro-quinoline-3-carboxylic acid 1(S)-benzyl-2(S)-hydroxy-4(R)-methylcarbamoyl-5-phenyl-pentyl)-amide | 175 (Dec.) | 518, 500 |
| 144. | 7,8-Difluoro-quinoline-3-carboxylic acid 1(S)-benzyl-2(S)-hydroxy-7-methyl-4(R)-methylcarbamoyl-octyl)-amide | 198–201 | 498, 480 |
| 145. | 8-Fluoro-quinoline-3-carboxylic acid 1(S)-benzyl-2(S)-hydroxy-7-methyl-4(R)-methylcarbamoyl-octyl)-amide | 179–183 | 480, 462 |
| 146. | Quinoxaline-2-carboxylic acid 1(S)-benzyl-2(S)-hydroxy-7(R)-methylcarbamoyl-non-6-enyl)-amide | 130–132 | 462, 448 |
| 147. | Quinoxaline-2-carboxylic acid 1(S)-benzyl-4(R)-carbamoyl-2(S)-hydroxy-non-6-enyl)-amide | 154–155 | 448, 430 |
| 148. | 7,8-Difluoro-quinoline-3-carboxylic acid 1(S)-benzyl-4(R)-carbamoyl-2(S)-hydroxy-7-methyl-octyl)-amide | 188–190 | 485, 467 |
| 149. | 8-Fluoro-quinoline-3-carboxylic acid 1(S)-benzyl-4(R)-carbamoyl-2(S)-hydroxy-7-methyl-octyl)-amide | 192–196 | 466, 449 |
| 150. | Quinoxaline-2-carboxylic acid 1(S)-benzyl-4(R)-carbamoyl-2(S)-hydroxy-nonyl)-amide | 188.5–189.5 | 450 |
| 151. | 2(S)-{2(S)-hydroxy-4-phenyl-3(S)-[(quinoxaline-2-carbonyl)-amino]-butyl}-N1,N4-dimethyl-succinamide | 178–180 | |
| 152. | Quinoxaline-2-carboxylic acid 1(S)-benzyl-4(R)-ethylcarbamoyl-7-fluoro-2(S)-hydroxy-7-methyl-octyl)-amide | 105–108 | 496 |
| 153. | Quinoxaline-2-carboxylic acid 1 (S)-benzyl-4(R)-butylcarbamoyl-7-fluoro-2(S)-hydroxy-7-methyl-octyl)-amide | 110–112 | 523, 505 |
| 154. | Quinoxaline-2-carboxylic acid [7-fluoro-1(S)-(4-fluoro-benzyl)-2(S)-hydroxy-7-methyl-4(R)-methylcarbamoyl-octyl]-amide | 145–147 | 499 |
| 155. | Quinoxaline-2-carboxylic acid [4(R)-carbamoyl-1(S)-(3,4-dichloro-benzyl)-7-fluoro-2(S)-hydroxy-7-methyl-octyl]-amide | 206–207 | 536, 518 |
| 156. | 7,8-Difluoro-quinoline-3-carboxylic acid [4(R)-carbamoyl-1(S)-(3,4-dichloro-benzyl)-7-fluoro-2(S)-hydroxy-7-methyl-octyl]-amide | 187–189 | 571 |
| 157. | Quinoxaline-2-carboxylic acid (4(R)-carbamoyl-2(S)-hydroxy-7-methyl-1 (S)-phenethyl-octyl)-amide, | 223–225 | 478 |
| 158. | 7,8-Difluoro-quinoline-3-carboxylic acid [4(R)-carbamoyl-7-fluoro-1 (S)-(4-fluoro-benzyl)-2(S)-hydroxy-7-methyl-octyl]-amide | 208–210 | 463, 445 |
| 159. | Quinoxaline-2-carboxylic acid [4(R)-carbamoyl-7-fluoro-1(S)-(4-fluoro-benzyl)-2(S)-hydroxy-7-methyl-octyl]-amide | | 520 |
| 160. | Quinoxaline-2-carboxylic acid [1(S)-benzyl-7-fluoro-2(S)-hydroxy-7-methyl-4(R)-(4-methyl-piperazine-1-carbonyl)-octyl]-amide, | | 551 |
| 161. | Quinoxaline-2-carboxylic acid [1(S)-benzyl-4(R)-carbamoyl-2(S)-hydroxy-5-(tetrahydro-pyran-4(R)-yl)-pentyl]-amide | 212–214 | 477, 459 |
| 162. | Quinoxaline-2-carboxylic acid [1(S)-benzyl-7-fluoro-2(S)-hydroxy-7-methyl-4(R)-(piperidine-1 -carbonyl)-octyl]-amide | | 536 |
| 163. | Quinoxaline-2-carboxylic acid [1(S)-benzyl-7-fluoro-2(S)-hydroxy-7-methyl-4(R)-(morpholine-4-carbonyl)-octyl]-amide, | | 537 |

TABLE 1-continued

| EXAMPLE | NAME | M.P. (° C.) | LRMS |
|---|---|---|---|
| 164. | Quinoxaline-2-carboxylic acid [1(S)-benzyl-3-(2-carbamoyl-indan-2-yl)-2(S)-hydroxy-propyl]-amide | 90–100 | 481, 464 |
| 165. | Quinoxaline-2-carboxylic acid 1(S)-benzyl-2(S)-hydroxy-4 (R)-methylcarbamoyl-7-phenyl-hept-6-enyl)-amide | 212–216 (Dec.) | |
| 166. | Quinoline-2-carboxylic acid 1(S)-benzyl-4(R)-carbamoyl-7-fluoro-2(S)-hydroxy-7-methyl-octyl)-amide | 163.5–165 | 466 449 |
| 167. | 6,7-Dihydro-5H-[1]pyrindine-3-carboxylic acid 1(S)-benzyl-4(R)-carbamoyl-7-fluoro-2(S)-hydroxy-7-methyl-octyl)-amide | 175–178 | 456 |
| 168. | Quinoxaline-2-carboxylic acid (1(S)-benzyl-4-carbamoyl-4(S)-cyclohexyl-2(S)-hydroxy-butyl)-amide; | 222–223 | 461 444 |
| 169. | Quinoxaline-2-carboxylic acid (1(S)-benzyl-4-carbamoyl-4(S)-cyclohexyl-2(S)-hydroxy-butyl)-amide | 178–180 | 461 444 |
| 170. | Quinoxaline-2-carboxylic acid (1(S)-benzyl-4-carbamoyl-4(S)-cyclohexyl-2(S)-hydroxy-butyl)-amide | 229–232 | 447 |
| 171. | Quinoxaline-2-carboxylic acid (1(S)-benzyl-4-carbamoyl-4(S)-cyclopentyl-2(S)-hydroxy-butyl)-amide; | 126–128 | 447 |
| 172. | Quinoline-3-carboxylic acid 1(S)-benzyl-4(R)-carbamoyl-7-fluoro-2(S)-hydroxy-7-methyl-octyl)-amide | 200–202 | 466, 449 |
| 173. | N-1(S)-Benzyl-4(R)-carbamoyl-7-fluoro-2(S)-hydroxy-7-methyl-octyl)-5-bromo-nicotinamide | 181–183 | 476 |
| 174. | Quinoxaline-2-carboxylic acid [4(R)-carbamoyl-1-(2(S)-fluoro-benzyl)-2(S)-hydroxy-7-methyl-octyl]-amide | 184–187 | 466, 448 |
| 175. | Quinoxaline-2-carboxylic acid [4(R)-carbamoyl-1 (S)-(2-fluoro-benzyl)-2(S)-hydroxy-7-methyl-octyl]-amide | 213–215 | 466 |
| 176. | Quinoxaline-2-carboxylic acid [1(S)-benzyl-4(S)-carbamoyl-2(S)-hydroxy-4-(4-isopropyl-cyclohexyl)-butyl]-amide; | | 502 |
| 177. | Quinoxaline-2-carboxylic acid (4(R)-carbamoyl-2(S)-hydroxy-7-methyl-1(S)-thiophen-2-ylmethyl-octyl)-amide | | 454, 436 |
| 178. | Quinoxaline-2-carboxylic acid (4(R)-carbamoyl-2(S)-hydroxy-7-methyl-1(S)-thiazol-4-ylmethyl-octyl)-amide | 195–196 | 456 |
| 179. | Quinoxaline-2-carboxylic acid [1(S)-benzyl-4(S)-carbamoyl-2(S)-hydroxy-4-(3,3,5,5-tetramethyl-cyclohexyl)-butyl]-amide | 188–190 | 516 |
| 180. | Quinoxaline-2-carboxylic acid (1(S)-benzyl-4(S)-carbamoyl-2(S)-hydroxy-4-indan-2-yl-butyl)-amide; | | 495 |
| 181. | Quinoxaline-2-carboxylic acid (1(S)-benzyl-4(S)-carbamoyl-4-cycloheptyl-2(S)-hydroxy-butyl)-amide; | 216–217 | 474, 457 |
| 182. | Quinoxaline-2-carboxylic acid (1(S)-benzyl-4(S)-carbamoyl-2(S)-hydroxy-5-propyl-octyl)-amide; | | 477 |
| 183. | Quinoxaline-2-carboxylic acid (1(S)-benzyl-4(S)-carbamoyl-2(S)-hydroxy-5-propyl-oct-5-enyl)-amide; | | |
| 184. | Quinoxaline-2-carboxylic acid 1(S)-benzyl-4(R)-carbamoyl-2(S),7-dihydroxy-7-methyl-octyl)-amide | | |
| 185. | Quinoxaline-2-carboxylic acid 1(S)-benzyl-7-chloro-2(S)-hydroxy-4(R)-methylcarbamoyl-hept-6-enyl)-amide | | 467, 449 |
| 186. | Quinoxaline-2-carboxylic acid 1(S)-benzyl-7-chloro-2(S)-hydroxy-4(R)-methylcarbamoyl-hept-6-enyl) amide | | 467, 449 |
| 187. | Quinoxaline-2-carboxylic acid 1(S)-benzyl-6-chloro-2(S)-hydroxy-4(R)-methylcarbamoyl-hept-6-enyl)-amide | 160–162 | 467, 449 |
| 188. | Quinoxaline-2-carboxylic acid 1(S)-benzyl-4(R)-carbamoyl-chloro-2(S)-hydroxy-hept-6-enyl)-amide | 203–204.5 | |
| 189. | Quinoxaline-2-carboxylic acid 1(S)-benzyl-4(S)-carbamoyl-6-cyclopropyl-2(S)-hydroxy-hexyl)-amide | 171–174 | 447, 429 |
| 190. | Quinoxaline-2-carboxylic acid 4(S)-benzyl-6-cyclopropyl-2(S)-hydroxy-4(R)-methylcarbamoyl-hexyl)-amide | 146–148 | 461, 443 |
| 191. | Quinoxaline-2-carboxylic acid [1(S)-benzyl-4(R)-carbamoyl-2(S)-hydroxy-4(S)-(4-methyl-cyclohexyl)-butyl]-amide; | 218–220 | 475, 457 |
| 192. | Quinoxaline-2-carboxylic acid (1(S)-benzyl-4(R)-carbamoyl-2(S)-hydroxy-4-indan-2-yl-butyl)-amide; | 190–191 | 495, 477 |
| 193. | Quinoxaline-2-carboxylic acid [1(S)-benzyl-4(R)-carbamoyl-2(S)-hydroxy-5-(4-trifluoromethoxy-phenyl)-pentyl]-amide | 184–187 | 553, 536 |
| 194. | Quinoxaline-2-carboxylic acid [1(S)-benzyl-4(R)-carbamoyl-5-(4-fluoro-phenyl)-2(S)-hydroxy-phenyl-amide | 164–166 | 487, 470 |
| 195. | Quinoxaline-2-carboxylic acid 1(S)-benzyl-4(R)-carbamoyl-7-chloro-2(S)-hydroxy-hept-6-enyl)-amide | 165–166 | 436 |
| 196. | Quinoxaline-2-carboxylic acid 1(S)-benzyl-4(R)-carbamoyl-7-chloro-2(S)-hydroxy-hept-6-enyl)-amide | 158–160 | 436 |
| 197. | 3-Hydroxy-quinoxaline-2-carboxylic acid 1(S)-benzyl-4(R)-carbamoyl-7-fluoro-2(S)-hydroxy-7-methyl-octyl)-amide | 185–189 | 483, 465 |
| 198. | Quinoxaline-2-carboxylic acid 1(S)-benzyl-4(R)-benzylcarbamoyl-7-fluoro-2(S)-hydroxy-7-methyl-octyl)-amide | 183–184 | |
| 199. | Quinoxaline-2-carboxylic acid {1(S)-benzyl-7-fluoro-2(S)-hydroxy-7-methyl-4(R)-[(pyridin-3-ylmethyl)-carbamoyl]-octyl}-amide | 188–191 | |
| 200. | Quinoxaline-2-carboxylic acid 1(S)-benzyl-8, 8-trifluoro-2(S)-hydroxy-4(R)-methylcarbamoyl-7-trifluoromethyl-octyl)-amide | | 571, 553 |
| 201. | Quinoxaline-2-carboxylic acid 1(S)-benzyl4(R)-carbamoyl-8,8-trifluoro-2(S)-hydroxy-7-trifluoromethyl-octyl)-amide | 187–193 | 553 |
| 202. | Quinoxaline-2-carboxylic acid [2(S)-hydroxy-7-methyl-4(R)-methylcarbamoyl-1(S)-(4-methylcarbamoyl-benzyl)-octyl]-amide | 170–173 | 502 |
| 203. | Quinoxaline-2-carboxylic acid (1(S)-benzyl-4(S)-carbamoyl-5-ethyl-2(S)-hydroxy-heptyl)-amide; | 215–218 | 448 431 |
| 204. | Quinoxaline-2-carboxylic acid [1(S)-benzyl-4(S)-carbamoyl-2(S)-hydroxy-4-(tetrahydro-pyran-4-yl)-butyl]-amide; | 151–154 | |
| 205. | Quinoxaline-2-carboxylic acid [1(S)-benzyl-7-fluoro-2(S)-hydroxy-7-methyl-4(R)-(2-pyridin-2-yl-ethylcarbamoyl)-octyl]-amide | 155–156 | 572 |

TABLE 1-continued

| EXAMPLE | NAME | M.P. (° C.) | LRMS |
|---|---|---|---|
| 206. | Quinoxaline-2-carboxylic acid [1(S)-benzyl-4(R)-(3,4-dimethoxy-benzylcarbamoyl)-7-fluoro-2(S)-hydroxy-7-methyl-octyl]-amide | 162–164 | 617 |
| 207. | Quinoxaline-2-carboxylic acid 1(S)-benzyl-4(R)-carbamoyl-2(S)-hydroxy-6-methoxy-hexyl)-amide | | 420 |
| 208. | Quinoxaline-2-carboxylic acid 1(S)-benzyl-4(R)-carbamoyl-7-chloro-2(S)-hydroxy-oct-6-enyl)-amide | 172–175 | 450 |
| 209. | Quinoxaline-2-carboxylic acid 1(S)-benzyl-7-chloro-2(S)-hydroxy-4(R)-methylcarbamoyl-oct-6-enyl)-amide | 108–111 | 463 |
| 210. | Quinoxaline-2-carboxylic acid [1(S)-benzyl-4(R)-carbamoyl-4-(3,5-dimethyl-cyclohexyl)-2(S)-hydroxy-butyl]-amide; | 221–222 | 489, 471 |
| 211 | Quinoxaline-2-carboxylic acid {1(S)-benzyl-7-fluoro-2(S)-hydroxy-7-methyl-4(R)-[(pyridin-2-ylmethyl)-carbamoyl]-octyl}-amide | 138–140 | 557, 540 |
| 212 | Quinoxaline-2-carboxylic acid {1(S)-benzyl-7-fluoro-2(S)-hydroxy-4(R)-[2-(4-hydroxy-phenyl)-ethylcarbamoyl]-7-methyl-octyl}-amide | 138–140 | 587, 569 |
| 213. | Quinoxaline-2-carboxylic acid {1(S)-benzyl-7-fluoro-2(S)-hydroxy-7-methyl-4(R)-[(thiophen-2-ylmethyl)-carbamoyl]-octyl}-amide | 174–175 | 563, 545 |
| 214. | Quinoxaline-2-carboxylic acid 1 (S)-benzyl-4(R)-carbamoyl-2(S)-hydroxy-6-phenoxy-hexyl)-amide | 194.5–196.5 | 482 |
| 215. | Quinoxaline-2-carboxylic acid 1(S)-benzyl-4(R)-carbamoyl-2(S)-hydroxy-6-isopropoxy-hexyl)-amide | 113–118 (Mix) | 448 |
| 216. | Quinoxaline-2-carboxylic acid {1(S)-benzyl-7-fluoro-2(S)-hydroxy-7-methyl-4(R)-[2-(4-sulfamoyl-phenyl)-ethylcarbamoyl]-octyl}-amide | 207–210 | 650 |
| 217. | Quinoxaline-2-carboxylic acid {1(S)-benzyl-7-fluoro-2(S)-hydroxy-7-methyl-4(R)-[(pyridin-4-ylmethyl)-carbamoyl]-octyl}-amide | 100–104 | 558 |
| 218. | Quinoxaline-2-carboxylic acid [1(S)-benzyl-4(R)-(2-ethylsulfanyl-ethytcarbamoyl)-7-fluoro-2(S)-hydroxy-7-methyl-octyl]-amide | 78–79 | 555, 537 |
| 219. | Quinoxaline-2-carboxylic acid [1(S)-benzyl-7-fluoro-2(S)-hydroxy-4(R)-(2-methoxy-ethytcarbamoyl)-7-methyl-octyl]-amide | 48–50 | 507 |
| 220. | Quinoxaline-2carboxylic acid [1(S)-benzyl-7-fluoro-2(S)-hydroxy-7-methyl-4(R)-(2-pyridin-3-yl-ethylcarbamoyl)-octyl)-amide | 154–155 | 572 |
| 221. | Quinoxaline-2-carboxylic acid [1(S)-benzyl-7-fluoro-2(S)-hydroxy-7-methyl-4(R)-(2-pyridin-4-yl-ethylcarbamoyl)-octyl]-amide | 78–80 | 572 |
| 222. | Quinoxaline-6-carboxylic acid 1(S)-benzyl-4(R)-carbamoyl-7-fluoro-2(S)-hydroxy-7-methyl-octyl)-amide | 190–192 | 467 |
| 223. | Quinoxaline-2-carboxylic acid 1(S)-benzyl-6-tert-butoxy-4(R)-carbamoyl-2(S)-hydroxy-hexyl)-amide | 184–189 | 479, 461 |
| 224. | Quinoxaline-2-carboxylic acid {1(S)-benzyl-7-fluoro-2(S)-hydroxy-7-methyl 4(R)-[2-1 -methyl-1 H-pyrrol-2-yl)-ethylcarbamoyl]-octyl}-amide | 100–105 | 574 |
| 225. | Quinoxaline-2-carboxylic acid [1(S)-benzyl-4(S)-carbamoyl-4-(1,1-dioxo-thiopyran-4-yl)-2(S)-hydroxy-butyl]-amide; | 140–150 | 511, 494 |
| 226. | Quinoxaline-2-carboxylic acid {1(S)-benzyl-7-fluoro-2(S)-hydroxy-4(R)-[2-(6-methoxy-1H-indol-3-yl)-ethylcarbamoyl]-7-methyl-octyl-amide, | | 640, 622 |
| 227. | Quinoxaline-2-carboxylic acid [1(S)-benzyl-7-fluoro-2(S)-hydroxy-4(R)-(2-methoxy-benzylcarbamoyl)-7-methyl-octyl]-amide | 135 | 587, 569 |
| 228. | Quinoxaline-2-carboxylic acid [1(S)-benzyl-7-fluoro-2(S)-hydroxy-4(R)-(3-methoxy-benzylcarbamoyl)-7-methyl-octyl]-amide | | 587, 569 |
| 229. | Quinoxaline-2-carboxylic acid [1(S)-benzyl-7-fluoro-2(S)-hydroxy-7-methyl-4(R)-(2-thiophen-2-yl-ethylcarbamoyl)-octyl]-amide | 152–154 | 577 |
| 230. | Quinoxaline-2-carboxylic acid {1(S)-benzyl-7-fluoro-2(S)-hydroxy-4(R)-[-(1H-indol-3-yl)-ethylcarbamoyl]-7-methyl-octyl}-amide | 107–108 | 610 |
| 231. | Quinoxaline-2-carboxylic acid {4(R)-[2-(4-amino-phenyl)-ethylcarbamoyl]-1(S)-benzyl-7-fluoro-2(S)-hydroxy-7-methyl-octyl}-amide | | 586 |
| 232. | Quinoxaline-2-carboxylic acid {1(S)-benzyl-4(R)-[2-(3,5-dimethoxy-phenyl)-ethylcarbamoyl]-7-fluoro-2(S)-hydroxy-7-methyl-octy}-amide | 109–112 | 631, 61 3 |
| 233. | Quinoxaline-2-carboxylic acid {1(S)-benzyl-4(R)-[2-(3,4-dimethoxy-phenyl)-ethylcarbamoyl]-7-fluoro-2(S)-hydroxy-7-methyl-octyl}-amide | | 631, 61 3 |
| 234. | Quinoxaline-2-carboxylic acid {1(S)-benzyl-7-fluoro-4(R)-[(furan-2-ylmethyl)-carbamoyl]-2(S)-hydroxy-7-methyl-octyl}-amide | 155.5–156.5 | 547 |
| 235. | Quinoxaline-2-carboxylic acid {1(S)-benzyl-4(R)-[2-(2,5-dimethoxy-phenyl)-ethylcarbamoyl]-7-fluoro-2(S)-hydroxy-7-methyl-octyl}-amide | | 631, 61 3 |
| 236. | Quinoxaline-2-carboxylic acid [1(S)-benzyl-7-fluoro-2(S)-hydroxy-4(R)-(4-methoxy-benzylcarbamoyl)-7-methyl-octyl]-amide | 114–115 | 587, 569 |
| 237. | Quinoxaline-2-carboxylic acid 1(S)-benzyl-4(R)-carbamoyl-6-cyclohexyloxy-2(S)-hydroxy-hexyl)-amide | 150–152 | 505, 487 |
| 238. | Quinoxaline-2-carboxylic acid {4(R)-[(1 H-benzoimidazol-2-ylmethyl)-carbamoyl]-1 (S)-benzyl-7-fluoro-2(S)-hydroxy-7-methyl-octyl}-amide | | 596 |
| 239. | Quinoxaline-2-carboxylic acid [1(S)-benzyl-7-fluoro-2(S)-hydroxy-4(R)-(2(S)-hydroxymethyl-pyrrolidine-1-carbonyl)-7-methyl-octyl]-amide | 217–219 | 551, 533 |
| 240. | Quinoxaline-2-carboxylic acid {1(S)-benzyl-7-fluoro-2(S)-hydroxy-7-methyl-4(R)-[(tetrahydrofuran-2-ylmethyl)-carbamoyl]-octyl}-amide | 111–115 | 551, 533 |
| 241. | Quinoxaline-2-carboxylic acid [1(S)-benzyl-4(R)-carbamoyl-4-(4,4-difluoro-cyclohexyl)-2(S)-hydroxy-butyl]-amide | 176–179 | 497, 478 |
| 242. | Quinoxaline-2-carboxylic acid [1(S)-benzyl-4(R)-(2,3-dimethoxy-benzylcarbamoyl)-7-fluoro-2(S)-hydroxy-7-methyl-octyl]-amide | 99–101 | |
| 243. | Quinoxaline-2-carboxylic acid [1(S)-benzyl-4(S)-carbamoyl-2(S)-hydroxy-4-(1-hydroxy-cyclohexyl)-butyl]-amide; | 187–189 | 477 379 |
| 244. | Quinoxaline-2-carboxylic acid [1(S)-benzyl-4(R)-carbamoyl-4-(2,6-dimethyl-tetrahydro-pyran-4-yl)-2(S)-hydroxy-butyl]-amide; | 195–198 | 491 |

TABLE 1-continued

| EXAMPLE | NAME | M.P. (° C.) | LRMS |
|---|---|---|---|
| 245. | Quinoxaline-2-carboxylic acid [4(R)-carbamoyl-7-fluoro-1(S)-(3-fluoro-benzyl)-2(S)-hydroxy-7-methyl-octyl]-amide | 225–227 | 485 467 |
| 246. | 7,8-Difluoro-quinoline-3-carboxylic acid 1(S)-benzyl-4(R)-carbamoyl-7-fluoro-2(S)-hydroxy-7-methyl-octyl)-amide | >220 | 502 485 |
| 247. | N-1(S)-Benzyl-4(R)-carbamoyl-7-fluoro-2(S)-hydroxy-7-methyl-octyl)-5,6-dichloro-nicotinamide | >220 | 484 466 |
| 248. | Benzofuran-2-carboxylic acid 1(S)-benzyl-4(R)-carbamoyl-7-fluoro-2(S)-hydroxy-7-methyl-octyl)-amide | 190–192 | 455, 438 |
| 249. | Cinnoline-4-carboxylic acid 1(S)-benzyl-4(R)-carbamoyl-7-fluoro-2(S)-hydroxy-7-methyl-octyl)-amide | 198–199.5 | 469 451 |
| 250. | Quinoxaline-2-carboxylic acid [4(R)-carbamoyl-7-fluoro-2(S)-hydroxy-1(S)-(4-iodo-benzyl)-7-methyl-octyl]-amide, | 185.5–187.5 | 593, 576 |
| 251. | Pyrazine-2-carboxylic acid 1(S)-benzyl-4(R)-carbamoyl -fluoro 2(S)-hydroxy-7-methyl-octyl)-amide, | 211–212 | 417, 319 |
| 252. | 6,7,8-Trifluoro-quinoline-3-carboxylic acid 1(S)-benzyl-4(R)-carbamoyl-7-fluoro-2(S)-hydroxy-7-methyl-octyl)-amide, | 195–197 | 520, 503 |
| 253. | Quinoline-6-carboxylic acid 1(S)-benzyl-4(R)-carbamoyl-7-fluoro-2(S)-hydroxy-7-methyl-octyl)-amide, | 170–173 | 466, 449 |
| 254. | Isoquinoline-3-carboxylic acid 1(S)-benzyl-4(R)-carbamoyl-7-fluoro-2(S)-hydroxy-7-methyl-octyl)-amide, | 194–197 | 466, 448 |
| 255. | 2-Methoxy-quinoline-3-carboxylic acid 1(S)-benzyl-4(R)-carbamoyl-7-fluoro-2(S)-hydroxy-7-methyl-octyl)-amide, | 213–216 | 496, 479 |
| 256. | 1H-Benzoimidazole-2-carboxylic acid 1(S)-benzyl-4(R)-carbamoyl-7-fluoro-2(S)-hydroxy-7-methyl-octyl)-amide, | 168–169 | 456, 438 |
| 257. | Benzothiazole-2-carboxylic acid 1(S)-benzyl-4(R)-carbamoyl-7-fluoro-2(S)-hydroxy-7-methyl-octyl)-amide | 152.5–155 | 472, 455 |
| 258. | 5-Methyl-pyrazine-2-carboxylic acid 1(S)-benzyl-4(R)-carbamoyl-7-fluoro 2(S)-hydroxy-7-methyl-octyl)-amide | 194–197 | 431 |
| 259. | Quinoxaline-2-carboxylic acid 1(S)-benzyl-4(R)-carbamoyl-2(S)-hydroxy-5-pyndin-3-yl-pentyl)-amide | | 470, 453 |
| 260. | Quinoxaline-2-carboxylic acid [1(S)-benzyl-4(S)-carbamoyl-2(S)-hydroxy-4-(1-hydroxy-cyclohexyl)-butyl]-amide; | 210–211 | 477, 459 |
| 261. | Quinoline-3-carboxylic acid (1(S)-benzyl-4(S)-carbamoyl-4-cyclohexyl-2(S)-hydroxy-butyl)-amide | 231 | 460 443 |
| 262. | Quinoline-2-carboxylic acid (1(S)-benzyl-4(S)-carbamoyl-4-cyclohexyl-2(S)-hydroxy-butyl)-amide | 208–210 | 460 443 |
| 263. | Fluoro-quinoline-3-carboxylic acid (1(S)-benzyl-4(S)-carbamoyl-4-cyclohexyl-2(S)-hydroxy-butyl)-amide | 238–240 | 478, 461 |
| 264. | N-(1(S)-Benzyl-4(S)-carbamoyl-4-cyclohexyl-2(S)-hydroxy-butyl)-5,6-dichloro-nicotinamide; | 174–177 | 461 |
| 265. | N-(1(S)-Benzyl-4(S)-carbamoyl-4-cyclohexyl-2(S)-hydroxy-butyl)-5-bromo-nicotinamide; | 255–256 | 475, 458 |
| 266. | Quinoxaline-2-carboxylic acid (4(R)-carbamoyl-7-fluoro-2(S)-hydroxy-7-methyl-1(S)-phenyl-octyl)-amide, | 159–160.5 | 453 |
| 267. | Quinoxaline-2-carboxylic acid 1(S)-benzyl-4(R)-carbamoyl-2(S)-hydroxy-5-pyridin-2-yl-pentyl)-amide, | | 470, 453 |
| 268. | Quinoxaline-2-carboxylic acid [4(R)-carbamoyl-2(S)-hydroxy-4-(1-hydroxy-cyclohexyl)-1(S)-thiophen-2-ylmethyl-butyl]-amide; | 206–207 | 482 |
| 269. | Quinoxaline-2-carboxylic acid [1(S)-benzyl-4(S)-carbamoyl-2(S)-hydroxy-4-(4-hydroxy-tetrahydro-thiopyran-4-yl)-butyl]-amide; | 123–125 | 495, 379 |
| 270. | 1,3-Dimethyl-1H-pyrazolo[3,4-b]pyridine-5-carboxylic acid 1(S)-benzyl-4(R)-carbamoyl-7-fluoro-2(S)-hydroxy-7-methyl-octyl)-amide, | 189.5–191 | 484 467 |
| 271. | Quinoxaline-2-carboxylic acid (1(S)-benzyl-7-fluoro-2(S)-hydroxy-4(R)-hydroxycarbamoyl-7-methyl-octyl)-amide | 165–166 | |
| 272. | Quinoxaline-2-carboxylic acid (1(S)-benzyl-7-fluoro-2(S)-hydroxy-4(R)-methoxycarbamoyl-7-methyl-octyl)-amide | | |
| 273. | 7,8-Difluoro-quinoline-3-carboxylic acid (1(S)-benzyl-4(R)-carbamoyl-2(S)-hydroxy-5-phenyl-pentyl)-amide | 233–235 | |
| 274. | Quinoxaline-2-carboxylic acid [1(S)-benzyl-4(R)-carbamoyl-5-(2-chloro-phenyl)-2(S)-hydroxy-pentyl]-amide | 182–185 | |
| 275. | Quinoxaline-2-carboxylic acid (1(S)-benzyl-4(R)-carbamoyl-2(S)-hydroxy-5-o-tolyl-pentyl)-amide | 168–171 | |
| 276. | Quinoxaline-2-carboxylic acid (1(S)-benzyl-2(S)-hydroxy-4(R)-hydroxycarbamoyl-5-phenyl-pentyl)-amide | 190–192 | |
| 277. | Quinoxaline-2-carboxylic acid [1(S)-benzyl-4(S)-carbamoyl-2(S)-hydroxy-4-(1-hydroxy-cyclopentyl)-butyl]-amide | 192–195 | 463, 446 |
| 278. | Quinoxaline-2-carboxylic acid [1(S)-benzyl-4(S)-carbamoyl-2(S)-hydroxy-4-(1-hydroxy-4-methyl-cyclohexyl)-butyl]-amide | 230–233 | 490 |
| 279. | Quinoxaline-2-carboxylic acid [1(S)-benzyl-4(S)-carbamoyl-5-(3,4-dichloro-phenyl)-2(S)-hydroxy-pentyl]-amide | 199–201 | |
| 280. | Quinoxaline-2-carboxylic acid [1(S)-benzyl-4(R)-carbamoyl-5-(2-fluoro-phenyl)-2(S)-hydroxy-pentyl]-amide | 171–173 | |
| 281. | Quinoxaline-2-carboxylic acid [1(S)-benzyl-2(S)-hydroxy-4(S)-hydroxycarbamoyl-4-(1-hydroxy-cyclopentyl)-butyl]-amide | 110–112 | 477 |
| 282. | Quinoxaline-2-carboxylic acid [1(S)-benzyl-4(S)-carbamoyl-2(S)-hydroxy-4-(1-hydroxy-3-methyl-cyclopentyl)-butyl]-amide | 187–188 | 476 |
| 283. | Quinoxaline-2-carboxylic acid [1(S)-benzyl-2(S)-hydroxy-4(S)-hydroxycarbamoyl-4-(1-hydroxy-4-methyl-cyclohexyl)-butyl]-amide | 114–116 | 506 |
| 284. | N-(1(S)-Benzyl-4(R)-carbamoyl-2(S)-hydroxy-5-phenyl-pentyl)-5-bromo-nicotinamide | | 494, 496 |
| 285. | 8-Fluoro-quinoline-carboxylic acid (1(S)-benzyl-4(R)-carbamoyl-2(S)-hydroxy-5-phenyl-pentyl)-amide | 206–209 | |
| 286. | 6,7-Dihydro-5H-[1]pyridine-3-carboxylic acid (1(S)-benzyl-4(R)-carbamoyl-2(S)-hydroxy-5-phenyl-pentyl)-amide | 182–186 | |
| 287. | Quinoline-3-carboxylic acid (1(S)-benzyl-4(R)carbamoyl-2(S)-hydroxy-5-phenyl-pentyl)-amide | 203–206 | |
| 288. | Quinoxaline-2-carboxylic acid [1(S)-benzyl-4(S)-carbamoyl-2(S)-hydroxy-4-(1-hydroxy-3,5-dimethyl-cyclohexyl)-butyl]-amide | 234–236 | 504 |
| 289. | Quinoxaline-2-carboxylic acid [1(S)-benzyl-2(S)-hydroxy-4(S)-hydroxycarbamoyl-4-(1-hydroxy-3,5-dimethyl-cyclohexyl)-butyl]-amide | | 520 |

TABLE 1-continued

| EXAMPLE | NAME | M.P. (° C.) | LRMS |
|---|---|---|---|
| 290. | Quinoxaline-2-carboxylic acid [1(S)-benzyl-4(S)-carbamoyl-2(S)-hydroxy-4-(1-hydroxy-cycloheptyl)-butyl]-amide | 189–191 | 491 |
| 291. | Quinoxaline-2-carboxylic acid [1(S)-benzyl-2(S)-hydroxy-4(S)-hydroxycarbamoyl-4-(1-hydroxy-cycloheptyl)-butyl]-amide | 118–119 | 506 |
| 292. | Quinoxaline-2-carboxylic acid [1(S)-benzyl-4(R)-carbamoyl-5-(3-fluoro-phenyl)-2(S)-hydroxy-pentyl]-amide | 176–179 | |
| 293. | Quinoxaline-2-carboxylic acid (1(S)-benzyl-4(R)-carbamoyl-2(S)-hydroxy-5-m-tolyl-pentyl)-amide | 178–179 | |
| 294. | Quinoxaline-2-carboxylic acid (1(S)-benzyl-2(S)-hydroxy-4-isobutylcarbamoyl-butyl)-amide | 146–148 | |
| 295. | Quinoxaline-2-carboxylic acid [1(S)-benzyl-4(S)-carbamoyl-2(S)-hydroxy-4-(2-hydroxy-adamantan-2-yl)-butyl]-amide | 206–207 | 528 |
| 296. | Quinoxaline-2-carboxylic acid [1(S)-benzyl-4(S)-carbamoyl-2(S)-hydroxy-4-(9-hydroxy-bicyclo[3.3.1]non-9-yl)-butyl)-amide | 268–269 | 516 |
| 297. | Quinoxaline-2-carboxylic acid [1(S)-benzyl-2(S)-hydroxy-4(S)-(2-hydroxy-adamantan-2-yl)-4-hydroxycarbamoyl-butyl]-amide | 133–134 | 544 |
| 298. | Quinoxaline-2-carboxylic acid [1(S)-benzyl-2(S)-hydroxy-4(S)-(9-hydroxy-bicyclo[3.3 1]non-9-yl)-4-hydroxycarbamoyl-butyl]-amide | 130–132 | 532 |
| 299. | Quinoxaline-2-carboxylic acid [1(S)-benzyl-4(R)carbamoyl-2(S)-hydroxy-5-(3-methoxy-phenyl)-pentyl]-amide | 147–148 | |
| 300. | Quinoxaline-2-carboxylic acid [1(S)-benzyl-4(S)-carbamoyl-2(S)-hydroxy-4-(1-hydroxy-4-propyl-cyclohexyl)-butyl]-amide | 227–228 | 519 |
| 301. | Quinoxaline-2-carboxylic acid [1(S)-benzyl-2(S)-hydroxy-4(S)-hydroxycarbamoyl-4-(1-hydroxy-4-propyl-cyclohexyl)-butyl]-amide | 115–117 | 533 |
| 302. | Quinoxaline-2-carboxylic acid [1(S)-benzyl-4(R)-carbamoyl-2(S)-hydroxy-5-(4-methoxy-phenyl)-pentyl]-amide | | 500, 483 |
| 303. | Quinoxaline-2-carboxylic acid [1(S)-benzyl-4(S)-carbamoyl-4(S)-(4-ethyl-1-hydroxy-cyclohexyl)-2-hydroxy-butyl]-amide | 246–248 | 504 |
| 304. | Quinoxaline-2-carboxylic acid [1(S)-benzyl-4(S)-carbamoyl-2(S)-hydroxy-4-(1-hydroxy-4,4-dimethyl-cyclohexyl)-butyl]-amide | 210–211 | 505 |
| 305. | Quinoxaline-2-carboxylic acid [1(S)-benzyl-2(S)-hydroxy-4(S)-hydroxycarbamoyl-4-(1-hydroxy-4,4-dimethyl-cyclohexyl)-butyl]-amide | 118–123 | 520 |
| 306. | Quinoxaline-2-carboxylic acid [1(S)-benzyl-4(S)-carbamoyl-4-(4,4-difluoro-1-hydroxy-cyclohexyl)-2(S)-hydroxy-butyl]-amide | 207.5–208.5 | |
| 307. | Quinoxaline-2-carboxylic acid [1(S)-benzyl-4S)-(4,4-difluoro-1-hydroxy-cyclohexyl)-2(S)-hydroxy-4-hydroxycarbamoyl-but yl]-amide | 130–131 | 572 |
| 308. | Quinoxaline-2-carboxylic acid [1(S)-benzyl-4(S)-carbamoyl-2(S)-hydroxy-4-(1-hydroxy-4-trifluoromethyl-cyclohexyl)-butyl]-amide | 250–252 | 545 |
| 309. | Quinoxaline-3- carboxylic acid 1(S)-cyclohexylmethyl-2(S)-hydroxy-6-methyl-4(R)-methylcarbamoyl-heptyl)-amide | 94–98 | 454 |
| 310. | Quinoxaline-2-carboxylic acid [1(S)-benzyl-7-fluoro-2(S)-hydroxy-7-methyl-4(R)-(pyrrolidine-1-carbonyl)-octyl]-amide | 174–175.5 | 522 |
| 311. | N-(1(S)-Benzyl-4(S)-carbamoyl-4-cyclohexyl-2(S)-hydroxy-butyl)-5-bromo-nicotinamide | 218–220 | 470 |
| 312. | Quinoxaline-2-carboxylic acid (1(S)-benzyl-7-fluoro-4(R)-hydrazinocarbonyl-2(S)-hydroxyl-7-methyl-octyl)-amide | 147–149 | 482,467 |

EXAMPLE 313

QUINOXALINE-2-CARBOXYLIC ACID 1(S)-BENZYL-4(R)-CARBAMOYL-2(S), 7-DIHYDROXY-7-METHYLOCTYL)-AMIDE

To the lactone from Example 2, method C (100 mg, 0.27 mmol), was added neat trifluoroacetic acid (1 mL). The resulting solution was stirred for 1 hour and the trifluoroacetic acid removed in vacuo. The remaining residue was solvated in methylene chloride (10 mL) and triethylamine (0.15 mL, 1.07 mmol). Quinoxalyl chloride (58 mg, 0.3 mmol) was added as a solid and the mixture stirred for 18 hour. The mixture was transferred to a separatory funnel and washed with citric acid (2×10 mL), NaHCO$_3$ (10 mL) and brine (10 mL). The organic layer was dried (MgSO$_4$) and the solvents filtered. The filtrate was concentrated in vacuo and the resulting residue was chromatographed on silica gel (10 g) eluting with 2:1 hexanes:ethyl acetate to provide 99 mg of the quinoxaline amide. This material was solvated in methanol and ammonia gas was bubbled in for 5 minutes. The resulting solution was stirred for 16 hours and the solvent removed in vacuo. The remaining residue was recrystallized (methylene chloride/methanol/Hexanes) to provide the title compound (90 mg, 72%). 1H NMR (400 MHz, CD3OD): d 9.38 (1H, s), 8.21 (1H, dd, J=4.4, 2.5 Hz), 8.14 (1H, dd, J=4.4, 2.5 Hz), 7.93 (2H, m), 7.26 (2H, d, J=6.9 Hz), 7.17 (2H, t, J=7.1 Hz), 7.09 (1H, t, J=7.3 Hz), 4.30 (1H, m), 3.75 (1H, m), 3.03–2.98 (2H, m), 2.47 (1H, m), 1.77 (1 H, m), 1.56 (2H, m), 1.4 (2H, m), 1.07 (6H, s).

EXAMPLES 314–344

The compounds from Table 2 were prepared according to the methods described above, substituting where appropriate the correct $R^2$ aldehyde, $R^3$ group, $R^1$ carboxylic acid or $R^4$ and $R^5$ amine where appropriate.

TABLE 2

| EXAMPLE NUMBER | NAME | MP | LRMS |
|---|---|---|---|
| 314 | Quinoxaline-2-carboxylic acid [4(R)-carbamoyl-1(S)-(3-fluoro-benzyl)-2(S),7-dihydroxy-7-methyl-octyl]-amide | 153–155 | 483., 465., 448 |

TABLE 2-continued

| EXAMPLE NUMBER | NAME | MP | LRMS |
|---|---|---|---|
| 315 | Quinoxaline-2-carboxylic acid [4(R)-carbamoyl-1(S)-(3,5-difluoro-benzyl)-2(S),7-dihydroxy-7-methyl-octyl]-amide | 162–163 | 500, 483, 466 |
| 316 | Quinoxaline-2-carboxylic acid 4(R)-carbamoyl-1(S)-(3-chloro-benzyl)-2(S),7-dihydroxy-7-methyl-octyl]-amide | 161–163 | 499, 481, 464 |
| 317 | Quinoxaline-2-carboxylic acid [1(S)-(3-chloro-benzyl)-2(S),7-dihydroxy-4(R)-hydroxycarbamoyl-7-methyl-octyl]-amide | 108–111 | 497, 464 |
| 318 | 7,8-Difluoro-quinoline-3-carboxylic acid (1S)-benzyl-4(R)-carbamoyl-2(S),7-dihydroxy-7-methyl-octyl)-amide | 171–173 | 501, 484 |
| 319 | 6,7,8-Trifluoro-quinoline-3-carboxylic acid (1(S)-benzyl-4(R)-carbamoyl-2(S),7-dihydroxy-7-methyl-octyl)-amide | 185–188 | 519, 502 |
| 320 | Quinoxaline-2-carboxylic acid [1(S)-(3,5-difluoro-benzyl)-2(S),7-dihydroxy-4(R)-hydroxycarbamoyl-7-methyl-octyl]-amide | 98–100 | 517 |
| 321 | Quinoxaline-2-carboxylic acid (1(S)-benzyl-2(S),7-dihydroxy-4(R)-hydroxycarbamoyl-7-methyl-octyl)-amide | 108–110 | 482, 464, 447 |
| 322 | 7,8-Difluoro-quinoline-3-carboxylic acid (1(S)-benzyl-4(R)-ethylcarbamoyl-2(S),7-dihydroxy-7-methyl-octyl)-amide | | 507, 484, 447 |
| 323 | N-(1(S)-Benzyl-4(R)-carbamoyl-2(S),7-dihydroxy-7-methyl-octyl)-4-trifluoromethyl-nicotinamide | 131–135 | 482, 464, 447 |
| 324 | Quinoxaline-2-carboxylic acid [4(R)-carbamoyl-1(S)-(2-chloro-benzyl)-2(S),7-dihydroxy-7-methyl-octyl]-amide | | |
| 325 | 7,8-Difluoro-quinoline-3-carboxylic acid [(4R)-carbamoyl-1(S)-(3-fluoro-benzyl)-2(S),7-dihydroxy-7-methyl-octyl]-amide | 174–177 | 518 |
| 326 | Quinoxaline-2-carboxylic acid [1(S)-(2-fluoro-benzyl)-2(S),7-dihydroxy4(R)-hydroxycarbamoyl-7-methyl-octyl]-amide | 130–131 | 499 |
| 327 | Quinoxaline-2-carboxylic acid (4(R)-carbamoyl-2(S),7-dihydroxy-7-methyl-1(S)-thiophen-2-ylmethyl-octyl)-amide | 158–159 | 471, 453, 436 |
| 328 | Quinoxaline-2-carboxylic acid [4(R)-carbamoyl-1(S)-(2-fluoro-benzyl)-2(S),7-dihydroxy-7-methyl-octyl]-amide | 147–148 | 483 |
| 329 | Quinoxaline-2-carboxylic acid [1(S)-(3,4-difluoro-benzyl)-2(S),7-dihydroxy-4(R)-hydroxycarbamoyl-7-methyl-octyl]-amide | 150–153 | 517, 499, 466 |
| 330 | Quinoxaline-2-carboxylic acid [4(R)-carbamoyl-1(S)-(3,4-difluoro-benzyl)-2(S),7-dihydroxy-7-methyl-octyl]-amide | 110–120 | 501, 483, 466 |
| 331 | Quinoxaline-2-carboxylic acid (4(R)-carbamoyl-2(S),7-dihydroxy-7-methyl-1(S)-naphthalen-1-ylmethyl-octyl)-amide | 155–158 | 515, 497, 480 |
| 332 | 6,7,8-Trifluoro-quinoline-3-carboxylic acid [4(R)-carbamoyl-1(S)-(3-fluoro-benzyl)-2(S),7-dihydroxy-7-methyl-octyl]-amide | 183–185 | 536, 518 |
| 333 | Quinoxaline-2-carboxylic acid (4(R)-carbamoyl-2(S),7-dihydroxy-7-methyl-1(S)-naphthalen-2-ylmethyl-octyl)-amide | 104–106 | 515, 497 |
| 334 | Quinoxaline-2-carboxylic acid (2(S),7-dihydroxy-4(R)-hydroxycarbamoyl-7-methyl-1(S)-naphthalen-2-ylmethyl-octyl)-amide | 98–100 | 498, 480 |
| 335 | Quinoxaline-2-carboxylic acid (1(S)-benzo[b]thiophen-3-ylmethyl-4(R)-carbamoyl-2(S),7-dihydroxy-7-methyl-octyl)-amide | 163–164 | 521, 503, 486 |
| 336 | Quinoxaline-2-carboxylic acid [1-benzyl-4-carbamoyl-2-hydroxy-5-(4-hydroxy-phenyl)-pentyl]-amide | 190.5–191.5 | |
| 337 | Quinoxaline-2-carboxylic acid [1-benzyl-4-carbamoyl-2-hydroxy-5-(3-hydroxy-phenyl)-pentyl]-amide | | |
| 338 | Quinoxaline-2-carboxylic acid [1-benzyl-4-carbamoyl-2-hydroxy-5-(2-hydroxy-phenyl)-pentyl]-amide | | |
| 339 | Quinoxaline-2-carboxylic acid [1-benzyl-4-carbamoyl-2-hydroxy-5-(2-hydroxy-5-methyl-phenyl)-pentyl]-amide | | |
| 340 | Quinoxaline-2-carboxylic acid [1-benzyl-4-carbamoyl-2-hydroxy-5-(2-hydroxy-3-methyl-phenyl)-pentyl]-amide | | |
| 341 | Quinoxaline-2-carboxylic acid [1-benzyl-4-carbamoyl-5-(3-ethoxy-2-hydroxy-phenyl)-2-hydroxy-pentyl]-amide | | |
| 342 | Quinoxaline-2-carboxylic acid [1-benzyl-4-carbamoyl-2-hydroxy-5-(4-hydroxy-3,5-dimethyl-phenyl)-pentyl]-amide | | |
| 343 | Quinoxaline-2-carboxylic acid (1-benzyl-4-carbamoyl-2,6-dihydroxy-6-methyl-heptyl)-amide | | |
| 344 | Quinoxaline-2-carboxylic acid [1-benzyl-4-carbamoyl-2-hydroxy-5-(1-hydroxy-cyclohexyl)-pentyl]-amide | | |

What is claimed is:
1. A compound of the formula

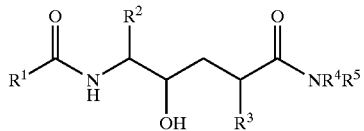

wherein
$R^1$ is quinoxalin-2-yl or quinoxalin-6-yl optionally substituted with one or more substituents independently selected from the group consisting of hydrogen, halo, CN, $(C_1-C_6)$alkyl optionally substituted with one or more fluorine atoms, hydroxy, hydroxy-$(C_1-C_6)$alkyl, $(C_1-C_6)$alkoxy optionally substituted with one or more fluorine atoms, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O— $(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N$(C=O)—$(C_1-C_6)$alkyl, $(C_1-C_6)$alkyl-HN(C=O)—$(C_1-C_6)$alkyl, $[(C_1-C_6)$alkyl$]_2N$—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkyl HN—$SO_2$—$(C_1-C_6)$alkyl, $[(C_1-C_6)$alkyl$]_2N$—$SO_2$—$(C_1-C_6)$alkyl, $CF_3SO_3$—, $(C_1-C_6)$alkyl-$SO_3$—, phenyl, $(C_3-C_{10})$cycloalkyl, $(C_2-C_9)$heterocycloalkyl, and $(C_2-C_9)$heteroaryl;

$R^2$ is phenyl-$(CH_2)_m$—, naphthyl-$(CH_2)_m$—, $(C_3-C_{10})$cycloalkyl-$(CH_2)_m$—, $(C_1-C_6)$alkyl or $(C_2-C_9)$heteroaryl-$(CH_2)_m$—, wherein m is an interger from zero to four; wherein each of said phenyl, naphthyl, $(C_3-C_{10})$cycloalkyl or $(C_2-C_9)$heteroaryl moieties of said phenyl-$(CH_2)_m$—, naphthyl-$(CH_2)_m$—, $(C_3-C_{10})$cycloalkyl-$(CH_2)_m$— or $(C_2-C_9)$heteroaryl-$(CH_2)_m$— groups may optionally be substituted with one or more substituents independently selected from hydrogen, halo, CN, $(C_1-C_6)$alkyl optionally substituted with one or more fluorine atoms, hydroxy, hydroxy-$(C_1-C_6)$alkyl, $(C_1-C_6)$alkoxy optionally substituted with one or more fluorine atoms, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N$(C=O)—$(C_1-C_6)$alkyl, $(C_1-C_6)$alkyl-HN(C=O)—$(C_1-C_6)$alkyl, $[(C_1-C_6)$alkyl$]_2N$—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkylHN—$SO_2$—$(C_1-C_6)$alkyl, $[(C_1-C_6)$alkyl$]_2N$—$SO_2$—$(C_1-C_6)$alkyl, $CF_3SO_3$—, $(C_1-C_6)$alkyl-$SO_3$—, phenyl, phenoxy, benzyloxy, $(C_3-C_{10})$cycloalkyl, $(C_2-C_9)$heterocycloalkyl, and $(C_2-C_9)$heteroaryl;

$R^3$ is hydrogen, $(C_1-C_{10})$alkyl, $(C_3-C_{10})$cycloalkyl-$(CH_2)_n$—, $(C_2-C_9)$heterocycloalkyl-$(CH_2)_n$—, $(C_2-C_9)$heteroaryl-$(CH_2)_n$— or aryl-$(CH_2)_n$—; wherein n is an interger from zero to six;

wherein said $R^3$ $(C_1-C_{10})$alkyl group may optionally be substituted with one or more substituents, independently selected from hydrogen, halo, CN, $(C_1-C_6)$alkyl optionally substituted with one or more fluorine atoms, hydroxy, hydroxy-$(C_1-C_6)$alkyl, $(C_1-C_6)$alkoxy, optionally substituted with one or more fluorine atoms, $(C_1-C_6)$alkoxy$(C_1-C_6)$alkyl, HO—(C=O)—$(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N$(C=O)—$(C_1-C_6)$alkyl, $(C_1-C_6)$alkyl-HN(C=O)—$(C_1-C_6)$alkyl, $[(C_1-C_6)$alkyl$]_2N$—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkylHN—$SO_2$—$(C_1-C_6)$alkyl, $[(C_1-C_6)$alkyl$]_2N$—$SO_2$—$(C_1-C_6)$alkyl, $CF_3SO_3$—, $(C_1-C_6)$alkyl-$SO_3$—, phenyl, $(C_3-C_{10})$cycloalkyl, $(C_2-C_9)$heterocycloalkyl, and $(C_2-C_9)$heteroaryl; and wherein any of the carbon-carbon single bonds of said $(C_1-C_{10})$alkyl may optionally be replaced by a carbon-carbon double bond;

wherein the $(C_3-C_{10})$cycloalkyl moiety of said $R^3$ $(C_3-C_{10})$cycloalkyl-$(CH_2)_n$— group may optionally be substituted by one to three substitutents independently selected from the group consisting of hydrogen, halo, CN, $(C_1-C_6)$alkyl optionally substituted with one or more fluorine atoms, hydroxy, hydroxy-$(C_1-C_6)$alkyl, $(C_1-C_6)$alkoxy optionally substituted with one or more fluorine atoms, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N$(C=O)—$(C_1-C_6)$alkyl, $(C_1-C_6)$alkyl-HN(C=O)—$(C_1-C_6)$alkyl, $[(C_1-C_6)$alkyl$]_2N$—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl- (S=O)—, ($C_1$–$C_6$)alkyl-$SO_2$—, ($C_1$–$C_6$)alkyl-$SO_2$—NH—, $H_2$N—$SO_2$—, $H_2$N—$SO_2$—($C_1$–$C_6$)alkyl, ($C_1$–$C_6$)alkylHN—$SO_2$—($C_1$–$C_6$)alkyl, [($C_1$–$C_6$)alkyl]$_2$N—$SO_2$—($C_1$–$C_6$)alkyl, $CF_3SO_3$—, ($C_1$–$C_6$)alkyl-$SO_3$—, phenyl, ($C_3$–$C_{10}$)cycloalkyl. ($C_2$–$C_9$)heterocycloalkyl, and ($C_2$–$C_9$)heteroaryl;

wherein the ($C_2$–$C_9$)heterocycloalkyl moiety of said $R^3$ ($C_2$–$C_9$)heterocycloalkyl-($CH_2$)$_n$— group may contain from one to three heteroatoms independently selected from nitrogen, sulfur, oxygen, >S(=O), >$SO_2$ or >$NR^6$, wherein said ($C_2$–$C_9$)heterocycloalkyl moiety of said ($C_2$–$C_9$)heterocycloalkyl-($CH_2$)$_m$— group may optionally be substituted on any of the ring carbon atoms capable of forming an additional bond with a substituent independently selected from the group consisting of hydrogen, halo, CN, ($C_1$–$C_6$)alkyl optionally substituted with one or more fluorine atoms, hydroxy, hydroxy-($C_1$–$C_6$)alkyl, ($C_1$–$C_6$)alkoxy optionally substituted with one or more fluorine atoms, ($C_1$–$C_6$)alkoxy($C_1$–$C_6$)alkyl, HO—(C=O)—, ($C_1$–$C_6$)alkyl-O—(C=O)—, HO—(C=O)—($C_1$–$C_6$)alkyl, ($C_1$–$C_6$)alkyl-O—(C=O)—($C_1$–$C_6$)alkyl, ($C_1$–$C_6$)alkyl-(C=O)—O—, ($C_1$–$C_6$)alkyl-(C=O)—O—($C_1$–$C_6$)alkyl, H(O=C)—, H(O=C)—($C_1$–$C_6$)alkyl, ($C_1$–$C_6$)alkyl(O=C)—, ($C_1$–$C_6$)alkyl(O=C)—($C_1$–$C_6$)alkyl, $NO_2$, amino, ($C_1$–$C_6$)alkylamino, [($C_1$–$C_6$)alkyl]$_2$amino, amino($C_1$–$C_6$)alkyl, ($C_1$–$C_6$)alkylamino($C_1$–$C_6$)alkyl, [($C_1$–$C_6$)alkyl]$_2$amino($C_1$–$C_6$)alkyl, $H_2$N—(C=O)—, ($C_1$–$C_6$)alkyl-NH—(C=O)—, [($C_1$–$C_6$)alkyl]$_2$N—(C=O)—, $H_2$N(C=O)—($C_1$–$C_6$)alkyl, ($C_1$–$C_6$)alkyl-HN(C=O)—($C_1$–$C_6$)alkyl, [($C_1$–$C_6$)alkyl]$_2$N—(C=O)—($C_1$–$C_6$)alkyl, H(O=C)—NH—, ($C_1$–$C_6$)alkyl(C=O)—NH, ($C_1$–$C_6$)alkyl(C=O)—[NH]($C_1$–$C_6$)alkyl, ($C_1$–$C_6$)alkyl(C=O)—[N($C_1$–$C_6$)alkyl]($C_1$–$C_6$)alkyl, ($C_1$–$C_6$)alkyl-S—, ($C_1$–$C_6$)alkyl-(S=O)—, ($C_1$–$C_6$)alkyl-$SO_2$—, ($C_1$–$C_6$)alkyl-$SO_2$—NH—, $H_2$N—$SO_2$—, $H_2$N—$SO_2$—($C_1$–$C_6$)alkyl, ($C_1$–$C_6$)alkylHN—$SO_2$—($C_1$–$C_6$)alkyl, [($C_1$–$C_6$)alkyl]$_2$N—$SO_2$—($C_1$–$C_6$)alkyl, $CF_3SO_3$—, ($C_1$–$C_6$)alkyl-$SO_3$—, phenyl, ($C_3$–$C_{10}$)cycloalkyl, ($C_2$–$C_9$)heterocycloalkyl, and ($C_2$–$C_9$)heteroaryl;

wherein the ($C_2$–$C_9$)heteroaryl moiety of said $R^3$ ($C_2$–$C_9$)heteroaryl-($CH_2$)$_n$— group may contain from one to three heteroatoms independently selected from nitrogen, sulfur or oxygen wherein said ($C_2$–$C_9$)heteroaryl moiety of said ($C_2$–$C_9$)heteroaryl-($CH_2$)$_n$— group may optionally be substituted on any of the ring carbon atoms capable of forming an additional bond with a substituent selected from the group consisting of hydrogen, halo, CN, ($C_1$–$C_6$)alkyl optionally substituted with one or more fluorine atoms, hydroxy, hydroxy-($C_1$–$C_6$)alkyl, ($C_1$–$C_6$)alkoxy optionally substituted with one or more fluorine atoms, ($C_1$–$C_6$)alkoxy($C_1$–$C_6$)alkyl, HO—(C=O)—, ($C_1$–$C_6$)alkyl-O—(C=O)—, HO—(C=O)—($C_1$–$C_6$)alkyl, ($C_1$–$C_6$)alkyl-O—(C=O)—($C_1$–$C_6$)alkyl, ($C_1$–$C_6$)alkyl-(C=O)—O—, ($C_1$–$C_6$)alkyl-(C=O)—O—($C_1$–$C_6$)alkyl, H(O=C)—, H(O=C)—($C_1$–$C_6$)alkyl, ($C_1$–$C_6$)alkyl(O=C)—, ($C_1$–$C_6$)alkyl(O=C)—($C_1$–$C_6$)alkyl, $NO_2$, amino, ($C_1$–$C_6$)alkylamino, [($C_1$–$C_6$)alkyl]$_2$amino, amino($C_1$–$C_6$)alkyl, ($C_1$–$C_6$)alkylamino($C_1$–$C_6$)alkyl, [($C_1$–$C_6$)alkyl]$_2$amino($C_1$–$C_6$)alkyl, $H_2$N—(C=O)—, ($C_1$–$C_6$)alkyl-NH—(C=O)—, [($C_1$–$C_6$)alkyl]$_2$N—(C=O)—, $H_2$N(C=O)—($C_1$–$C_6$)alkyl, ($C_1$–$C_6$)alkyl-HN(C=O)—($C_1$–$C_6$)alkyl, [($C_1$–$C_6$)alkyl]$_2$N—(C=O)—($C_1$–$C_6$)alkyl, H(O=C)—NH—, ($C_1$–$C_6$)alkyl(C=O)—NH, ($C_1$–$C_6$)alkyl(C=O)—[NH]($C_1$–$C_6$)alkyl, ($C_1$–$C_6$)alkyl(C=O)—[N($C_1$–$C_6$)alkyl]($C_1$–$C_6$)alkyl, ($C_1$–$C_6$)alkyl-S—, ($C_1$–$C_6$)alkyl-(S=O)—, ($C_1$–$C_6$)alkyl-$SO_2$—, ($C_1$–$C_6$)alkyl-$SO_2$—NH—, $H_2$N—$SO_2$—, $H_2$N—$SO_2$—($C_1$–$C_6$)alkyl, ($C_1$–$C_6$)alkylHN—$SO_2$—($C_1$–$C_6$)alkyl, [($C_1$–$C_6$)alkyl]$_2$N—$SO_2$—($C_1$–$C_6$)alkyl, $CF_3SO_3$—, ($C_1$–$C_6$)alkyl-$SO_3$—, phenyl, ($C_3$–$C_{10}$)cycloalkyl, ($C_2$–$C_9$)heterocycloalkyl, and ($C_2$–$C_9$)heteroaryl; and wherein said aryl moiety of said $R^3$ aryl-($CH_2$)$_n$— group is optionally substituted phenyl or naphthyl, wherein said phenyl and naphthyl may optionally be substituted with from one to three substituents independently selected from the group consisting of hydrogen, halo, CN, ($C_1$–$C_6$)alkyl optionally substituted with one or more fluorine atoms, hydroxy, hydroxy-($C_1$–$C_6$)alkyl, ($C_1$–$C_6$)alkoxy optionally substituted with one or more fluorine atoms, ($C_1$–$C_6$)alkoxy($C_1$–$C_6$)alkyl, HO—(C=O)—, ($C_1$–$C_6$)alkyl-O—(C=O)—, HO—(C=O)—($C_1$–$C_6$)alkyl, ($C_1$–$C_6$)alkyl-O—(C=O)—($C_1$–$C_6$)alkyl, ($C_1$–$C_6$)alkyl-(C=O)—O—, ($C_1$–$C_6$)alkyl-(C=O)—O—($C_1$–$C_6$)alkyl, H(O=C)—, H(O=C)—($C_1$–$C_6$)alkyl, ($C_1$–$C_6$)alkyl(O=C)—, ($C_1$–$C_6$)alkyl(O=C)—($C_1$–$C_6$)alkyl, $NO_2$, amino, ($C_1$–$C_6$)alkylamino, [($C_1$–$C_6$)alkyl]$_2$amino, amino($C_1$–$C_6$)alkyl, ($C_1$–$C_6$)alkylamino($C_1$–$C_6$)alkyl, [($C_1$–$C_6$)alkyl]$_2$amino($C_1$–$C_6$)alkyl, $H_2$N—(C=O)—, ($C_1$–$C_6$)alkkyl-NH—(C=O)—, [($C_1$–$C_6$)alkyl]$_2$N—(C=O)—, $H_2$N(C=O)—($C_1$–$C_6$)alkyl, ($C_1$–$C_6$)alkyl-HN(C=O)—($C_1$–$C_6$)alkyl, [($C_1$–$C_6$)alkyl]$_2$N—(C=O)—($C_1$–$C_6$)alkyl, H(O=C)—NH—, ($C_1$–$C_6$)alkyl(C=O)—NH, ($C_1$–$C_6$)alkyl(C=O)—[NH]($C_1$–$C_6$)alkyl, ($C_1$–$C_6$)alkyl(C=O)—[N($C_1$–$C_6$)alkyl]($C_1$–$C_6$)alkyl, ($C_1$–$C_6$)alkyl-S—, ($C_1$–$C_6$)alkyl-(S=O)—, ($C_1$–$C_6$)alkyl-$SO_2$—, ($C_1$–$C_6$)alkyl-$SO_2$—NH—, $H_2$N—$SO_2$—, $H_2$N—$SO_2$—($C_1$–$C_6$)alkyl, ($C_1$–$C_6$)alkylHN—$SO_2$—($C_1$–$C_6$)alkyl, [($C_1$–$C_6$)alkyl]$_2$N—$SO_2$—($C_1$–$C_6$)alkyl, $CF_3SO_3$—, ($C_1$–$C_6$)alkyl-$SO_3$—, phenyl, ($C_3$–$C_{10}$)cycloalkyl, ($C_2$–$C_9$)heterocycloalkyl, and ($C_2$–$C_9$)heteroaryl;

or $R^3$ and the carbon to which it is attached form a five to seven membered carbocyclic ring, wherein any of the carbon atoms of said five membered carbocyclic ring may optionally be substituted with a substituent selected from the group consisting of hydrogen, halo, CN, ($C_1$–$C_6$)alkyl optionally substituted with one or more fluorine atoms (preferably one to three fluorine atoms), hydroxy, hydroxy-($C_1$–$C_6$)alkyl, ($C_1$–$C_6$)alkoxy optionally substituted with one or more fluorine atoms (preferably one to three fluorine atoms), ($C_1$–$C_6$)alkoxy($C_1$–$C_6$)alkyl, HO—(C=O)—, ($C_1$–$C_6$)alkyl-O—(C=O)—, HO—(C=O)—($C_1$–$C_6$)alkyl, ($C_1$–$C_6$)alkyl-O—(C=O)—($C_1$–$C_6$)alkyl, ($C_1$–$C_6$)alkyl-(C=O)—O—, ($C_1$–$C_6$)alkyl-(C=O)—O—($C_1$–$C_6$)alkyl, H(O=C)—, H(O=C)—($C_1$–$C_6$)alkyl, ($C_1$–$C_6$)alkyl(O=C)—, ($C_1$–$C_6$)alkyl(O=C)—($C_1$–$C_6$)alkyl, $NO_2$, amino, ($C_1$–$C_6$)alkylamino, [($C_1$–$C_6$)alkyl]$_2$amino, amino($C_1$–$C_6$)alkyl, ($C_1$–$C_6$)alkylamino($C_1$–$C_6$)alkyl, [($C_1$–$C_6$)alkyl]$_2$amino($C_1$–$C_6$)alkyl, $H_2$N—(C=O)—, ($C_1$–$C_6$)alkyl-NH—(C=O)—, [($C_1$–$C_6$)alkyl]$_2$N—(C=O)—, $H_2$N(C=O)—($C_1$–$C_6$)alkyl, ($C_1$–$C_6$)alkyl-HN(C=O)—($C_1$–$C_6$)alkyl, [($C_1$–$C_6$)alkyl]$_2$N—(C=O)—($C_1$–$C_6$)alkyl, H(O=C)—NH—, ($C_1$–$C_6$)alkyl(C=O)—NH, ($C_1$–$C_6$)alkyl(C=O)—[NH]($C_1$–$C_6$)alkyl, ($C_1$–$C_6$)alkyl(C=O)—[N($C_1$–$C_6$)alkyl]($C_1$–$C_6$)alkyl, ($C_1$–$C_6$)

alkyl-S—, ($C_1$–$C_6$)alkyl-(S=O)—, ($C_1$–$C_6$)alkyl-$SO_2$—, ($C_1$–$C_6$)alkyl-$SO_2$—NH—, $H_2N$—$SO_2$—, $H_2N$—$SO_2$—($C_1$–$C_6$)alkyl, ($C_1$–$C_6$)alkylHN—$SO_2$—($C_1$–$C_6$)alkyl, [($C_1$–$C_6$)alkyl]$_2$N—$SO_2$—($C_1$–$C_6$)alkyl, $CF_3SO_3$—, ($C_1$–$C_6$)alkyl-$SO_3$—, phenyl, ($C_3$–$C_{10}$)cycloalkyl, ($C_2$–$C_9$)heterocycloalkyl, and ($C_2$–$C_9$)heteroaryl; wherein one of the carbon-carbon bonds of said five to seven membered carbocyclic ring may optionally be fused to an optionally substituted phenyl ring, wherein said substitutents may be independently selected from hydrogen, halo, CN, ($C_1$–$C_6$)alkyl optionally substituted with one or more fluorine atoms (preferably one to three fluorine atoms), hydroxy, hydroxy-($C_1$–$C_6$)alkyl, ($C_1$–$C_6$)alkoxy optionally substituted with one or more fluorine atoms (preferably one to three atoms), ($C_1$–$C_6$)alkoxy($C_1$–$C_6$)alkyl, HO—(C=O)—, ($C_1$–$C_6$)alkyl-O—(C=O)—, HO—(C=O)—($C_1$–$C_6$)alkyl, ($C_1$–$C_6$)alkyl-O—(C=O)—($C_1$–$C_6$)alkyl, ($C_1$–$C_6$)alkyl-(C=O)—O—, ($C_1$–$C_6$)alkyl-(C=O)—O—($C_1$–$C_6$)alkyl, H(O=C)—, H(O=C)—($C_1$–$C_6$)alkyl, ($C_1$–$C_6$)alkyl(O=C)—, ($C_1$–$C_6$)alkyl(O=C)—($C_1$–$C_6$)alkyl, $NO_2$, amino, ($C_1$–$C_6$)alkylamino, [($C_1$–$C_6$)alkyl]$_2$amino, amino($C_1$–$C_6$)alkyl, ($C_1$–$C_6$)alkylamino($C_1$–$C_6$)alkyl, [($C_1$–$C_6$)alkyl]$_2$amino($C_1$–$C_6$)alkyl, $H_2N$—(C=O)—, ($C_1$–$C_6$)alkyl-NH—(C=O)—, [($C_1$–$C_6$)alkyl]$_2$N—(C=O)—, $H_2N$(C=O)—($C_1$–$C_6$)alkyl, ($C_1$–$C_6$)alkyl-HN(C=O)—($C_1$–$C_6$)alkyl, [($C_1$–$C_6$)alkyl]$_2$N—(C=O)—($C_1$–$C_6$)alkyl, H(O=C)—NH—, ($C_1$–$C_6$)alkyl(C=O)—NH, ($C_1$–$C_6$)alkyl(C=O)— [NH] ($C_1$–$C_6$)alkyl, ($C_1$–$C_6$)alkyl(C=O)—[N($C_1$–$C_6$)alkyl]($C_1$–$C_6$)alkyl, ($C_1$–$C_6$)alkyl-S—, ($C_1$–$C_6$)alkyl-(S=O)—, ($C_1$–$C_6$)alkyl-$SO_2$—, ($C_1$–$C_6$)alkyl-$SO_2$—NH—, $H_2N$—$SO_2$—, $H_2N$—$SO_2$—($C_1$–$C_6$)alkyl, ($C_1$–$C_6$)alkylHN—$SO_2$—($C_1$–$C_6$)alkyl, [($C_1$–$C_6$)alkyl]$_2$N—$SO_2$—($C_1$–$C_6$)alkyl, $CF_3SO_3$—, ($C_1$–$C_6$)alkyl-$S$—$O_3$—, phenyl, ($C_3$–$C_{10}$)cycloalkyl, ($C_2$–$C_9$)heterocycloalkyl, and ($C_2$–$C_9$)heteroaryl;

$R^4$ is hydrogen, ($C_1$–$C_6$)alkyl, hydroxy, ($C_1$–$C_6$)alkoxy, hydroxy($C_1$–$C_6$)alkyl, ($C_1$–$C_6$)alkoxy(C=O)—, ($C_3$–$C_{10}$)cycloalkyl-($CH_2$)$_p$—, ($C_2$–$C_9$)heterocycloalkyl-($CH_2$)$_p$—, ($C_2$–$C_9$)heteroaryl-($CH_2$)$_p$—, phenyl-($CH_2$)$_p$—, or naphthyl-($CH_2$)$_p$—, wherein p is an integer from zero to four; wherein said ($C_2$–$C_9$)heterocycloalkyl, ($C_2$–$C_9$)heteroaryl, phenyl and naphthyl groups of said ($C_2$–$C_9$)heterocycloalkyl-($CH_2$)$_p$—, ($C_2$–$C_9$)heteroaryl-($CH_2$)$_p$—, phenyl-($CH_2$)$_p$—, or naphthyl-($CH_2$)$_p$— may be optionally substituted on any of the ring atoms capable of supporting an additional bond with a substituent selected from the group consisting of hydrogen, halo, CN, ($C_1$–$C_6$)alkyl optionally substituted with one or more fluorine atoms, hydroxy, hydroxy-($C_1$–$C_6$)alkyl, ($C_1$–$C_6$)alkoxy optionally substituted with one or more fluorine atoms, ($C_1$–$C_6$)alkoxy($C_1$–$C_6$)alkyl, HO—(C=O)—, ($C_1$–$C_6$)alkyl-O—(C=O)—, HO—(C=O)—($C_1$–$C_6$)alkyl, ($C_1$–$C_6$)alkyl-O—(C=O)—($C_1$–$C_6$)alkyl, ($C_1$–$C_6$)alkyl-(C=O)—O—, ($C_1$–$C_6$)alkyl-(C=O)—O—($C_1$–$C_6$)alkyl, H(O=C)—, H(O=C)—($C_1$–$C_6$)alkyl, ($C_1$–$C_6$) alkyl(O=C)—, ($C_1$–$C_6$)alkyl(O=C)—($C_1$–$C_6$)alkyl, $NO_2$, amino, ($C_1$–$C_6$)alkylamino, [($C_1$–$C_6$)alkyl]$_2$ amino, amino ($C_1$–$C_6$)alkyl, ($C_1$–$C_6$)alkylamino ($C_1$–$C_6$)alkyl, [($C_1$–$C_6$)alkyl]$_2$amino($C_1$–$C_6$)alkyl, $H_2N$—(C=O)—, ($C_1$–$C_6$)alkyl-NH—(C=O)—, [($C_1$–$C_6$)alkyl]$_2$N—(C=O)—, $H_2N$(C=O)—($C_1$–$C_6$)alkyl, ($C_1$–$C_6$)alkyl-HN(C=O)—($C_1$–$C_6$)alkyl, [($C_1$–$C_6$)alkyl]$_2$N—(C=O)—($C_1$–$C_6$)alkyl, H(O=C)—NH—, ($C_1$–$C_6$)alkyl(C=O)—NH, ($C_1$–$C_6$)alkyl(C=O)—[NH]($C_1$–$C_6$)alkyl, ($C_1$–$C_6$)alkyl(C=O)—[N($C_1$–$C_6$)alkyl]($C_1$–$C_6$)alkyl, ($C_1$–$C_6$)alkyl-S—, ($C_1$–$C_6$)alkyl-(S=O)—, ($C_1$–$C_6$)alkyl-$SO_2$—, ($C_1$–$C_6$)alkyl-$SO_2$—NH—, $H_2N$—$SO_2$—, $H_2N$—$SO_2$—($C_1$–$C_6$)alkyl, ($C_1$–$C_6$)alkylHN—$SO_2$—($C_1$–$C_6$)alkyl, [($C_1$–$C_6$)alkyl]$_2$N—$SO_2$—($C_1$–$C_6$)alkyl, $CF_3SO_3$—, ($C_1$–$C_6$)alkyl-$SO_3$—, phenyl, ($C_3$–$C_{10}$)cycloalkyl, ($C_2$–$C_9$)heterocycloalkyl, and ($C_2$–$C_9$)heteroaryl;

$R^5$ is hydrogen, ($C_1$–$C_6$)alkyl or amino;

$R^6$ is hydrogen, ($C_1$–$C_6$)alkyl, ($C_1$–$C_6$)alkoxy-($CH_2$)$_g$—, ($C_1$–$C_6$)alkoxy(C=O)—($CH_2$)$_g$—, ($C_1$–$C_6$)alkyl-($SO_2$)—($CH_2$)$_g$—, ($C_6$–$C_{10}$)aryloxy-($CH_2$)$_g$—, ($C_6$–$C_{10}$)aryloxy(C=O)—($CH_2$)$_g$—, and ($C_6$–$C_{10}$)aryl-($SO_2$)—($CH_2$)$_g$—, wherein g is an integer from 1 to four;

with the proviso that when either $R^4$ or $R^5$ is hydrogen, and the other of $R^4$ or $R^5$ is ($C_1$–$C_6$)alkyl, or morpholinoethyl, $R^2$ is ($C_3$–$C_{10}$)cycloalkyl or isopropyl and $R^3$ is ($C_3$–$C_5$)alkyl, phenyl, methylvinyl, dimethylvinyl, halovinyl, hydroxy($C_1$–$C_3$)alkyl or amino($C_1$–$C_4$)alkyl then $R^1$ must be other than indol-5-yl, 6-azaindol-2-yl, 2,3-dichloro-pyrol-5-yl, 4-hydroxyquinolin-3-yl, 2-hydroxyquinoxalin-3-yl, 6-azaindolin-3-yl, or optionally substituted indol-2 or 3-yl;

and the pharmaceutically acceptable salts of such compounds.

2. A compound according to claim 1, wherein said compound of formula I has the exact stereochemistry depicted in formula

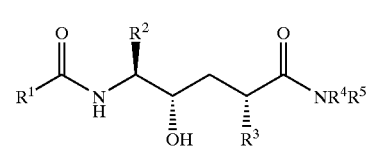

Ia wherein $R^1$, $R^2$, $R^3$, $R^4$ and $R^5$ are as described in claim 1.

3. A compound according to claim 1, wherein $R^2$ is optionally substituted benzyl.

4. A compound according to claim 1, wherein $R^3$ is optionally substituted ($C_1$–$C_{10}$)alkyl or ($C_3$–$C_{10}$)cycloalkyl-($CH_2$)$_n$—.

5. A compound according to claim 1, wherein $R^3$ is optionally substituted n-butyl, t-butyl, 2-methylpropyl, 2-methyl-butyl, 3-methylbutyl, n-pentyl, 2-methyl-pentyl, cyclopentyl, cyclohexyl, 2-methyl-cyclohexyl, or cyclohexyl-methyl.

6. A compound according to claim 1, wherein $R^3$ is substituted by fluoro or hydroxy.

7. A compound according to claim 2, wherein $R^3$ is substituted by fluoro or hydroxy.

8. A compound according to claim 5 wherein $R^3$ is substituted by fluoro or hydroxy.

9. A compound according to claim 1, wherein $R^3$ is 4,4-difluoro-cyclohexylmethyl, 2-fluoro-2-methyl-butyl, isobutyl, or 1-hydroxy-cyclohexyl.

10. A compound according to claim 2, wherein $R^3$ is 4,4-difluoro-cyclohexylmethyl, 2-fluoro-2-methyl-butyl, 2-methylpropyl, 2-hydroxy-2-methylbutyl, 2-hydroxy-2-methyl-propyl, or 1-hydroxy-cyclohexyl.

11. A compound according to claim 1 wherein $R^4$ and $R^5$ are independently selected from hydrogen, hydroxy, amino, methyl, or ethyl.

12. A compound according to claim 5 wherein $R^4$ and $R^5$ are independently selected from hydrogen, hydroxy, amino, methyl, or ethyl.

13. A compound according to claim 1, wherein said compound is:

quinoxaline-2-carboxylic acid [4(R)-carbamoyl-7-fluoro-1-(3(S)-fluoro-benzyl)-2(S)-hydroxy-7-methyl-octyl]-amide;

quinoxaline-2-carboxylic acid [4(R)-carbamoyl-1-(2(S)-fluoro-benzyl)-2(S)-hydroxy-7-methyl-octyl]-amide;

quinoxaline-2-carboxylic acid [1(S)-benzyl-4(S)-carbamoyl-4(S)-(2,6-dimethyl-tetrahydro-pyran-4-yl)-2(S)-hydroxy-butyl]-amide;

quinoxaline-2-carboxylic acid 1(S)-benzyl-4(R)-carbamoyl-7-fluoro-2(S)-hydroxy-7-methyl-octyl)-amide;

quinoxaline-2-carboxylic acid 1(S)-benzyl-5-cyclohexyl-2(S)-hydroxy-4(R)-methylcarbamoyl-pentyl)-amide;

quinoxaline-2-carboxylic acid 1(S)-cyclohexylmethyl-2(S)-hydroxy-7-methyl-4(R)-methylcarbamoyl-octyl)-amide;

quinoxaline-2-carboxylic acid [1(S)-benzyl-2(S)-hydroxy-4(S)-hydroxycarbamoyl-4-(1-hydroxy-4-methyl-cyclohexyl)-butyl]-amide;

quinoxaline-2-carboxylic acid [1(S)-benzyl-4(S)-(4,4-difluoro-1-hydroxy-cyclohexyl)-2(S)-hydroxy-4-hydroxycarbamoyl-butyl]-amide;

quinoxaline-2-carboxylic acid [1(S)-benzyl4(S)-carbamoyl-4(S)-(4,4-difluoro-cyclohexyl)-2(S)-hydroxy-butyl]-amide;

quinoxaline-2-carboxylic acid (4(R)-carbamoyl-2(S)-hydroxy-7-methyl-1(S)-thiophen-2-ylmethyl-octyl)-amide;

quinoxaline-2-carboxylic acid 1(S)-benzyl-4(R)-carbamoyl-7-chloro-2(S)-hydroxy-oct-6-enyl)-amide;

quinoxaline-2-carboxylic acid 1(S)-benzyl4(R)-carbamoyl-2(S)-hydroxy-5-phenyl-pentyl)-amide;

quinoxaline-2-carboxylic acid (4(R)-carbamoyl-2(S)-hydroxy-7-methyl-1(S)-thiazol-4(R)-ylmethyl-octyl)-amide.

14. A pharmaceutical composition for treating a disorder or condition selected from autoimmune diseases, acute and chronic inflammatory conditions, allergic conditions, infection associated with inflammation, viral, transplantation tissue rejection, atherosclerosis, restenosis, HIV infectivity, and granulomatous in a mammal, comprising an amount of a compound according to claim 1 that is effective in treating such disorder or condition and a pharmaceutically acceptable carrier.

15. A pharmaceutical composition for treating a disorder or condition that can be treated by inhibiting MIP-1α binding to the receptor CCR1 in a mammal, comprising an amount of a compound according to claim 1, or a pharmaceutically acceptable salt thereof, effective in treating such disorder or condition and a pharmaceutically acceptable carrier.

16. A method for treating a disorder or condition selected from autoimmune diseases, acute and chronic inflammatory conditions, allergic conditions, infection associated with inflammation, viral, transplantation tissue rejection, atherosclerosis, restenosis, HIV infectivity, and granulomatous in a mammal, comprising administering to a mammal in need of such treatment an amount of a compound according to claim 1, or a pharmaceutically acceptable salt thereof, that is effective in treating such disorder or condition.

17. A method for treating a disorder or condition that can be treated by antagonizing the CCR1 receptor in a mammal, comprising administering to a mammal in need of such treatment an amount of a compound according to claim 1, or a pharmaceutically acceptable salt thereof, that is effective in treating such disorder or condition.

18. A pharmaceutical composition for treating a disorder or condition selected from autoimmune diseases, acute and chronic inflammatory conditions, allergic conditions, infection associated with inflammation, viral, transplantation tissue rejection, atherosclerosis, restenosis, HIV infectivity, and granulomatous in a mammal, comprising a CCR1 receptor antagonizing effective amount of a compound according to claim 1, or a pharmaceutically acceptable salt thereof, and a pharmaceutically acceptable carrier.

19. A pharmaceutical composition for treating a disorder or condition that can be treated by antagonizing the CCR1 receptor in a mammal, comprising a CCR1 receptor antagonizing effective amount of a compound according to claim 1, or a pharmaceutically acceptable salt thereof, and a pharmaceutically acceptable carrier.

* * * * *